(12) United States Patent
Parisi et al.

(10) Patent No.: US 9,308,095 B2
(45) Date of Patent: Apr. 12, 2016

(54) FEMORAL COMPONENT FOR A KNEE PROSTHESIS WITH IMPROVED ARTICULAR CHARACTERISTICS

(75) Inventors: Raymond C. Parisi, Wakarusa, IN (US); Nick Drury, Warsaw, IN (US); Charles A. Baldridge, Pierceton, IN (US); James C. Harris, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 280 days.

(21) Appl. No.: 13/459,060

(22) Filed: Apr. 27, 2012

(65) Prior Publication Data

US 2012/0323335 A1    Dec. 20, 2012

Related U.S. Application Data

(63) Continuation-in-part of application No. 13/161,624, filed on Jun. 16, 2011, now Pat. No. 8,551,179.

(60) Provisional application No. 61/561,658, filed on Nov. 18, 2011, provisional application No. 61/579,873, filed on Dec. 23, 2011, provisional application No. 61/592,575, filed on Jan. 30, 2012, provisional application No. 61/594,113, filed on Feb. 2, 2012, provisional application No. 61/621,370, filed on Apr. 6, 2012, provisional application No. 61/621,372, filed on Apr. 6, 2012, provisional application No. 61/621,373, filed on Apr. 6, 2012.

(51) Int. Cl.
*A61F 2/38* (2006.01)

(52) U.S. Cl.
CPC ............. *A61F 2/3859* (2013.01); *A61F 2/3886* (2013.01)

(58) Field of Classification Search
CPC ............................ A61F 2/3859; A61F 2/3886
USPC ................................ 623/20.21, 20.31, 20.35
See application file for complete search history.

(56) References Cited

U.S. PATENT DOCUMENTS

| 4,081,866 A | 4/1978 | Upshaw et al. |
| 4,340,978 A | 7/1982 | Buechel et al. |
| 4,662,889 A | 5/1987 | Zichner et al. |
| 4,888,020 A | 12/1989 | Horber |
| 4,944,756 A | 7/1990 | Kenna |
| 5,061,271 A | 10/1991 | Van Zile |
| 5,133,758 A | 7/1992 | Hollister |

(Continued)

FOREIGN PATENT DOCUMENTS

| AU | 2006325787 B2 | 10/2013 |
| CN | 101959475 A | 1/2011 |

(Continued)

OTHER PUBLICATIONS

"U.S. Appl. No. 13/459,061, Restriction Requirement mailed Nov. 12, 2013", 5 pgs.

(Continued)

*Primary Examiner* — David Isabella
*Assistant Examiner* — Christine Nelson
(74) *Attorney, Agent, or Firm* — Schwegman Lundberg & Woessner, P.A.

(57) ABSTRACT

An orthopaedic knee prosthesis includes a femoral component which exhibits enhanced articular features, minimizes removal of healthy bone stock from the distal femur, and minimizes the impact of the prosthesis on adjacent soft tissues of the knee.

20 Claims, 30 Drawing Sheets

(56) References Cited

U.S. PATENT DOCUMENTS

| | | |
|---|---|---|
| 5,137,536 A | 8/1992 | Koshino |
| 5,226,915 A | 7/1993 | Bertin |
| 5,282,861 A | 2/1994 | Kaplan |
| 5,326,361 A | 7/1994 | Hollister |
| 5,445,642 A | 8/1995 | McNulty et al. |
| 5,549,688 A | 8/1996 | Ries et al. |
| 5,609,643 A | 3/1997 | Colleran et al. |
| 5,681,354 A | 10/1997 | Eckhoff |
| 5,688,279 A | 11/1997 | McNulty et al. |
| 5,728,162 A | 3/1998 | Eckhoff |
| 5,776,201 A | 7/1998 | Colleran et al. |
| 5,824,105 A | 10/1998 | Ries et al. |
| 5,871,546 A | 2/1999 | Colleran et al. |
| 5,935,173 A | 8/1999 | Roger et al. |
| 6,013,103 A | 1/2000 | Kaufman et al. |
| 6,039,764 A | 3/2000 | Pottenger et al. |
| 6,106,529 A | 8/2000 | Techiera |
| 6,152,960 A | 11/2000 | Pappas |
| 6,197,064 B1 | 3/2001 | Haines et al. |
| 6,217,619 B1 | 4/2001 | Keller |
| 6,235,060 B1 | 5/2001 | Kubein-Meesenburg et al. |
| 6,264,697 B1 | 7/2001 | Walker |
| 6,325,828 B1 | 12/2001 | Dennis et al. |
| 6,364,911 B1 | 4/2002 | Schmotzer et al. |
| 6,540,786 B2 | 4/2003 | Chibrac et al. |
| 6,540,787 B2 | 4/2003 | Biegun et al. |
| 6,589,283 B1 | 7/2003 | Metzger et al. |
| 6,616,696 B1 | 9/2003 | Merchant |
| 6,699,291 B1 | 3/2004 | Augoyard et al. |
| 6,712,856 B1 | 3/2004 | Carignan et al. |
| 6,770,099 B2 | 8/2004 | Andriacchi et al. |
| 6,802,865 B2 | 10/2004 | Biegun et al. |
| 6,846,329 B2 | 1/2005 | Mcminn |
| 6,893,467 B1 | 5/2005 | Bercovy |
| 7,081,137 B1 | 7/2006 | Servidio |
| 7,306,609 B2 | 12/2007 | Schmotzer et al. |
| 7,364,590 B2 | 4/2008 | Siebel |
| 7,413,577 B1 | 8/2008 | Servidio |
| 7,442,196 B2 | 10/2008 | Fisher et al. |
| 7,678,152 B2 | 3/2010 | Suguro et al. |
| 7,695,520 B2 | 4/2010 | Metzger et al. |
| 7,806,897 B1 | 10/2010 | Bonutti |
| 8,062,377 B2 | 11/2011 | Haines |
| 8,075,626 B2 | 12/2011 | Dun |
| 8,088,167 B2 | 1/2012 | Haines |
| 8,298,288 B2 | 10/2012 | Walker |
| 8,357,202 B2 | 1/2013 | Heggendorn et al. |
| 8,377,141 B2 | 2/2013 | Mcminn |
| 8,394,147 B2 | 3/2013 | Otto et al. |
| 8,409,293 B1 | 4/2013 | Howard et al. |
| 8,480,753 B2 | 7/2013 | Collazo et al. |
| 8,480,754 B2 | 7/2013 | Bojarski et al. |
| 8,500,816 B2 | 8/2013 | Dees, Jr. et al. |
| 8,551,179 B2 | 10/2013 | Jones et al. |
| 8,721,732 B2 | 5/2014 | Samuelson et al. |
| 8,932,365 B2 | 1/2015 | Parisi et al. |
| 9,060,868 B2 | 6/2015 | Parisi et al. |
| 2003/0153924 A1 | 8/2003 | Kana et al. |
| 2003/0158606 A1 | 8/2003 | Coon et al. |
| 2003/0225458 A1 | 12/2003 | Donkers et al. |
| 2004/0039450 A1 | 2/2004 | Griner et al. |
| 2004/0172137 A1 | 9/2004 | Blaylock et al. |
| 2004/0249467 A1 | 12/2004 | Meyers et al. |
| 2005/0102032 A1 | 5/2005 | Beynnon et al. |
| 2005/0107884 A1 | 5/2005 | Johnson et al. |
| 2005/0177169 A1 | 8/2005 | Fisher et al. |
| 2005/0283249 A1 | 12/2005 | Carson |
| 2005/0283250 A1 | 12/2005 | Coon et al. |
| 2005/0283251 A1 | 12/2005 | Coon et al. |
| 2005/0283252 A1 | 12/2005 | Coon et al. |
| 2005/0283253 A1 | 12/2005 | Coon et al. |
| 2006/0028773 A1 | 2/2006 | Shimazawa et al. |
| 2006/0129246 A1 | 6/2006 | Steffensmeier |
| 2006/0224244 A1 | 10/2006 | Thomas et al. |
| 2006/0235541 A1 | 10/2006 | Hodorek |
| 2006/0235542 A1 | 10/2006 | Hodorek et al. |
| 2006/0287733 A1 | 12/2006 | Bonutti |
| 2007/0088444 A1 | 4/2007 | Hodorek et al. |
| 2007/0123984 A1 | 5/2007 | Hodorek |
| 2007/0135926 A1 | 6/2007 | Walker |
| 2007/0179607 A1 | 8/2007 | Hodorek et al. |
| 2007/0233269 A1 | 10/2007 | Steines et al. |
| 2007/0260323 A1 | 11/2007 | Earl et al. |
| 2008/0058947 A1 | 3/2008 | Earl et al. |
| 2008/0058948 A1 | 3/2008 | Biegun et al. |
| 2008/0097616 A1 | 4/2008 | Meyers et al. |
| 2008/0119940 A1 | 5/2008 | Otto et al. |
| 2008/0140212 A1 | 6/2008 | Metzger et al. |
| 2008/0188855 A1 | 8/2008 | Brown et al. |
| 2008/0188937 A1 | 8/2008 | Ribic |
| 2008/0188942 A1 | 8/2008 | Brown et al. |
| 2008/0243258 A1 | 10/2008 | Sancheti |
| 2008/0281428 A1 | 11/2008 | Meyers et al. |
| 2008/0288080 A1 | 11/2008 | Sancheti |
| 2009/0036992 A1 | 2/2009 | Tsakonas |
| 2009/0043395 A1 | 2/2009 | Hotokebuchi et al. |
| 2009/0062924 A1 | 3/2009 | Kito et al. |
| 2009/0105772 A1 | 4/2009 | Seebeck et al. |
| 2009/0132055 A1 | 5/2009 | Ferro |
| 2009/0222103 A1 | 9/2009 | Fitz et al. |
| 2009/0265011 A1 | 10/2009 | Mandell |
| 2009/0265013 A1* | 10/2009 | Mandell ............... 623/20.21 |
| 2009/0306786 A1 | 12/2009 | Samuelson |
| 2009/0306787 A1 | 12/2009 | Crabtree et al. |
| 2009/0319047 A1* | 12/2009 | Walker ............... 623/20.15 |
| 2009/0319048 A1* | 12/2009 | Shah et al. ........... 623/20.29 |
| 2009/0319049 A1* | 12/2009 | Shah et al. ........... 623/20.31 |
| 2009/0326663 A1 | 12/2009 | Dun |
| 2009/0326665 A1 | 12/2009 | Wyss et al. |
| 2009/0326666 A1 | 12/2009 | Wyss et al. |
| 2009/0326667 A1 | 12/2009 | Williams et al. |
| 2010/0036499 A1 | 2/2010 | Pinskerova |
| 2010/0036500 A1 | 2/2010 | Heldreth et al. |
| 2010/0042224 A1 | 2/2010 | Otto et al. |
| 2010/0161067 A1 | 6/2010 | Saleh et al. |
| 2010/0191298 A1 | 7/2010 | Earl et al. |
| 2010/0305708 A1 | 12/2010 | Lang |
| 2010/0329530 A1 | 12/2010 | Lang et al. |
| 2011/0022179 A1 | 1/2011 | Andriacchi et al. |
| 2011/0093083 A1 | 4/2011 | Earl et al. |
| 2011/0144760 A1 | 6/2011 | Wong et al. |
| 2011/0218541 A1 | 9/2011 | Bailey et al. |
| 2011/0307067 A1 | 12/2011 | Dees |
| 2012/0203350 A1 | 8/2012 | Hagen et al. |
| 2012/0310362 A1 | 12/2012 | Li et al. |
| 2012/0323334 A1 | 12/2012 | Jones et al. |
| 2012/0323336 A1 | 12/2012 | Parisi et al. |
| 2012/0323337 A1 | 12/2012 | Parisi et al. |
| 2013/0006370 A1 | 1/2013 | Wogoman et al. |
| 2013/0006371 A1 | 1/2013 | Wogoman et al. |
| 2013/0006376 A1 | 1/2013 | Wogoman et al. |
| 2013/0006378 A1 | 1/2013 | Wogoman |
| 2013/0035765 A1 | 2/2013 | Dacus |
| 2013/0197653 A1 | 8/2013 | Hawkins et al. |
| 2013/0204380 A1 | 8/2013 | Mouillet et al. |
| 2013/0211532 A1 | 8/2013 | Samuelson et al. |
| 2013/0226305 A1 | 8/2013 | Donno et al. |
| 2013/0345821 A1 | 12/2013 | Jones et al. |
| 2014/0128973 A1 | 5/2014 | Howard et al. |
| 2014/0142713 A1 | 5/2014 | Wright et al. |
| 2015/0081031 A1 | 3/2015 | Parisi et al. |

FOREIGN PATENT DOCUMENTS

| | | |
|---|---|---|
| CN | 101330883 B | 3/2013 |
| CN | 103732186 A | 4/2014 |
| CN | 103732187 A | 4/2014 |
| CN | 103732188 A | 4/2014 |
| CN | 103747762 A | 4/2014 |
| DE | 202007014128 U1 | 1/2008 |
| EP | 0303467 A2 | 2/1989 |
| EP | 0376658 B1 | 6/1994 |
| EP | 0381352 B1 | 6/1994 |
| EP | 0722721 A1 | 7/1996 |

(56) References Cited

FOREIGN PATENT DOCUMENTS

| | | |
|---|---|---|
| EP | 0567705 B1 | 7/1997 |
| EP | 0993812 A2 | 4/2000 |
| EP | 1013232 A2 | 6/2000 |
| EP | 1285638 A2 | 2/2003 |
| EP | 1033117 B1 | 6/2004 |
| EP | 975286 B1 | 8/2004 |
| EP | 1477142 A2 | 11/2004 |
| EP | 1477143 A1 | 11/2004 |
| EP | 1013232 B1 | 10/2005 |
| EP | 1285638 B1 | 11/2005 |
| EP | 1719478 A2 | 11/2006 |
| EP | 1722721 A1 | 11/2006 |
| EP | 1354571 B1 | 6/2007 |
| EP | 1862150 A1 | 12/2007 |
| EP | 2004099 A2 | 12/2008 |
| EP | 1867302 B1 | 9/2009 |
| EP | 2147660 A1 | 1/2010 |
| EP | 2158878 A1 | 3/2010 |
| EP | 1555962 B1 | 2/2011 |
| EP | 2324799 A2 | 5/2011 |
| EP | 2335654 A1 | 6/2011 |
| EP | 2720646 A1 | 4/2014 |
| FR | 2901996 A1 | 12/2007 |
| JP | 64068255 A | 3/1989 |
| JP | 3267055 A | 11/1991 |
| JP | 0553501 A | 3/1993 |
| JP | 0568987 A | 3/1993 |
| JP | 9149908 A | 6/1997 |
| JP | 11504226 A | 4/1999 |
| JP | 11511347 A | 10/1999 |
| JP | 3469972 B2 | 11/2003 |
| JP | 3495161 B2 | 2/2004 |
| JP | 2004166802 A | 6/2004 |
| JP | 2005532089 A | 10/2005 |
| JP | 2008502393 A | 1/2008 |
| JP | 2008503327 A | 2/2008 |
| JP | 2009519781 A | 5/2009 |
| JP | 4820547 B2 | 11/2011 |
| JP | 5571863 B1 | 7/2014 |
| JP | 2014522290 A | 9/2014 |
| JP | 2014522291 A | 9/2014 |
| JP | 2014522292 A | 9/2014 |
| JP | 2014522671 A | 9/2014 |
| WO | WO95-35074 A1 | 12/1995 |
| WO | WO-9603939 A1 | 2/1996 |
| WO | WO-0023010 A1 | 4/2000 |
| WO | WO-03094782 A2 | 11/2003 |
| WO | WO2004/016204 A1 | 2/2004 |
| WO | WO-2005037147 A1 | 4/2005 |
| WO | WO-2005051240 A1 | 6/2005 |
| WO | WO2005/122967 A1 | 12/2005 |
| WO | WO-2006058057 A2 | 6/2006 |
| WO | WO-2007007841 A1 | 1/2007 |
| WO | WO-2007054553 A1 | 5/2007 |
| WO | WO-2007070859 A2 | 6/2007 |
| WO | WO-2007109641 A2 | 9/2007 |
| WO | WO-2008054389 A1 | 5/2008 |
| WO | WO2009/088234 A2 | 7/2009 |
| WO | WO-2009088236 A2 | 7/2009 |
| WO | WO-2009088238 A2 | 7/2009 |
| WO | WO-2009105495 A1 | 8/2009 |
| WO | WO2010/108550 A1 | 9/2010 |
| WO | WO-2011072235 A2 | 6/2011 |
| WO | WO-2012031774 A1 | 3/2012 |
| WO | WO-2012112698 A2 | 8/2012 |
| WO | WO-2012173704 A1 | 12/2012 |
| WO | WO-2012173706 A1 | 12/2012 |
| WO | WO-2012173740 A1 | 12/2012 |

OTHER PUBLICATIONS

"U.S. Appl. No. 13/459,064, Restriction Requirement mailed Nov. 25, 2013", 5 pgs.

"U.S. Appl. No. 13/819,528, Non Final Office Action mailed Dec. 6, 2013", 15 pgs.

"Canadian Application Serial No. 2,641,966, Office Action mailed Jul. 16, 2013", 2 pgs.

"U.S. Appl. No. 13/161,624, Response filed Feb. 26, 2013 to Restriction Requirement mailed Sep. 26, 2012", 9 pgs.

"U.S. Appl. No. 13/161,624, Restriction Requirement mailed Sep. 26, 2012", 8 pgs.

"U.S. Appl. No. 13/459,061, Preliminary Amendment filed Apr. 27, 2012", 6 pgs.

"U.S. Appl. No. 13/459,064, Preliminary Amendment filed Apr. 27, 2012", 6 pgs.

"Gender Solutions Patello-Femoral Joint (PFJ) System: Surgical Technique", Zimmer Inc., (2008, 2009), 38 pgs.

"International Application Serial No. PCT/US2012/035688, Search Report mailed Sep. 17, 2012", 7 pgs.

"International Application Serial No. PCT/US2012/035688, Written Opinion mailed Sep. 17, 2012", 11 pgs.

"International Application Serial No. PCT/US2012/035691, Search Report mailed Sep. 17, 2012", 7 pgs.

"International Application Serial No. PCT/US2012/035691, Written Opinion mailed Sep. 17, 2012", 11 pgs.

"International Application Serial No. PCT/US2012/035693, Search Report mailed Oct. 9, 2012", 7 pgs.

"International Application Serial No. PCT/US2012/035693, Written Opinion mailed Oct. 9, 2012", 11 pgs.

"International Application Serial No. PCT/US2012/038531, Search Report mailed Oct. 8, 2012", 14 pgs.

"International Application Serial No. PCT/US2012/038531, Written Opinion mailed Oct. 8, 2012", 10 pgs.

"NexGen LPS-Flex Mobile and LPS-Mobile Bearing Knees", Zimmer, Inc., (2007, 2008), 4 pgs.

"Unicompartmental High Flex Knee: Intramedullary, Spacer Block Option and Extramedullary Minimally Invasive Surgical Techniques", Zimmer, Inc., (2004, 2009, 2010), 62 pgs.

Zimmer LPS-Flex Fixed Bearing Knee Surgical Technique, Zimmer, Inc. 2004, 2007, 2008.

Zimmer NexGen Complete Knee Solution Surgical Technique for the CR-Flex Fixed Bearing Knee, Zimmer, Inc. 2003.

Zimmer NexGen Complete Knee Solution Extramedullary/Intramedullary Tibial Resector Surgical Technique, Zimmer, Inc. 2000, 2008, 2009.

Zimmer NexGen LPS Fixed Knee Surgical Technique, Zimmer, Inc. 2002, 2008.

Zimmer NexGen LPS-Flex Mobile and LPS-Mobile Bearing Knees Brochure, Zimmer, Inc. 2007, 2008.

NexGen Implant Options Surgeon-Specific, Zimmer, Inc. 2000.

"U.S. Appl. No. 13/161,624, Notice of Allowance mailed Mar. 12, 2013", 11 pgs.

Partial Search Report mailed Jul. 10, 2012 in International Application No. PCT/US2012/035691 from the International Searching Authority.

"Answer filed Dec. 1, 2010 of Zimmer, Inc and Zimmer Technology, Inc", *W. Norman Scott and Giles R Scuderi* vs. *Zimmer, Inc and Zimmer Technology, Inc* in the US District Court of Delaware in Case No. 10-772-GMS, (Dec. 1, 2010), 36 pgs.

"U.S. Appl. No. 11/611,021, Non-Final Office Action mailed Dec. 7, 2009", 4 pgs.

"U.S. Appl. No. 11/611,021, Final Office Action mailed Mar. 10, 2011", 7 pgs.

"U.S. Appl. No. 11/611,021, Non Final Office Action mailed Jul. 21, 2010", 8 pgs.

"U.S. Appl. No. 11/611,021, Response filed May 3, 2010 to Non Final Office Action mailed Dec. 7, 2009", 14 pgs.

"U.S. Appl. No. 11/611,021, Response filed Dec. 21, 2010 to Non Final Office Action mailed Jul. 21, 2010", 14 pgs.

"U.S. Appl. No. 11/780,248, Non Final Office Action mailed Feb. 4, 2010", 4 pgs.

"U.S. Appl. No. 11/780,248, Non Final Office Action mailed Jul. 21, 2010", 11 pgs.

"U.S. Appl. No. 11/780,248, Response filed May 3, 2010 to Non Final Office Action mailed Feb. 4, 2010", 13 pgs.

"U.S. Appl. No. 12/974,018, Final Office Action mailed Apr. 13, 2012", 11 pgs.

(56) References Cited

OTHER PUBLICATIONS

"U.S. Appl. No. 12/974,018, Non Final Office Action mailed Nov. 10, 2011", 5 pgs.
"U.S. Appl. No. 12/974,018, Preliminary Amendment filed Dec. 21, 2010", 4 pgs.
"U.S. Appl. No. 12/974,018, Response filed Mar. 8, 2012 to Non Final Office Action mailed Nov. 10, 2011", 12 pgs.
"U.S. Appl. No. 12/974,018, Response filed Oct. 12, 2012 to Final Office Action mailed Apr. 13, 2012", 16 pgs.
"Australian Application Serial No. 2006325787, Office Action mailed Mar. 14, 2012", 2 pgs.
"Australian Application Serial No. 2006325787, Office Action mailed Nov. 14, 2011", 2 pgs.
"Australian Application Serial No. 2006325787, Response filed May 3, 2013 to Office Action mailed Mar. 14, 2012", 10 pgs.
"Australian Application Serial No. 2006325787, Response filed Feb. 21, 2012 to Office Action mailed Nov. 14, 2011", 34 pgs.
"Chinese Application Serial No. 200680046893, Office Action mailed Aug. 3, 2012", (W/ English Translation), 8 pgs.
"Chinese Application Serial No. 200680046893, Office Action mailed Aug. 10, 2010", (W/ English Translation), 22 pgs.
"Chinese Application Serial No. 200680046893, Office Action mailed Dec. 6, 2011", (W/ English Translation), 5 pgs.
"Chinese Application Serial No. 200680046893, Response filed Jan. 23, 2012 to Office Action mailed Dec. 6, 2011", (W/ English Translation), 11 pgs.
"Chinese Application Serial No. 200680046893.7, Response filed Oct. 17, 2012 to Office Action mailed Aug. 3, 2012", (W/ English Translation), 8 pgs.
"Complaint of W. Norman Scot and Giles R. Scuderi filed Sep. 9, 2010", *W. Norman Scott and Giles R Scuderi* vs. *Zimmer, Inc and Zimmer Technology, Inc* in the US District Court of Delaware in Case No. 10-772-GMS, (Sep. 9, 2010), 24 pgs.
"International Application Serial No. PCT/EP2011/004556, International Preliminary Report on Patentability mailed Mar. 12, 2013", 9 pgs.
"International Application Serial No. PCT/EP2011/004556, International Search Report mailed Feb. 9, 2012", 6 pgs.
"International Application Serial No. PCT/EP2011/004556, Written Opinion mailed Mar. 12, 2013", 9 pgs.
"Japanese Application Serial No. 2008-545981, Examiners Decision of Final Refusal mailed Oct. 16, 2012", (W/ English Translation), 3 pgs.
"Japanese Application Serial No. 2008-545981, Office Action mailed Apr. 17, 2012", (W/ English Translation), 5 pgs.
"Japanese Application Serial No. 2008-545981, Office Action mailed Jul. 5, 2011", (W/ English Translation), 13 pgs.
"Japanese Application Serial No. 2008-545981, Response filed Oct. 5, 2011 to Office Action mailed Jul. 5, 2011", (W/ English Translation), 6 pgs.
"Japanese Application Serial No. 2008-545981, Response filed Aug. 30, 2012 to Office Action mailed Apr. 17, 2012", (W/ English Translation), 5 pgs.
"Japanese Application Serial No. 2011-221305, Office Action mailed Feb. 26, 2013", (W/ English Translation), 13 pgs.
"Japanese Application Serial No. 2011-221305, Office Action mailed Sep. 17, 2013", (W/ English Translation), 5 pgs.
"Japanese Application Serial No. 2011-221305, Response filed Aug. 26, 2013 to Office Action mailed Feb. 26, 2013", (W/ English Translation), 9 pgs.
Hitt, Kirby, et al., "Anthropometric Measurements of the Human Knee: Correlation to the Sizing of Current Knee Arthroplasty Systems", The Journal of Bone & Joint Surgery, (2003), 114-122.
Mensch, Joseph S, et al., "Knee Morphology as a Guide to Knee Replacement", Clinical Orthopaedics and Related Research No. 112, (Oct. 1975), 231-241.
Poilvache, Pascal L, et al., "Rotational Landmarks and Sizing of the Distal Femur in Total Knee Arthroplasty", Clinical Orthopaedics and Related Research, No. 331, (1996), 35-46.

Seedhom, B B, et al., "Dimensions of the Knee—Radiographic and Autopsy Study of Sizes Required for a Knee Prosthesis", Annals of the Rheumatic Diseases, (1972), 54-58.
Yoshioka, Yuki, et al., "The Anatomy and Functional Axes of the Femur", The Journal of Bone and Joint Surgery, vol. 69A, No. 6, (Jul. 1987), 873-880.
Zimmer Gender Solutions Natural-Knee Flex System Brochure, 2007, 2009, Zimmer, Inc.
Zimmer Gender Solutions Natural-Knee Flex System Surgical Technique, 2007, 2008, 2009, Zimmer, Inc.
Partial Search Report mailed Jun. 27, 2012 in International Application No. PCT/US2012/035693 from the International Searching Authority.
Partial Search Report mailed Jul. 3, 2012 in International Application No. PCT/US2012/035688 from the International Searching Authority.
"U.S. Appl. No. 11/611,021, Non Final Office Action mailed Jan. 17, 2014", 11 pgs.
"U.S. Appl. No. 12/974,018, Non Final Office Action mailed Apr. 4, 2014", 11 pgs.
"U.S. Appl. No. 13/459,061, Non Final Office Action mailed Mar. 26, 2014", 8 pgs.
"U.S. Appl. No. 13/459,061, Response filed Jan. 10, 2014 to Restriction Requirement mailed Nov. 12, 2013", 8 pgs.
"U.S. Appl. No. 13/459,061, Response filed Jun. 25, 2014 to Non Final Office Action mailed Mar. 26, 2014", 11 pgs.
"U.S. Appl. No. 13/459,064, Final Office Action mailed Jun. 13, 2014", 10 pgs.
"U.S. Appl. No. 13/459,064, Non Final Office Action mailed Mar. 6, 2014", 8 pgs.
"U.S. Appl. No. 13/459,064, Response filed Jan. 27, 2014 to Restriction Requirement mailed Nov. 25, 2013", 13 pgs.
"U.S. Appl. No. 13/459,064, Response filed Jun. 3, 2014 to Non-Final Office action dated Mar. 6, 2014", 13 pgs.
"U.S. Appl. No. 13/819,528, Response filed May 22, 2014 to Non Final Office Action mailed Dec. 6, 2013", 15 pgs.
"U.S. Appl. No. 14/014,737, Non Final Office Action mailed May 6, 2014", 6 pgs.
"U.S. Appl. No. 61/381,803, filed Sep. 10, 2010", 23 pgs.
"Australian Application Serial No. 2012271153, Amendment filed Jan. 16, 2014", 13 pgs.
"Canadian Application Serial No. 2,641,966, Office Action mailed Feb. 6, 2014", 2 pgs.
"Canadian Application Serial No. 2,641,966, Response filed Jan. 15, 2014 to Office Action mailed Jul. 16, 2013", 6 pgs.
"European Application Serial No. 06840269.2, Examination Notification Art. 94(3) mailed Jan. 24, 2014", 6 pgs.
"International Application Serial No. PCT/US2012/035688, International Preliminary Report on Patentability mailed Jan. 3, 2014", 13 pgs.
"International Application Serial No. PCT/US2012/035691, International Preliminary Report on Patentability mailed Jan. 3, 2014", 13 pgs.
"International Application Serial No. PCT/US2012/035693, International Preliminary Report on Patentability mailed Jan. 3, 2014", 13 pgs.
"International Application Serial No. PCT/US2012/038531, International Preliminary Report on Patentability mailed Jan. 3, 2014", 12 pgs.
"Japanese Application Serial No. 2011-221305, Response filed Dec. 17, 2013 to Office Action mailed Sep. 17, 2013", (W/ English Translation of Claims), 8 pgs.
"Japanese Application Serial No. 2014-515821, Request for Examination Amendment filed Apr. 8, 2014", (W/ English Translation), 18 pgs.
"U.S. Appl. No. 11/611,021, Final Office Action mailed Sep. 25, 2014", 9 pgs.
"U.S. Appl. No. 11/611,021, Preliminary Amendment filed Oct. 26, 2007", 7 pgs.
"U.S. Appl. No. 11/611,021, Response filed Jul. 15, 2014 to Non-Final Office Action dated Jan. 17, 2014", 19 pgs.
"U.S. Appl. No. 12/974,018, Final Office Action mailed Oct. 10, 2014", 12 pgs.

(56) References Cited

OTHER PUBLICATIONS

"U.S. Appl. No. 12/974,018, Response filed Jul. 30, 2014 to Non-Final Office Action mailed Apr. 4, 2014", 15 pgs.

"U.S. Appl. No. 13/459,061, Advisory Action mailed Sep. 30, 2014", 3 pgs.

"U.S. Appl. No. 13/459,061, Final Office Action mailed Jul. 23, 2014", 10 pgs.

"U.S. Appl. No. 13/459,061, Non Final Office Action mailed Nov. 10, 2014", 9 pgs.

"U.S. Appl. No. 13/459,061, Response filed Feb. 10, 2015 to Non Final Office Action mailed Nov. 10, 2014", 12 pgs.

"U.S. Appl. No. 13/459,061, Response filed Sep. 19, 2014 to Final Office Action dated Jul. 23, 2014", 9 pgs.

"U.S. Appl. No. 13/459,064, Notice of Allowance mailed Aug. 28, 2014", 8 pgs.

"U.S. Appl. No. 13/459,064, PTO Response to Rule 312 Communication mailed Dec. 15, 2014", 2 pgs.

"U.S. Appl. No. 13/459,064, Response filed Aug. 13, 2014 to Final Office Action mailed Jun. 13, 2014", 13 pgs.

"U.S. Appl. No. 13/819,528, Final Office Action mailed Feb. 5, 2015", 15 pgs.

"U.S. Appl. No. 13/819,528, Non Final Office Action mailed Aug. 12, 2014", 10 pgs.

"U.S. Appl. No. 13/819,528, Response filed Jan. 12, 2015 to Non Final Office Action mailed Aug. 12, 2014", 13 pgs.

"U.S. Appl. No. 14/014,737, Advisory Action mailed Oct. 23, 2014", 3 pgs.

"U.S. Appl. No. 14/014,737, Appeal Brief filed Feb. 12, 2015", 12 pgs.

"U.S. Appl. No. 14/014,737, Final Office Action mailed Aug. 15, 2014", 5 pgs.

"U.S. Appl. No. 14/014,737, Pre-Appeal Brief Request filed Nov. 14, 2014", 4 pgs.

"U.S. Appl. No. 14/014,737, Preliminary Amendment filed Nov. 6, 2013", 7 pgs.

"U.S. Appl. No. 14/014,737, Response filed Aug. 6, 2014 to Non-Final Office Action mailed May 6, 2014", 8 pgs.

"U.S. Appl. No. 14/014,737, Response filed Oct. 15, 2014 to Final Office Action mailed Aug. 15, 2014", 8 pgs.

"Canadian Application Serial No. 2,641,966, Office Action mailed Aug. 25, 2014", 2 pgs.

"European Application Serial No. 06840269.2, Examination Notification Art. 94(3) mailed Nov. 12, 2014", 4 pgs.

"European Application Serial No. 12720354.5, Examination Notification Art. 94(3) mailed Oct. 22, 2014", 4 pgs.

"European Application Serial No. 12722967.2, Examination Notification Art. 94(3) mailed Oct. 22, 2014", 4 pgs.

"European Application Serial No. 12724484.6, Examination Notification Art. 94(3) mailed Dec. 3, 2014", 5 pgs.

"Japanese Application Serial No. 2014-515820, Office Action mailed Dec. 2, 2014", (W/ English Translation), 8 pgs.

"Japanese Application Serial No. 2014-515831, Office Action mailed Dec. 16, 2014", (W/ English Translation), 12 pgs.

"U.S. Appl. No. 11/611,021, Non Final Office Action mailed Jun. 17, 2015", 12 pgs.

"U.S. Appl. No. 11/611,021, Response filed Feb. 24, 2015 to Final Office Action mailed Sep. 25, 2014", 16 pgs.

"U.S. Appl. No. 11/611,021, Response filed Jun. 6, 2011 Final Office Action mailed Mar. 10, 2011", 8 pgs.

"U.S. Appl. No. 12/974,018, Appeal Brief filed Feb. 20, 2015", 24 pgs.

"U.S. Appl. No. 13/459,061, Notice of Allowance mailed Feb. 27, 2015", 8 pgs.

"U.S. Appl. No. 13/819,528, Advisory Action mailed Apr. 14, 2015", 3 pgs.

"U.S. Appl. No. 13/819,528, Preliminary Amendment filed Feb. 27, 2013", 9 pgs.

"U.S. Appl. No. 13/819,528, Response filed Apr. 2, 2015 to Final Office Action mailed Feb. 5, 2015", 12 pgs.

"U.S. Appl. No. 13/819,528, Response filed Apr. 29, 2015 to Advisory Action mailed Apr. 14, 2015", 13 pgs.

"U.S. Appl. No. 13/819,528, Supplemental Preliminary Amendment filed Jul. 11, 2013", 6 pgs.

"U.S. Appl. No. 14/553,034, Preliminary Amendment filed Mar. 13, 2015", 10 pgs.

"U.S. Appl. No. 14/731,013, Supplemental Preliminary Amendment filed Jun. 18, 2015", 5 pgs.

"Australian Application Serial No. 2012271243, Subsequent Examiners Report mailed Apr. 13, 2015", 2 pgs.

"Canadian Application Serial No. 2,641,966, Response filed Feb. 25, 2015 to Office Action mailed Aug. 25, 2014", 4 pgs.

"Canadian Application Serial No. 2,641,966, Response filed Aug. 6, 2014 to Office Action mailed Feb. 6, 2014", 3 pgs.

"Chinese Application Serial No. 201280039705.3, Office Action mailed Mar. 20, 2015", (W/ English Translation), 15 pgs.

"European Application Serial No. 06840269.2, Response filed Mar. 23, 2015 to Examination Notification Art. 94(3) mailed Nov. 12, 2014", 10 pgs.

"European Application Serial No. 06840269.2, Response filed Aug. 4, 2014 to Examination Notification Art. 94(3) mailed Jan. 24, 2014", 10 pgs.

"International Application Serial No. PCT/US2006/062117, International Preliminary Report on Patentability mailed on Jun. 18, 2008", 5 pgs.

"International Application Serial No. PCT/US2006/062117, Written Opinion mailed on Apr. 5, 2007", 4 pgs.

"Japanese Application Serial No. 2014-515819, Office Action mailed Feb. 3, 2015", (W/ English Translation), 15 pgs.

* cited by examiner

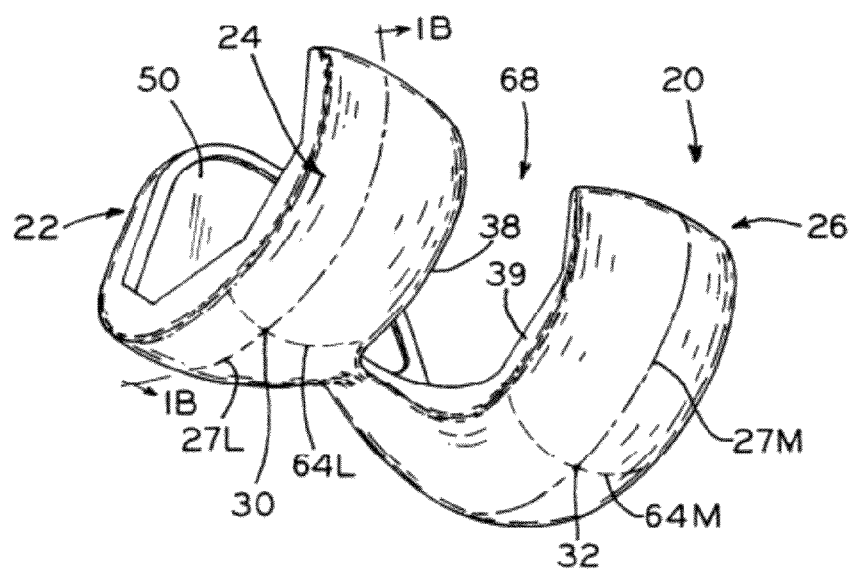
FIG_1A

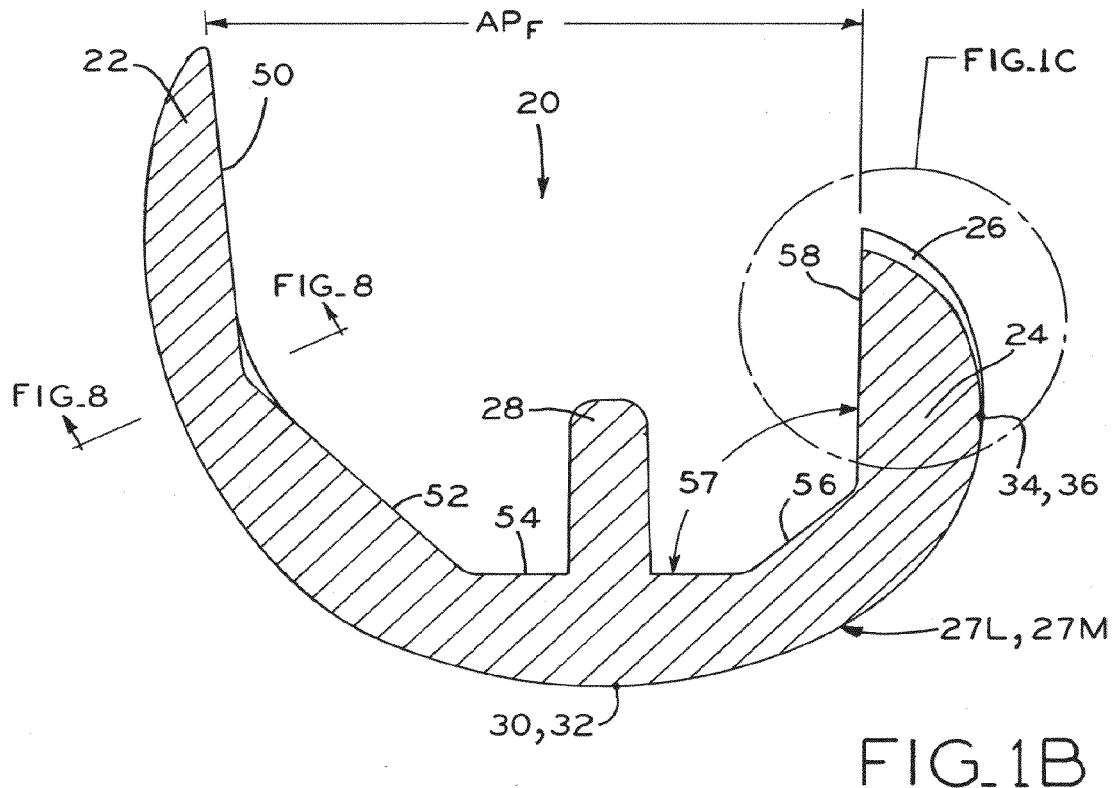
FIG_1B
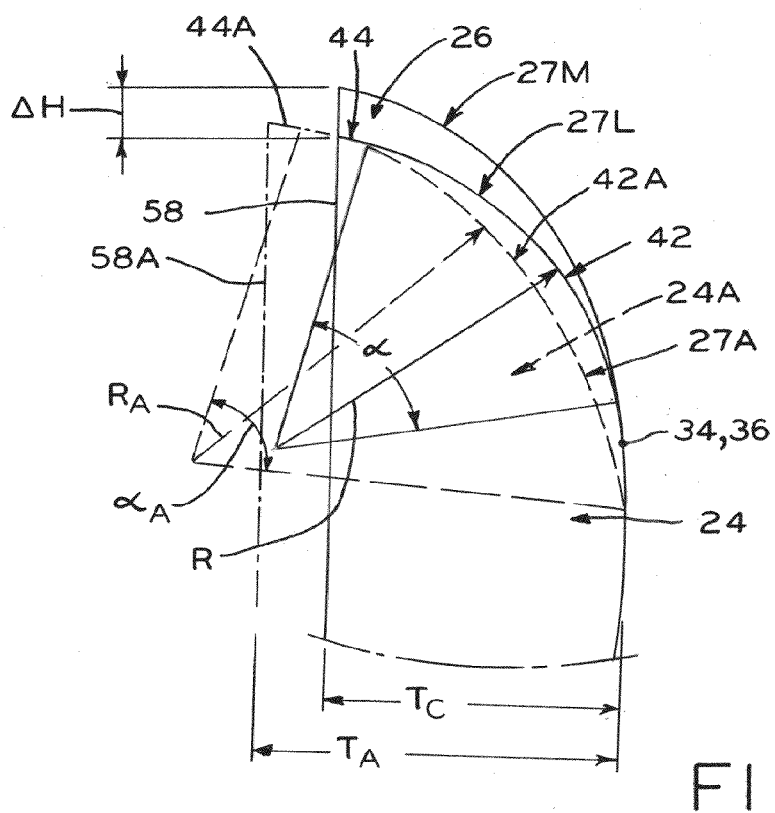
FIG_1C

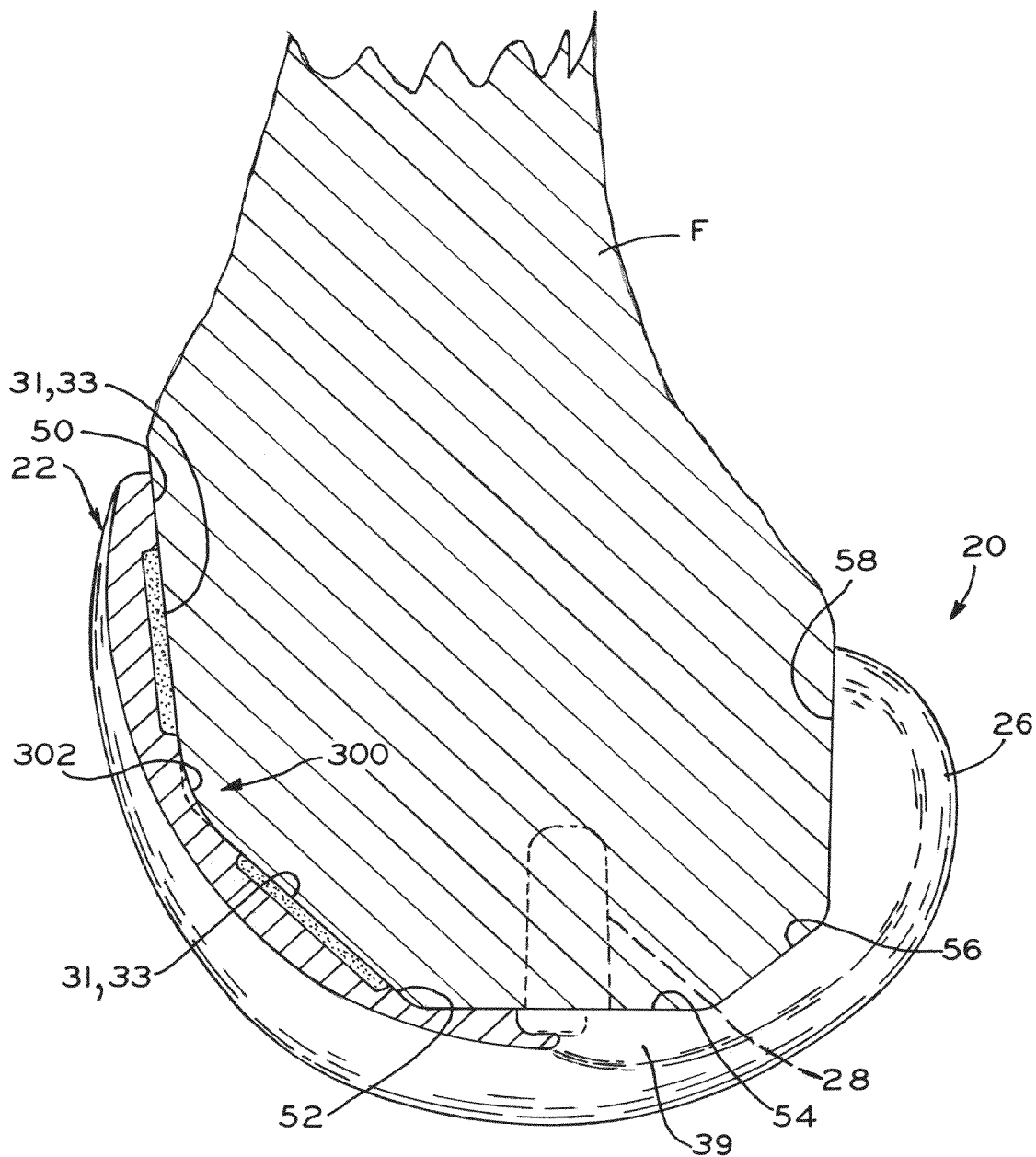
FIG_10B

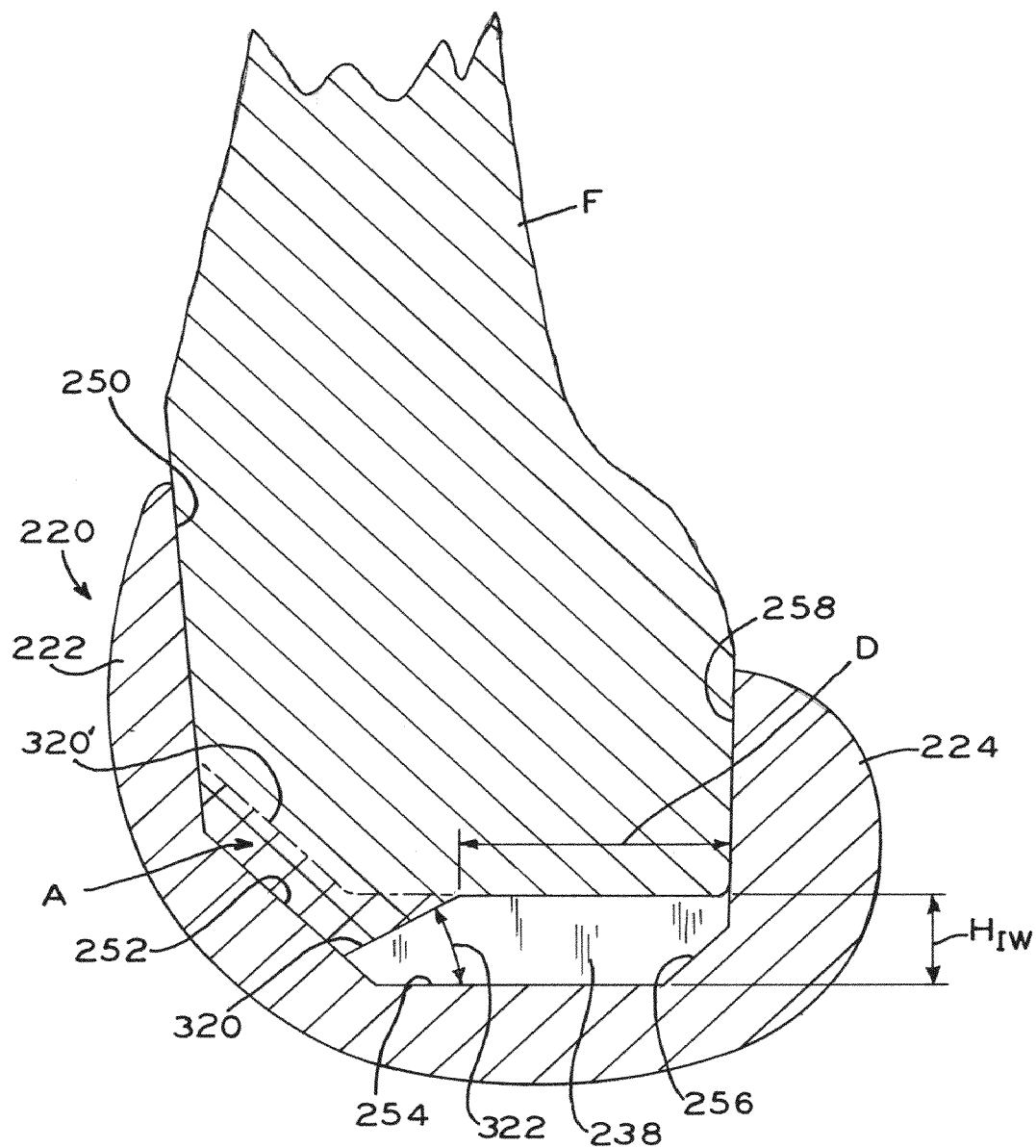
FIG_11B

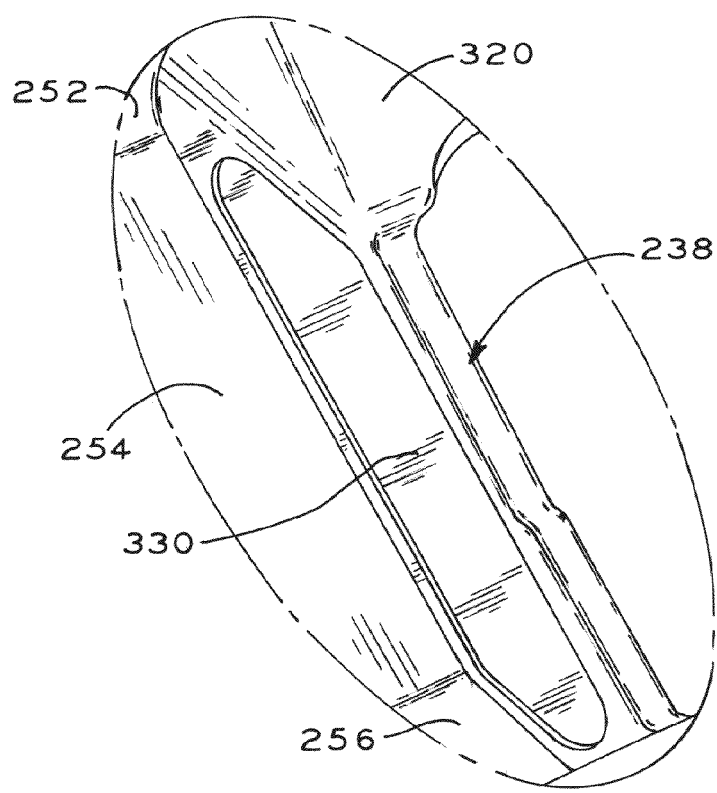
FIG_12B
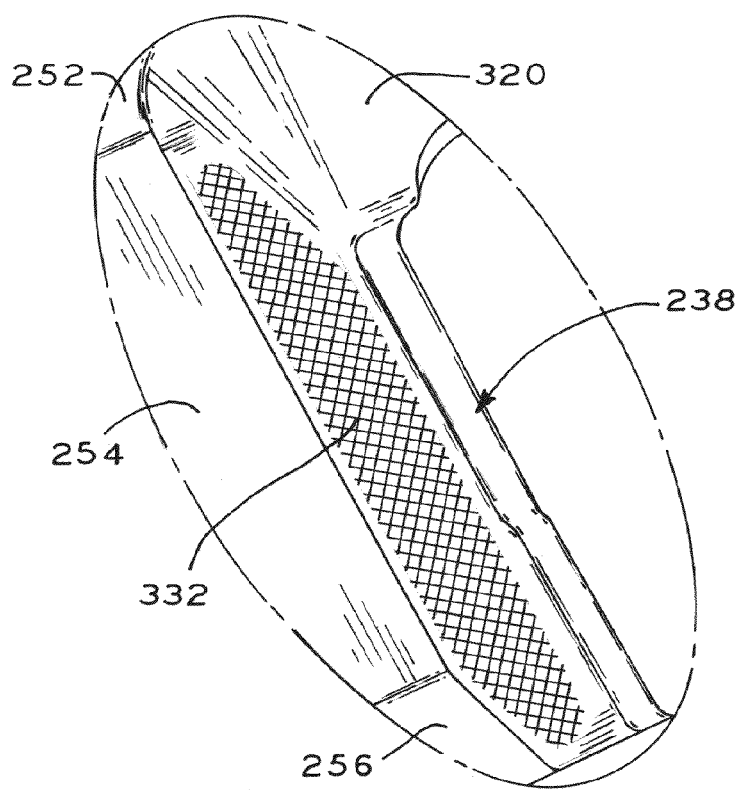
FIG_12C

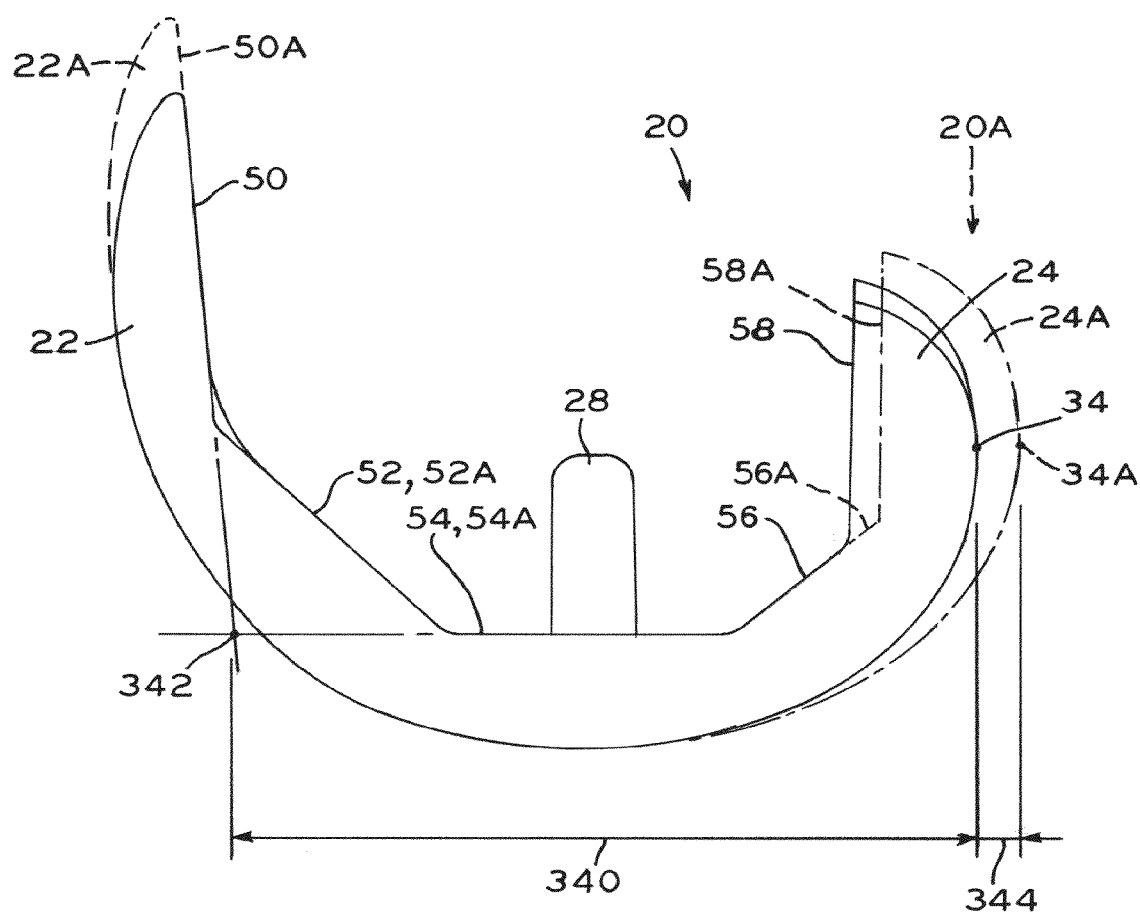
FIG_13A

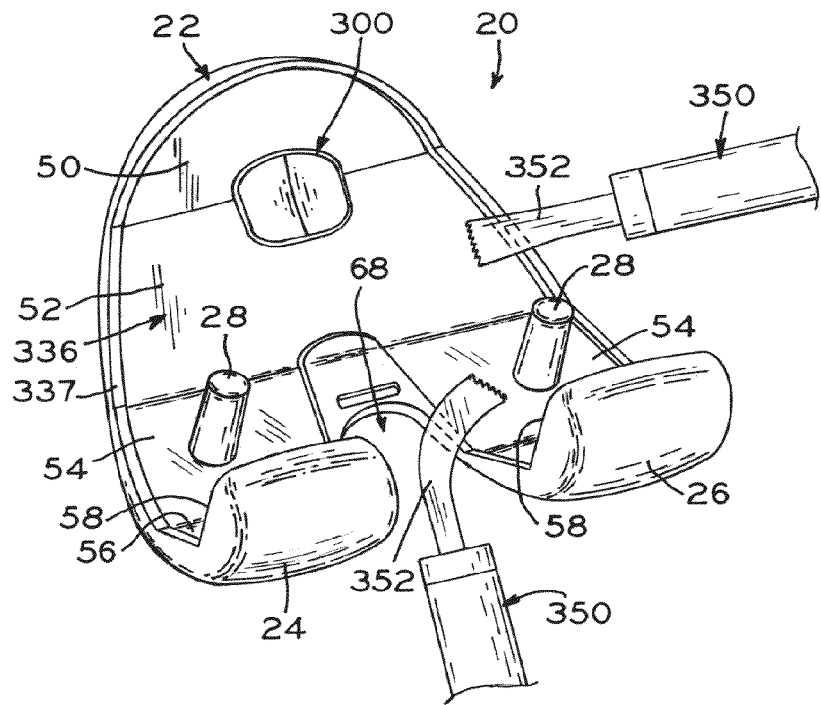
FIG_14A
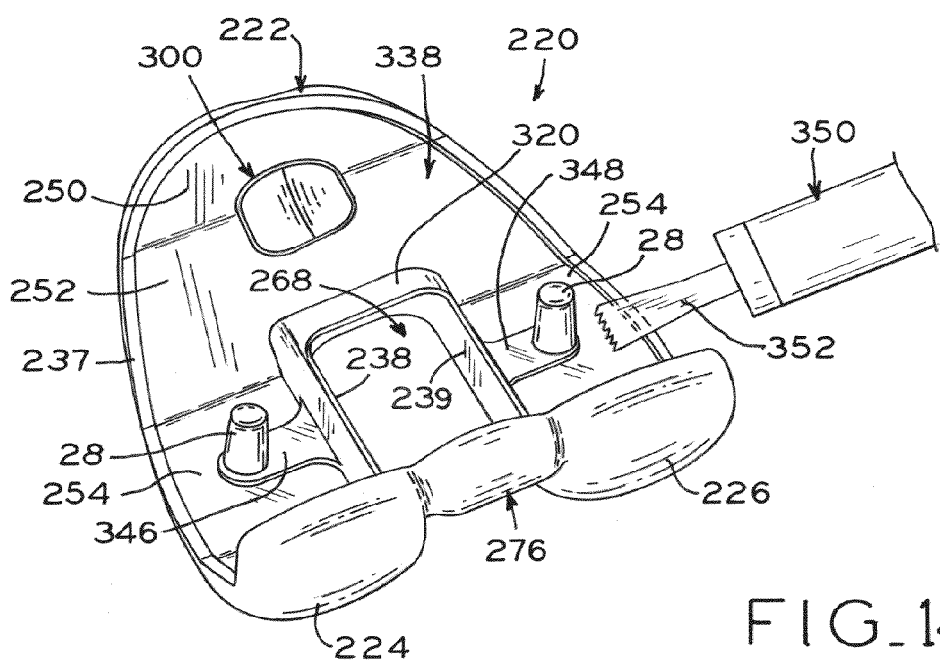
FIG_14B

FEMORAL COMPONENT FOR A KNEE PROSTHESIS WITH IMPROVED ARTICULAR CHARACTERISTICS

CROSS-REFERENCE TO RELATED APPLICATIONS

This application claims benefit under Title 35, U.S.C. §119 (e) of U.S. Provisional patent application Ser. No. 61/561,658 filed Nov. 18, 2011, U.S. Provisional Patent Application Ser. No. 61/579,873 filed Dec. 23, 2011, U.S. Provisional Patent Application Ser. No. 61/592,575 filed Jan. 30, 2012, U.S. Provisional Patent Application Ser. No. 61/594,113 filed Feb. 2, 2012, U.S. Provisional Patent Application Ser. No. 61/621,370 filed Apr. 6, 2012, U.S. Provisional Patent Application Ser. No. 61/621,372 filed Apr. 6, 2012, and U.S. Provisional Patent Application Ser. No. 61/621,373 filed Apr. 6, 2012, all of which are entitled "FEMORAL COMPONENT FOR A KNEE PROSTHESIS WITH IMPROVED ARTICULAR CHARACTERISTICS," the entire disclosures of which are hereby expressly incorporated by reference herein.

This application is a Continuation-In-Part of U.S. patent application Ser. No. 13/161,624 filed Jun. 16, 2011, entitled "FEMORAL PROSTHESIS SYSTEM," the entire disclosure of which is expressly incorporated by reference herein.

BACKGROUND

1. Technical Field

The present disclosure relates to orthopaedic prostheses and, specifically, to femoral components in a knee prosthesis.

2. Description of the Related Art

Orthopaedic prostheses are commonly utilized to repair and/or replace damaged bone and tissue in the human body. For a damaged knee, a knee prosthesis may be implanted using a tibial base plate, a tibial bearing component, and a distal femoral component. The tibial base plate is affixed to a proximal end of the patient's tibia, which is typically resected to accept the base plate. The femoral component is implanted on a distal end of the patient's femur, which is also typically resected to accept the femoral component. The tibial bearing component is placed between the tibial base plate and femoral component, and may be fixedly or slidably coupled to the tibial base plate.

The femoral component provides articular surfaces which interact with the adjacent tibial bearing component and a natural or prosthetic patella during extension and flexion of the knee. The features and geometry of the articular surfaces of the femoral component influence the articular characteristics of the knee, such as by cooperating with the tibial bearing component to define flexion range, internal/external rotation, femoral rollback and patellar tracking, for example. The non-articular, bone contacting surfaces of the femoral component define the shape and geometry of the bone resection on the distal femur, and therefore influence the amount of bone resected from the femur.

Further, the overall shape and geometry of the femoral component, particularly around its outer periphery, influences the interaction between the knee prosthesis and adjacent soft tissues remaining in place after prosthesis implantation.

Accordingly, substantial design efforts have focused on providing knee prosthesis components which preserve flexion range, promote desirable kinematic motion profiles, protect natural soft tissues, and are compatible with the widest possible range of prospective knee replacement patients.

SUMMARY

The present disclosure provides an orthopaedic knee prosthesis including a femoral component which exhibits enhanced articular features, minimizes removal of healthy bone stock from the distal femur, and minimizes the impact of the prosthesis on adjacent soft tissues of the knee.

Features which operate to enhance articulation include: 1) bulbous posterior geometry of the femoral condyles, as viewed in a sagittal cross-section (i.e., the "J-curve"), facilitates deep flexion and low component wear by reconfiguring the J-curve curvature at flexion levels above 90-degrees; 2) provision of "standard" and "narrow" femoral components which share a common bone-resection sagittal profile but define different peripheral and articular geometries designed to accommodate natural variability in patient anatomy; and 3) a lateral posterior femoral condyle which is shorter (i.e., defines a reduced proximal/distal dimension) as compared to the medial posterior condyle, thereby facilitating deep flexion and the attendant external rotation of the femur while avoiding impingement between prosthesis components.

Features which operate to minimize impact of the prosthesis on adjacent soft tissues of the knee include: 1) for posterior-stabilized (PS) designs, a femoral cam with a generally cylindrical articular surface, in which the articular surface is flanked at its medial and lateral ends by broad, large-radius convex-to-concave transitions to the adjacent medial and lateral femoral condyles, thereby ensuring a desired cam/spine articular interaction while avoiding potential soft-tissue impingement; 2) for cruciate retaining (CR) designs, an asymmetric intercondylar notch which accommodates external rotation of the femur in deep flexion while avoiding impingement between intercondylar wall surfaces and the posterior cruciate ligament; and 3) an anterior flange including a patellofemoral groove or sulcus, in which the medial and lateral surfaces near the edge of the flange define broad, large-radius convexity, thereby accommodating soft tissues in the anterior portion of the knee.

Features which allow femoral components made in accordance with the present disclosure to be implanted with minimal bone removal include: 1) an anterior bone contacting surface, opposite the patellar groove of the anterior flange, which includes an edged central peak operable to maintain a desired material thickness throughout the anterior flange while reducing the overall average thickness of the anterior flange; 2) for posterior-stabilized (PS) implant designs, an intercondylar box with sloped sidewalls which selectively reduce the proximal/distal height of portions of the sidewalls, to facilitate preservation of bone near the anterior end of the anatomic intercondylar notch; 3) for PS designs, intercondylar box sidewalls which are configured to function as a fixation lug, thereby obviating the need for fixation pegs; 4) consistently small incremental growth between respective pairs of prosthesis sizes, thereby allowing minimal bone resection for a greater majority of patients; and 5) a specially designed "pocket" on the bone contacting side of the femoral component for bone cement and/or porous bone-ingrowth material, in which the pocket maximizes long-term fixation while also facilitating potential component removal in revision surgery.

According to one embodiment thereof, the present invention provides a family of femoral components comprising a plurality of nominal femoral component sizes, each of the family of femoral components adapted to articulate with a tibial articular surface to form a knee prosthesis, each of the family of femoral components comprising: medial and lateral condyles shaped to articulate with the tibial articular surface through a range of motion, in which full extension corresponds to zero degrees flexion of the knee prosthesis and positive flexion corresponds to greater than zero degrees flexion of the knee prosthesis, the medial and lateral condyles defining medial and lateral J-curves, the medial J-curve comprising: a medial initial-flexion articular segment positioned to engage a medial compartment of the tibial articular surface from the full extension to an intermediate degree of flexion; and a medial deep-flexion articular segment positioned to engage the medial compartment from the intermediate degree of flexion to a high degree of flexion, at least part of the medial deep-flexion articular segment defining a medial deep-flexion radius swept through a medial deep-flexion angular extent to define a medial deep-flexion arc length, such that a medial bulbousness ratio is defined as the medial deep-flexion arc length divided by the medial deep-flexion angular extent, the lateral J-curve comprising: a lateral initial-flexion articular segment positioned to engage a lateral compartment of the tibial articular surface from the full extension to the intermediate degree of flexion; and a lateral deep-flexion articular segment positioned to engage the lateral compartment from the intermediate degree of flexion to the high degree of flexion, at least part of the lateral deep-flexion articular segment defining a lateral deep-flexion radius swept through a lateral deep-flexion angular extent to define a lateral deep-flexion arc length, such that a lateral bulbousness ratio is defined as the lateral deep-flexion arc length divided by the lateral deep-flexion angular extent, at least one of the medial and lateral bulbousness ratios equal to up to 0.22 mm/degree across a range of nominal component sizes within the family of femoral components, whereby the deep-flexion articular segment of at least one of the medial and lateral J-curves defines a bulbous sagittal posterior geometry for each of the family of femoral components.

According to another embodiment thereof, the present invention provides a family of posterior-stabilized femoral components comprising a plurality of nominal femoral component sizes, each of the family of femoral components adapted to articulate with a tibial bearing component to form a knee prosthesis, each of the family of femoral components comprising: medial and lateral condyles shaped to articulate with the tibial bearing component through a range of motion, in which full extension corresponds to zero degrees flexion of the knee prosthesis and positive flexion corresponds to greater than zero degrees flexion of the knee prosthesis, the medial and lateral condyles defining medial and lateral J-curves, the medial and lateral condyles comprising inwardly facing condylar walls forming an intercondylar space therebetween, the intercondylar space having a medial/lateral width; and a femoral cam spanning the intercondylar space to join the medial and lateral condyles to one another, the femoral cam sized and positioned to engage a spine of the tibial bearing component in positive flexion through at least a portion of the range of motion, the medial J-curve comprising: a medial initial-flexion articular segment positioned to engage a medial articular compartment of the tibial bearing component from the full extension to an intermediate degree of flexion; and a medial deep-flexion articular segment positioned to engage the medial articular compartment from the intermediate degree of flexion to a high degree of flexion, at least part of the medial deep-flexion articular segment defining a medial deep-flexion radius swept through a medial deep-flexion angular extent to define a medial deep-flexion arc length, such that a medial bulbousness ratio is defined as the medial deep-flexion arc length divided by the medial deep-flexion angular extent, the lateral J-curve comprising: a lateral initial-flexion articular segment positioned to engage a lateral articular compartment of the tibial bearing component from the full extension to the intermediate degree of flexion; and a lateral deep-flexion articular segment positioned to engage the lateral articular compartment from the intermediate degree of flexion to the high degree of flexion, at least part of the lateral deep-flexion articular segment defining a lateral deep-flexion radius swept through a lateral deep-flexion angular extent to define a lateral deep-flexion arc length, such that a lateral bulbousness ratio is defined as the lateral deep-flexion arc length divided by the lateral deep-flexion angular extent, at least one of the medial and lateral bulbousness ratios equal to up to 0.24 mm/degree across a range of at least three nominal component sizes within the family of femoral components, whereby the deep-flexion articular segment of at least one of the medial and lateral J-curves defines a bulbous sagittal posterior geometry for each of the family of femoral components.

According to yet another embodiment thereof, the present invention provides a family of femoral components comprising a plurality of nominal femoral component sizes, each of the family of femoral components adapted to articulate with a tibial articular surface, each of the family of femoral components comprising: medial and lateral condyles shaped to articulate with the tibial articular surface through a range of motion, in which full extension corresponds to medial and lateral distal-most points formed on the medial and lateral condyles, respectively, and 90-degrees flexion corresponds to medial and lateral posterior-most points on the medial and lateral condyles, respectively, the medial and lateral condyles defining medial and lateral J-curves, respectively, the medial condyle defining a maximum medial mid-flexion thickness, located in the region of the medial posterior-most point, up to 9 mm for each of at least three nominal sizes of the family of femoral components, the lateral condyle defining a maximum lateral mid-flexion thickness, located in the region of the lateral posterior-most point, up to 9 mm for each of at least three nominal sizes of the family of femoral components, the medial J-curve comprising: a medial initial-flexion articular segment positioned to engage a medial compartment of the tibial articular surface from the full extension to an intermediate degree of flexion, the medial initial-flexion articular segment inclusive of the medial distal-most point and the medial posterior-most point; and a medial deep-flexion articular segment positioned to engage the medial compartment from the intermediate degree of flexion to a high degree of flexion, the medial deep-flexion articular segment comprising an angular sweep of at least 80 degrees, such that the medial condyle enables articulation with the tibial articular surface to at least 130 degrees of flexion; the lateral J-curve comprising: a lateral initial-flexion articular segment positioned to engage a lateral compartment of the tibial articular surface from the full extension to the intermediate degree of flexion, the lateral initial-flexion articular segment inclusive of the lateral distal-most point and the lateral posterior-most point; and a lateral deep-flexion articular segment positioned to engage the lateral compartment from the intermediate degree of flexion to the high degree of flexion, the lateral deep-flexion articular segment comprising an angular sweep of at least 80 degrees, such that the lateral condyle enables articulation with the tibial articular surface to at least 130 degrees of flexion.

According to still another embodiment thereof, the present invention provides a family of posterior-stabilized femoral components comprising a plurality of nominal femoral component sizes, each of the family of femoral components adapted to articulate with a tibial bearing component to form a knee prosthesis, each of the family of femoral components comprising: medial and lateral condyles shaped to articulate with the tibial bearing component through a range of motion, in which full extension corresponds to medial and lateral distal-most points formed on the medial and lateral condyles, respectively, at zero degrees flexion of the knee prosthesis, and in which 90-degrees flexion corresponds to medial and lateral posterior-most points on the medial and lateral condyles, respectively, the medial and lateral condyles defining medial and lateral J-curves, respectively, the medial and lateral condyles comprising inwardly facing condylar walls forming an intercondylar space therebetween, the intercondylar space having a medial/lateral width; and a femoral cam spanning the intercondylar space to join the medial and lateral condyles to one another, the femoral cam sized and positioned to engage a spine of the tibial bearing component in positive flexion through at least a portion of the range of motion, the medial condyle defining a maximum medial mid-flexion thickness, located in the region of the medial posterior-most point, up to 10 mm for each of the plurality of nominal femoral component sizes, the lateral condyle defining a maximum lateral mid-flexion thickness, located in the region of the lateral posterior-most point, up to 10 mm for each of the plurality of nominal femoral component sizes, the medial J-curve comprising: a medial initial-flexion articular segment positioned to engage a medial articular compartment of the tibial bearing component from the full extension to an intermediate degree of flexion, the medial initial-flexion articular segment inclusive of the medial distal-most point and the medial posterior-most point; and a medial deep-flexion articular segment positioned to engage the medial articular compartment from the intermediate degree of flexion to a high degree of flexion, the medial deep-flexion articular segment comprising an angular sweep of at least 80 degrees, such that the medial condyle enables articulation with the tibial bearing component to at least 130 degrees; the lateral J-curve comprising: a lateral initial-flexion articular segment positioned to engage a lateral articular compartment of the tibial bearing component from the full extension to the intermediate degree of flexion, the lateral initial-flexion articular segment inclusive of the lateral distal-most point and the lateral posterior-most point; and a lateral deep-flexion articular segment positioned to engage the lateral articular compartment from the intermediate degree of flexion to the high degree of flexion, the lateral deep-flexion articular segment comprising an angular sweep of at least 80 degrees, such that the lateral condyle enables articulation with the tibial bearing component to at least 130 degrees.

According to still another embodiment thereof, the present invention provides a family of femoral components for a knee prosthesis, each of the family of femoral components adapted to articulate with a tibial articular surface and a patellar articular surface, each of the family of femoral components comprising: a medial condyle comprising: a medial condylar surface shaped to articulate with a medial compartment of the tibial articular surface through a range of motion in which full extension corresponds to zero degrees flexion of the knee prosthesis and positive flexion corresponds to greater than zero degrees flexion of the knee prosthesis, the medial condylar surface comprising a medial distal-most point positioned to contact the tibial articular surface at the full extension, a medial posterior-most point positioned to contact the tibial articular surface at 90-degrees flexion, and a medial proximal-most point; and a medial bone-contacting surface disposed opposite the medial condylar surface and positioned to abut a resected femur upon implantation of a respective one of the family of femoral components; a lateral condyle separated from the medial condyle by a component sagittal plane extending along an anterior/posterior direction and a proximal/distal direction, the lateral condyle comprising: a lateral condylar surface shaped to articulate with a lateral compartment of the tibial articular surface through the range of motion, the lateral condylar surface comprising a lateral distal-most point positioned to contact the tibial articular surface at the full extension, a lateral posterior-most point positioned to contact the tibial articular surface at 90-degrees flexion and a lateral proximal-most point; and a lateral bone-contacting surface disposed opposite the lateral condylar surface and positioned to abut the resected femur upon implantation of a respective one of the family of femoral components; and a patellar flange extending anteriorly from the medial and lateral condyles, the patellar flange comprising: a flange articular surface shaped to articulate with the patellar articular surface; an anterior bone-contacting surface disposed opposite the flange articular surface and positioned to abut an anterior facet of the resected femur upon implantation of a respective one of the family of femoral components; and medial and lateral flange walls extending between the flange articular surface to the anterior bone-contacting surface; each the family of femoral components comprising an outer periphery defining a plurality of peripheral characteristics, the peripheral characteristics comprising: a medial/lateral component width defined as the overall distance between the medial and lateral condyles along a medial/lateral direction normal to the component sagittal plane, a condylar height defined as the larger of a medial condyle height and a lateral condyle height, in which the medial condyle height is the distance from the medial distal-most point to the medial proximal-most point along the proximal/distal direction the lateral condyle height is the distance from the lateral distal-most point to the lateral proximal-most point along the proximal/distal direction; and a patellar flange height defined as the distance between i) an imaginary line connecting the medial and lateral distal-most points and ii) a proximal peak of the patellar flange, the patellar flange height measured along the proximal/distal direction; the family of femoral components comprising a regular femoral component and a narrow femoral component sharing a common anterior/posterior space between the anterior bone-contacting surface of the patellar flange and the medial and lateral bone-contacting surfaces of the medial and lateral condyles, respectively, whereby the family of femoral components are compatible with a common sagittal femoral resection geometry, at least one of the plurality of peripheral characteristics of the regular femoral component larger than the corresponding one of the plurality of peripheral characteristics of the narrow femoral component.

According to still another embodiment thereof, the present invention provides a family of femoral components for a knee prosthesis, each femoral component adapted to articulate with a tibial articular surface and a patellar articular surface, each the femoral component comprising: a medial condyle comprising: a medial condylar surface shaped to articulate with a medial compartment of the tibial articular surface through a range of motion in which full extension corresponds to zero degrees flexion of the knee prosthesis and positive flexion corresponds to greater than zero degrees flexion of the knee prosthesis, the medial condylar surface comprising a medial distal-most point positioned to contact the tibial articular surface at the full extension, a medial posterior-most point positioned to contact the tibial articular surface at 90-degrees flexion, and a medial proximal-most point positioned to contact the tibial articular surface at a maximum flexion; and a medial bone-contacting surface disposed opposite the medial condylar surface and positioned to abut a resected femur upon implantation of the femoral component; a lateral condyle separated from the medial condyle by a component sagittal plane extending along an anterior/posterior direction and a proximal/distal direction, the lateral condyle comprising: a lateral condylar surface shaped to articulate with a lateral compartment of the tibial articular surface through the range of motion, the lateral condylar surface comprising a lateral distal-most point positioned to contact the tibial articular surface at the full extension, a lateral posterior-most point positioned to contact the tibial articular surface at 90-degrees flexion and a lateral proximal-most point positioned to contact the tibial articular surface at the maximum flexion; and a lateral bone-contacting surface disposed opposite the lateral condylar surface and positioned to abut the resected femur upon implantation of the femoral component; and a patellar flange extending anteriorly from the medial and lateral condyles, the patellar flange comprising: a flange articular surface shaped to articulate with the patellar articular surface; an anterior bone-contacting surface disposed opposite the flange articular surface and positioned to abut an anterior facet of the resected femur upon implantation of the femoral component; and medial and lateral flange walls extending between the flange articular surface to the anterior bone-contacting surface; each the femoral component defining an outer periphery defining a plurality of peripheral characteristics, the peripheral characteristics comprising: a medial/lateral component width defined as the overall distance between the medial and lateral condyles along a medial/lateral direction normal to the component sagittal plane, a condylar height defined as the larger of a medial condyle height and a lateral condyle height, in which the medial condyle height is the distance from the medial distal-most point to the medial proximal-most point along the proximal/distal direction the lateral condyle height is the distance from the lateral distal-most point to the lateral proximal-most point along the proximal/distal direction; and a patellar flange height defined as the distance between an imaginary line connecting the medial and lateral distal-most points and a proximal peak of the patellar flange, as measured along the proximal/distal direction; the family of femoral components comprising a regular femoral component and a narrow femoral component sharing a common length of the imaginary line connecting the medial and lateral distal-most points, whereby the regular and narrow femoral components may be used interchangeably with a selected abutting tibial component at least one of the plurality of peripheral characteristics of the regular femoral component larger than the corresponding one of the plurality of peripheral characteristics of the narrow femoral component.

According to still another embodiment thereof, the present invention provides a family of femoral components for a knee prosthesis, each femoral component adapted to articulate with a tibial articular surface and a patellar articular surface, each the femoral component comprising: a medial condyle comprising: a medial condylar surface shaped to articulate with a medial compartment of the tibial articular surface through a range of motion in which full extension corresponds to zero degrees flexion of the knee prosthesis and positive flexion corresponds to greater than zero degrees flexion of the knee prosthesis, the medial condylar surface comprising a medial distal-most point positioned to contact the tibial articular surface at the full extension and a medial posterior-most point positioned to contact the tibial articular surface at 90-degrees flexion; and a medial bone-contacting surface disposed opposite the medial condylar surface and positioned to abut a resected femur upon implantation of the femoral component; a lateral condyle separated from the medial condyle by a component sagittal plane extending along an anterior/posterior direction and a proximal/distal direction, the lateral condyle comprising: a lateral condylar surface shaped to articulate with a lateral compartment of the tibial articular surface through the range of motion, the lateral condylar surface comprising a lateral distal-most point positioned to contact the tibial articular surface at the full extension and a lateral posterior-most point positioned to contact the tibial articular surface at 90-degrees flexion; and a lateral bone-contacting surface disposed opposite the lateral condylar surface and positioned to abut the resected femur upon implantation of the femoral component; and a patellar flange extending anteriorly from the medial and lateral condyles, the patellar flange comprising: a flange articular surface shaped to articulate with the patellar articular surface; an anterior bone-contacting surface disposed opposite the flange articular surface and positioned to abut an anterior facet of the resected femur upon implantation of the femoral component; and a distal bone-contacting surface extending along the anterior/posterior direction and between the anterior bone-contacting surface and the medial and lateral posterior bone-contacting surfaces, an imaginary surface intersection formed by extrapolating the distal bone-contacting surface anteriorly to intersect with a distal extrapolation of the anterior bone-contacting surface, the imaginary surface intersection defining an intersection point as viewed in the component sagittal plane, an anterior/posterior sizing extent defined as a distance, as viewed in the component sagittal plane, between the intersection point and one of the medial posterior-most point and the lateral posterior-most point, the family of femoral components comprising a plurality of nominal femoral component sizes, the anterior/posterior sizing extents of each adjacent pair of the plurality of nominal femoral component sizes differing by a common increment.

BRIEF DESCRIPTION OF THE DRAWINGS

The above mentioned and other features and advantages of this disclosure, and the manner of attaining them, will become more apparent and the invention itself will be better understood by reference to the following description of embodiments of the invention taken in conjunction with the accompanying drawings, wherein:

FIG. 1A is a bottom perspective view of a femoral component in accordance with the present disclosure;

FIG. 1B is a side, elevation cross-section view of the femoral component shown in FIG. 1A, taken along line 1B-1B;

FIG. 1C is an enlarged view of a portion of the femoral component shown in FIG. 1B, illustrating posterior condylar geometry as compared with an alternative design;

FIG. 10B is a sagittal elevation, cross-sectional view of the femoral component shown in FIG. 9A, illustrating the femoral component implanted on a femur;

FIG. 11B is a sagittal elevation, cross-sectional view of the femoral component of FIG. 11A, illustrating interaction between an intercondylar box thereof and the femur after implantation;

FIG. 12B is an enlarged view of a portion of the femoral component shown in FIG. 12A, illustrating an intercondylar box sidewall thereof;

FIG. 12C is an enlarged view of a portion of the femoral component shown in FIG. 12A, illustrating an intercondylar box sidewall thereof;

FIG. 13A is a sagittal, elevation view illustrating a pair of differently sized femoral components made in accordance with the present disclosure;

FIG. 14A is a proximal perspective view of the femoral component of FIG. 1B, illustrating osteotome access thereto; and FIG. 14B is a proximal perspective view of the femoral component shown in FIG. 5A, illustrating osteotome access thereto.

Corresponding reference characters indicate corresponding parts throughout the several views. The exemplifications set out herein illustrate exemplary embodiments of the present invention, and such exemplifications are not to be construed as limiting the scope of the invention in any manner.

DETAILED DESCRIPTION

Figure 1D:
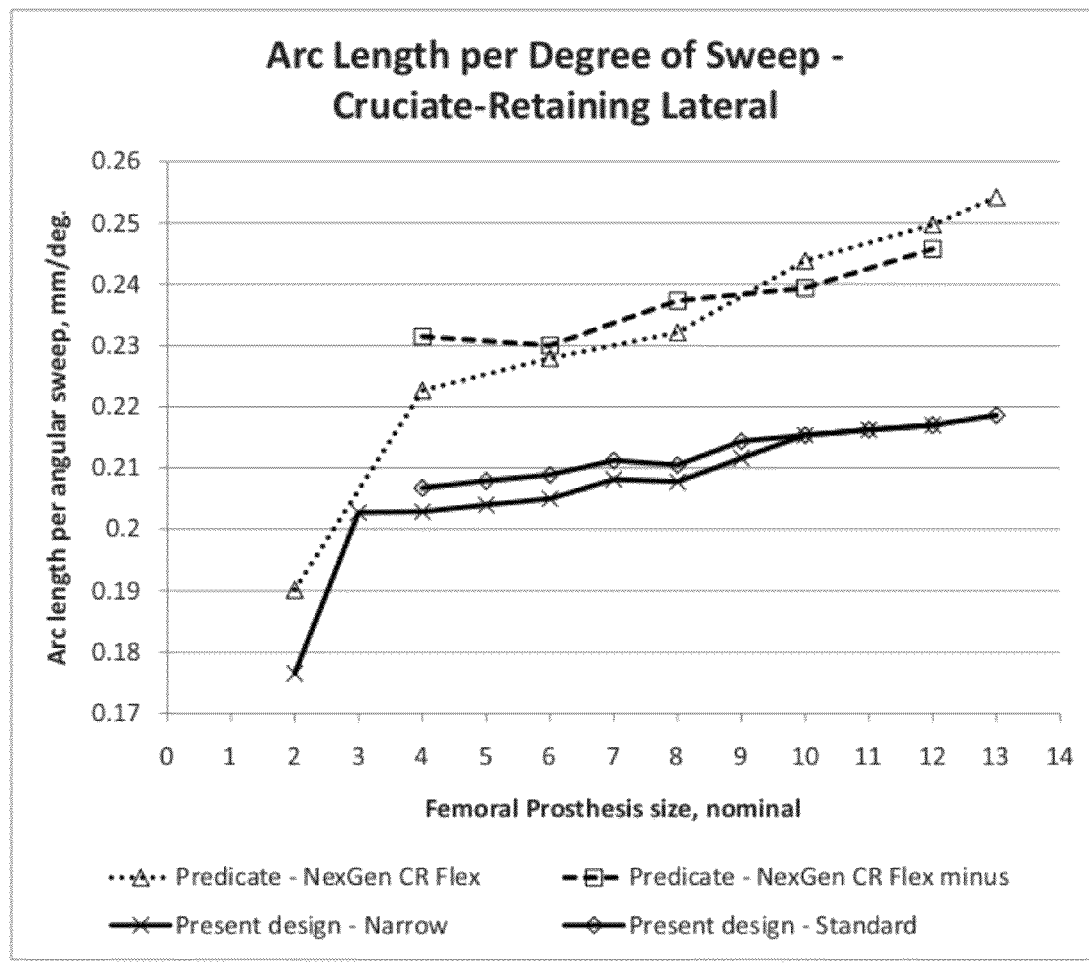
FIG. 1D is a graph plotting the arc length per degree of angular sweep for portions of lateral femoral J-curves corresponding to greater than 90-degrees of flexion, with the illustrated data pertaining to cruciate-retaining prior art femoral components (where prior art devices are listed as "predicate") and cruciate-retaining femoral components made in accordance with the present disclosure.

The present disclosure provides a femoral component for a knee prosthesis which contributes to preservation of healthy bone stock, enhanced articular characteristics, and reduced impact on soft tissues of the knee.

In order to prepare the tibia and femur for receipt of a knee joint prosthesis of the present disclosure, any suitable methods or apparatuses for preparation of the knee joint may be used. Exemplary surgical procedures and associated surgical instruments are disclosed in "Zimmer LPS-Flex Fixed Bearing Knee, Surgical Technique", "NEXGEN COMPLETE KNEE SOLUTION, Surgical Technique for the CR-Flex Fixed Bearing Knee" and "Zimmer NexGen Complete Knee Solution Extramedullary/Intramedullary Tibial Resector, Surgical Technique" (collectively, the "Zimmer Surgical Techniques"), the entire disclosures of which are hereby expressly incorporated herein by reference, copies of which are filed in an information disclosure statement on even date herewith. A surgeon first provides a prosthetic component by procuring an appropriate component (e.g., such as femoral component 20) for use in the surgical procedure, such as from a kit or operating-room container or storage receptacle. The surgeon then implants the component using suitable methods and apparatuses, such as the methods and apparatuses described in the Zimmer Surgical Techniques.

As used herein, "proximal" refers to a direction generally toward the torso of a patient, and "distal" refers to the opposite direction of proximal, i.e., away from the torso of a patient. "Anterior" refers to a direction generally toward the front of a patient or knee, and "posterior" refers to the opposite direction of anterior, i.e., toward the back of the patient or knee. In the context of a prosthesis alone, such directions correspond to the orientation of the prosthesis after implantation, such that a proximal portion of the prosthesis is that portion which will ordinarily be closest to the torso of the patient, the anterior portion closest to the front of the patient's knee, etc.

Similarly, knee prostheses in accordance with the present disclosure may be referred to in the context of a coordinate system including transverse, coronal and sagittal planes of the component. Upon implantation of the prosthesis and with a patient in a standing position, a transverse plane of the knee prosthesis is generally parallel to an anatomic transverse plane, i.e., the transverse plane of the knee prosthesis is inclusive of imaginary vectors extending along medial/lateral and anterior/posterior directions. However, it is contemplated that in some instances the bearing component transverse plane will be slightly angled with respect to the anatomic transverse plane, depending, e.g., on the particular surgical implantation technique employed by the surgeon.

Coronal and sagittal planes of the knee prosthesis are also generally parallel to the coronal and sagittal anatomic planes in a similar fashion. Thus, a coronal plane of the prosthesis is inclusive of vectors extending along proximal/distal and medial/lateral directions, and a sagittal plane is inclusive of vectors extending along anterior/posterior and proximal/distal directions. As with the relationship between the anatomic and bearing component transverse planes discussed above, it is appreciated that small angles may be formed between the bearing component sagittal and coronal planes and the corresponding anatomic sagittal and coronal planes depending upon the surgical implantation method.

As with anatomic planes, the sagittal, coronal and transverse planes defined by the knee prosthesis are mutually perpendicular to one another. For purposes of the present disclosure, reference to sagittal, coronal and transverse planes is with respect to the present knee prosthesis unless otherwise specified.

In the context of the femoral component in some knee prostheses, a sagittal plane may be a plane this is equidistant from intercondylar walls bounding the intercondylar gap formed by the component condyles. For example, referring to FIG. 5A, femoral component 220 defines intercondylar notch or gap 268 formed between lateral and medial intercondylar walls 238, 239 (FIG. 5C). In this context of component 220, a sagittal plane may the plane which bisects intercondylar gap 268 and is equidistant from intercondylar walls 238, 239.

Where the sagittal plane discussed above forms the basis for the component coordinate system, a coronal plane would be defined as a plane perpendicular to the sagittal plane and extending along the same proximal/distal direction as the sagittal plane. A transverse plane is the plane perpendicular to both the sagittal and coronal planes.

In other instances, it may be appropriate to define transverse plane as the plane perpendicular to one or both of distal most points 30, 32 (FIG. 1B) defined by lateral and medial condyles 24, 26. Generally speaking, the "distal-most points" of a femoral component of a knee prosthesis are those points which make the distal-most contact with the corresponding tibial bearing component or natural tibial articular surface when the knee is fully extended. Similarly, the "posterior-most points" of a femoral component of a knee prosthesis are those points which make contact with the corresponding tibial bearing component when the knee is at 90-degrees flexion, i.e., when the anatomic femoral and tibial axes form an angle of 90 degrees.

In the illustrative embodiment of FIG. 1A, lateral and medial condyles 24, 26 each define bearing surfaces that are three-dimensionally convex at distal-most points 30, 32. Stated another way, the lateral and medial articular bearing surfaces have no planar portions at distal-most points 30, 32. Recognizing that a three-dimensionally convex surface can define only one tangent plane at a particular point, the transverse plane of femoral component 20 may be defined as the plane tangent to one or both of distal-most points 30, 32. For many femoral components, transverse planes tangent to each of distal-most points 30, 32, are coplanar or nearly coplanar, such that a selection of either of distal-most points 30, 32 is suitable as a reference point for definition of the component transverse plane.

Where the above-described transverse plane is the basis for the component coordinate system, a coronal plane may be defined as being perpendicular to the transverse plane and extending along the same medial/lateral direction as the transverse plane. Alternatively, the coronal plane may be defined as a plane tangent to one or both of posterior-most points 34, 36 in similar fashion to the tangency of the transverse plane to distal-most points 30, 32 as discussed above. In either instance, the sagittal plane can then be defined as a plane perpendicular to the coronal and transverse planes.

Practically speaking, femoral prostheses are sold with a particular surgical procedure envisioned for component implantation. Depending on the particular geometry and accompanying surgical procedure, a person having ordinary skill in the art of orthopaedic prostheses will be able to define "distal-most points" of a femoral prosthesis component, and will be able to identify the sagittal, coronal and transverse component coordinate planes based on their relationship to the corresponding anatomic planes upon implantation.

The embodiments shown and described herein illustrate components for a left knee prosthesis. Right and left knee prosthesis configurations are mirror images of one another about a sagittal plane. Thus, it will be appreciated that the aspects of the prosthesis described herein are equally applicable to a left or right knee configuration.

Prosthesis designs in accordance with the present disclosure may include posterior stabilized (PS) prostheses and mid level constraint (MLC) prostheses, each of which includes spine 278 (FIG. 6) on the tibial bearing component and femoral cam 276 (FIG. 5A) on the femoral component. Spine 278 and cam 276 are designed to cooperate with one another to stabilize femoral component 220 with respect to tibial bearing component 240 in lieu of a resected posterior cruciate ligament (PCL).

Figure 2A:
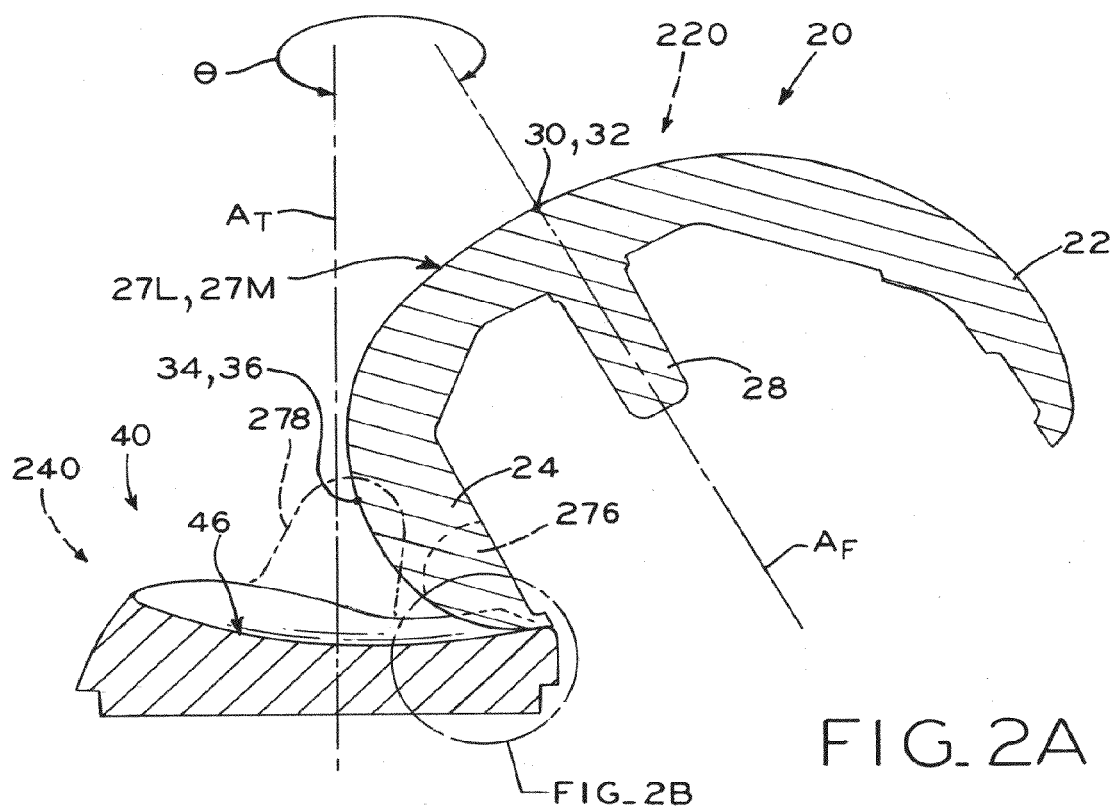
FIG. 2A is a side elevation, cross-sectional view of the femoral component shown in FIG. 1B, in which the femoral component is articulating with a tibial bearing component made in accordance with the present disclosure.

Another contemplated design includes "cruciate retaining" (CR) prostheses, such as those using components configured as shown in FIGS. 1A, 2A (shown by solid lines) and 4. CR designs omit spine 278 from the tibial bearing component and femoral cam 276 from the femoral component (e.g., FIG. 9A), such that cruciate-retaining femoral component 20 defines an intercondylar space between lateral and medial condyles 24, 26 that is entirely open and uninterrupted by femoral cam 276. CR tibial components are generally used in surgical procedures which retain the PCL.

Figure 9A:
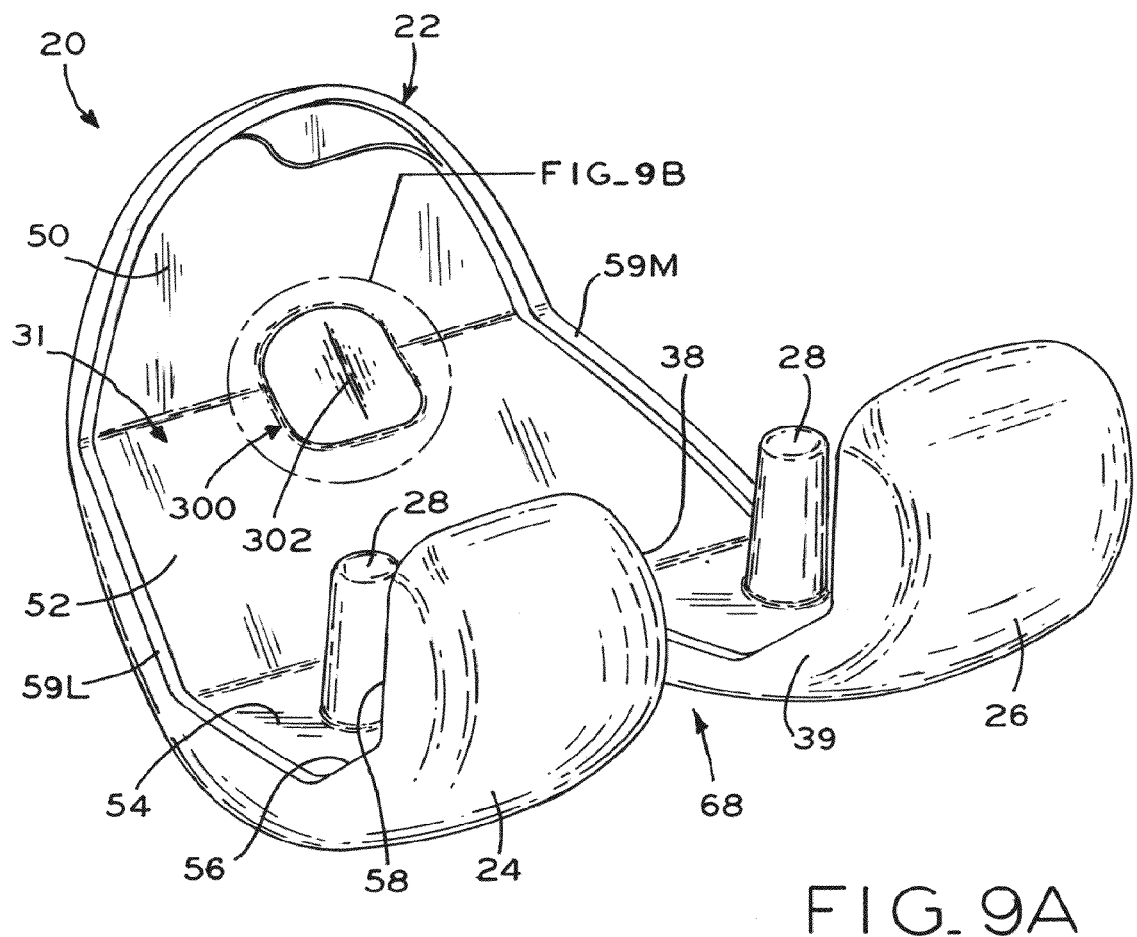
FIG. 9A is a perspective view of the femoral component shown in FIG. 1B.

Yet another design includes "ultra congruent" (UC) prostheses, which may use a femoral component lacking femoral cam 276, and may be similar or identical to the femoral component used in a CR prosthesis (i.e., femoral component 20 shown in FIG. 9A). Like CR prostheses, UC prostheses also omit spine 278 (e.g., the solid-line embodiment of FIG. 2A). However, UC prostheses are designed for use with a patient whose PCL is resected during the knee replacement surgery. "Congruence," in the context of knee prostheses, refers to the similarity of curvature between the convex femoral condyles and the correspondingly concave tibial articular compartments. UC designs utilize very high congruence between the tibial bearing compartments and femoral condyles to provide prosthesis stability, particularly with respect to anterior/posterior relative motion.

Except as otherwise specified herein, all features described below may be used with any potential prosthesis design. While a particular design may include all the features described herein, it is contemplated that some prostheses may omit some features described herein, as required or desired for a particular application.

1. Articular Features: Bulbous Sagittal Posterior Geometry.

Figure 4:
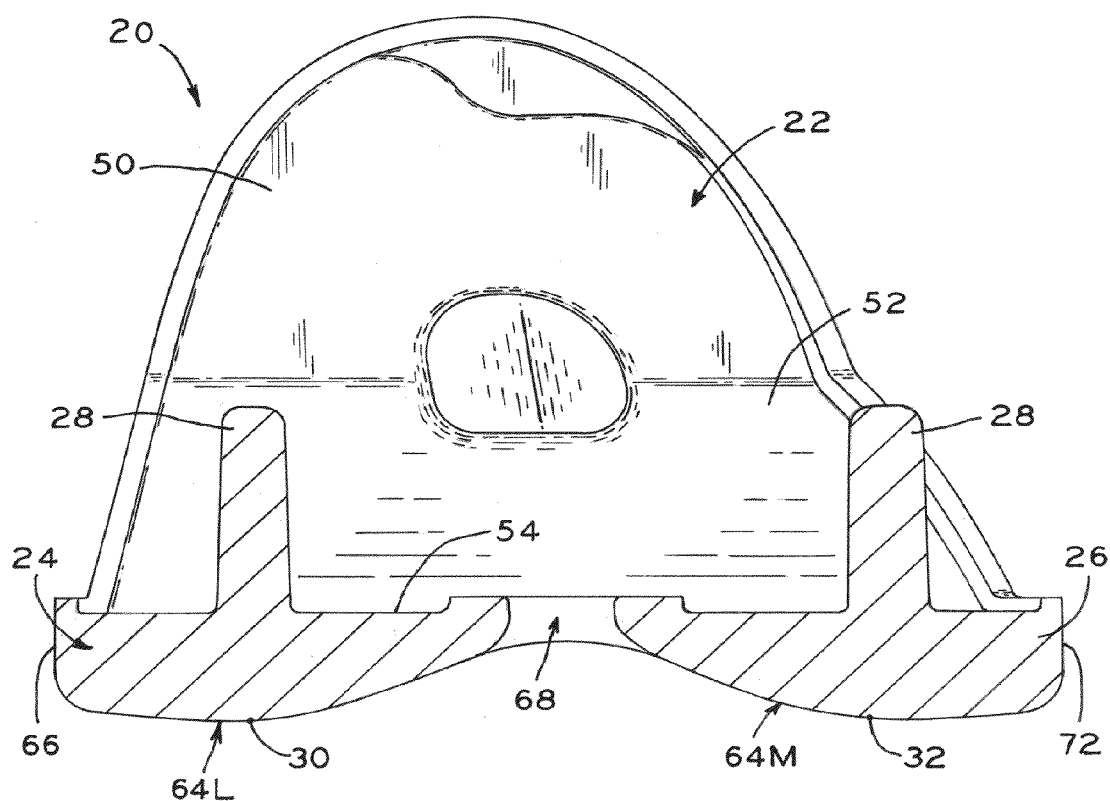
FIG. 4 is a posterior elevation, cross-sectional view of the femoral component shown in FIG. 1B, illustrating the coronal articular profile of the femoral condyles.

Referring to FIG. 1B, femoral component 20 includes anterior flange 22, lateral condyle 24 and opposing medial condyle 26, and fixation pegs 28. Lateral and medial condyles 24, 26 define articular surfaces which extend from respective lateral and medial distal-most contact points 30, 32 (FIG. 4), through respective lateral and medial posterior-most contact points 34, 36 (FIG. 7) and terminate at respective deep flexion contact areas as described in detail below. The articular surfaces are rounded and convex in shape, and sized and shaped to articulate with a tibial articular surface through a full range of motion from full extension of the knee (i.e., zero degrees flexion) through mid-flexion and deep-flexion. In an exemplary embodiment, such tibial articular surfaces are correspondingly concave dished surfaces of a prosthetic tibial component (e.g., tibial bearing component 240 of FIG. 6). However, it is appreciated that in some instances the tibial articular surface may be the natural articular compartments of a patient's tibia.

Distal-most contact points 30, 32 contact a tibial bearing component of the knee prosthesis (such as tibial bearing component 40 shown in FIG. 2A) when the knee prosthesis is at zero degrees of flexion, i.e., when the knee is fully extended, as noted above. As the knee is flexed from full extension, the lateral and medial contact points between femoral component 20 and the adjacent tibial articular surface shift posteriorly and proximally into an initial-flexion segment along medial and lateral J-curves 27M, 27L (FIG. 1A), passing through intermediate levels of flexion to eventually reach posterior most contact points 34, 36 at 90 degrees flexion. Further flexion transitions such contact points further proximally, and also anteriorly (i.e., toward anterior flange 22) into a deep-flexion segment of J-curves 27M, 27L.

For convenience, the present discussion refers to "points" or "lines" of contact between tibial bearing component 40 and femoral component 20. However, it is of course appreciated that each potential point or line of contact is not truly a point or line, but rather an area of contact. These areas of contact may be relatively larger or smaller depending on various factors, such as prosthesis materials, the amount of pressure applied at the interface between tibial bearing component 40 and femoral component 20, and the like. In an exemplary embodiment, for example, tibial bearing component 40 is made of a polymeric material such as polyethylene, while femoral component 20 is made of a metallic material such as cobalt-chrome-molybdenum (CoCrMo).

Moreover, it is appreciated that some of the factors affecting the size of the contact area may change dynamically during prosthesis use, such as the amount of applied pressure at the femoral/tibial interface during walking, climbing stairs or crouching, for example. For purposes of the present discussion, a "contact point" may be taken as the point at the geometric center of the area of contact. The "geometric center", in turn, refers to the intersection of all straight lines that divide a given area into two parts of equal moment about each respective line. Stated another way, a geometric center may be said to be the "average" (i.e., arithmetic mean) of all points of the given area. Similarly, a "contact line" is the central line of contact passing through and bisecting an elongate area of contact.

Taken from the sagittal perspective (FIG. 1B), anterior flange 22 and condyles 24, 26 cooperate to define an overall U-shaped profile of femoral component 20. The articular surface of femoral component 20, along the outer surface of this U-shaped profile, defines medial and lateral J-curves 27M, 27L respectively (FIG. 1A). More specifically, the articular surface of lateral condyle 24 cooperates with the articular surface of anterior flange 22 to define lateral J-curve 27L, which is inclusive of distal-most contact point 30 and posterior-most contact point 34. Similarly, medial J-curve 27M is defined by the articular surfaces of anterior flange 22 and medial condyle 26, taken in a sagittal cross-section and inclusive of distal-most contact point 32 and posterior-most contact point 36.

Where J-curves 27L, 27M define the sagittal articular profile of femoral component 20, coronal curves 64L, 64M define the corresponding coronal articular profile. Lateral coronal curve 64L extends along a generally medial/lateral direction, passing through lateral distal-most contact point 30 perpendicular to J-curve 27L. Similarly, medial coronal curve 64M extends along a generally medial/lateral direction, passing through medial distal-most contact point 32 perpendicular to J-curve 27M. The articular surfaces of lateral and medial condyles 24, 26 may be defined or "built" by sweeping coronal curves 64L, 64M along J-curves 27L, 27M respectively to produce convex three-dimensional articular surfaces generally corresponding with the shape of the natural femoral condyles. The specific curvatures of coronal curves 64L, 64M may vary over the extent of J-curves 27L, 27M, such as by having a generally larger radius at distal-most points 30, 32 as compared to posterior-most points 34, 36. It is contemplated that coronal curves 64L, 64M may have a variety of particular geometrical arrangements as required or desired for a particular application.

The portions of J-curves 27L, 27M which articulate with lateral and medial articular compartments 46, 48 (FIG. 6) of tibial bearing component 40 extend from approximately distal-most points 30, 32, through posterior-most contact points 34, 36 and into the portion of J-curves 27L, 27M including bulbous profile 42, shown in FIG. 1C. Stated another way, the condylar articular portions of J-curves 27L, 27M are a collection of the contact points between femoral condyles 24, 26 and tibial articular compartments 46, 48 respectively. The J-curve geometry illustrated in FIG. 1C is common to both lateral condyle 24 and medial condyle 26. For clarity, however, such geometry is described herein only with respect to lateral condyle 24.

Condyle 24A of a predicate design is shown schematically in FIG. 1C as dashed lines, while condyle 24 of femoral component 20 is shown in solid lines. As compared with condyle 24A, condyle 24 defines bulbous profile 42 in the portion of lateral J-curve 27L of condyle 24 corresponding to greater than 90 degrees of prosthesis flexion. Medial J-curve 27M of medial condyle 26 (shown behind lateral condyle 24 in FIG. 1B and extending further proximally, as described in detail below) also defines a similar bulbous geometry in the portion of J-curve 27M corresponding to greater than 90 degrees flexion. For simplicity, the bulbous condylar geometry of condyles 24, 26 is described with reference to lateral condyle 24 only.

As illustrated, bulbous profile 42 extends further posteriorly and proximally than the corresponding predicate profile 42A. This bulbous geometry arises from a reduction in the average magnitude of radius R defined throughout angular sweep a of profile 42, such that radius R is less than the corresponding average magnitude of radius $R_A$ of profile 42A through angular sweep $\alpha_A$. It is contemplated that one or more radii may be defined through angular sweeps $\alpha$, $\alpha_A$. Comparisons of the average radii, rather than individual radius values, are appropriate where multiple different radii cooperate to form profile 42 of J-curve 27L and/or the corresponding predicate profile 42A. For example, in certain exemplary embodiments femoral component 20 may define an average radius R of 10 mm while the average magnitude of radius $R_A$ may be 10.8 mm over a similar angular sweep. As described in detail below, the resulting bulbous overall arrangement of profile 42 advantageously influences the articular characteristics of femoral component 20 in deep flexion while minimizing bone resection.

Prior art devices relevant to deep-flexion bulbous sagittal geometry include the femoral components of the NexGen CR Flex prosthesis system and the femoral components NexGen LPS Flex prosthesis system, all available from Zimmer, Inc. of Warsaw, Ind. The prior art Zimmer NexGen CR Flex prosthesis system is depicted in "NEXGEN COMPLETE KNEE SOLUTION, Surgical Technique for the CR-Flex Fixed Bearing Knee," incorporated by reference above. The prior art Zimmer NexGen LPS Flex prosthesis system is depicted in "Zimmer LPS-Flex Fixed Bearing Knee, Surgical Technique," also incorporated by reference above.

As noted above, radii R are swept through angular extents $\alpha$, $\alpha_A$. Angular extents $\alpha$, $\alpha_A$ begins in the area of posterior most point 34, such as within 10 degrees of posterior-most point 34, and ends at or near the proximal-most point of the articular surface of lateral condyle 24. Referring to FIG. 1C, this proximal-most point of the articular surface is at the intersection between the end of J-curve 27L and posterior bone-contacting surface 58. It is contemplated that terminal profile 44 may be disposed between the proximal end of bulbous profile 42 and posterior bone contacting surface 58 (As shown in FIG. 1C). If included, terminal profile 44 is a nearly flat or very large-radius nonarticular portion of condyle 24 which bridges the gap between bulbous profile 42 and posterior bone contacting surface 58. In an exemplary embodiment, however, bulbous profiles 42 extend all the way to posterior bone-contacting surface 58. Further, this exemplary femoral component 20 has a substantially planar bone-contacting surface 58 which forms obtuse angle 57 with distal bone-contacting surface 54. Anterior bone-contacting surface 50 also diverges proximally from posterior bone-contacting surface 58 in the sagittal perspective, such that femoral component 20 is implantable onto a resected distal femur along a distal-to-proximal direction.

In the illustrated embodiment, the proximal terminus of angular extent a (i.e., the deepest-flexion portion of bulbous profile 42) corresponds with up to 170 degrees of knee flexion. Because femoral component 20 facilitates this high level flexion of the knee, component 20 may be referred to as a "high flexion" type component, though it is appreciated that any component which enables flexion of at least 130 degrees would also be considered "high flexion." In exemplary embodiments, a high-flexion knee prosthesis may enable a flexion range of as little as 130 degrees, 135 degrees, or 140 degrees and as large as 150 degrees, 155 degrees or 170 degrees, or may enable any level of flexion within any range defined by any of the foregoing values.

Figure 2B:
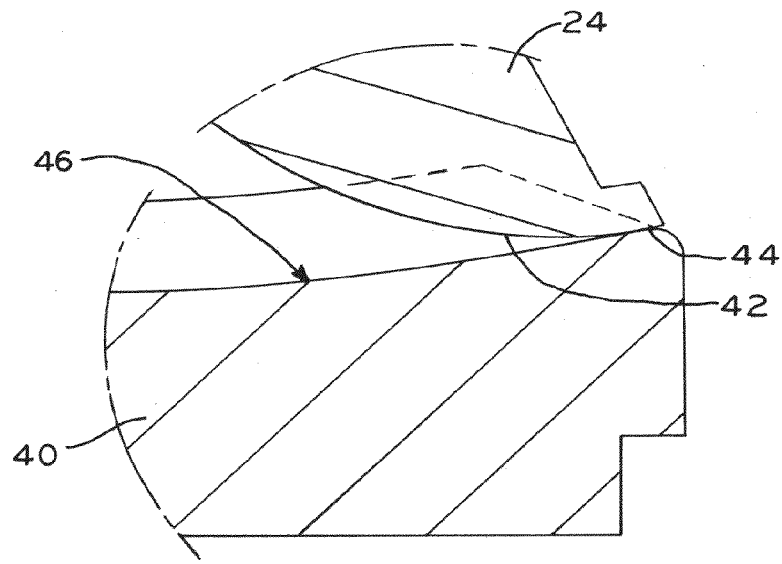
FIG. 2B is an enlarged view of a portion of the femoral component and tibial bearing component shown in FIG. 2A, illustrating a deep-flexion contact point therebetween.

For example, as illustrated in FIGS. 2A and 2B, femoral component 20 is illustrated in a deep flexion orientation, i.e., an orientation in which flexion angle θ between longitudinal tibial axis $A_T$ and longitudinal femoral axis $A_F$ is between 130 degrees and 170 degrees. As best shown in FIG. 2B, bulbous profile 42 remains in firm contact with lateral articular compartment 46 of tibial bearing component 40 at this deep flexion configuration, thereby establishing femoral component 20 as a component which is deep flexion enabling. As described in detail below, femoral component 20 accomplishes this high-flexion facilitation with a reduced condyle thickness as compared to prior art high-flexion type components.

Determination of whether the sagittal profiles 42, 42A are relatively more or less "bulbous" within the meaning of the present disclosure can be accomplished by a comparison of radii R, $R_A$ as described above. However, because angular sweeps $\alpha$, $\alpha_A$ may differ, a suitable comparative quantity may be the amount of arc length per degree of angular sweep referred to herein as the "bulbousness ratio." A more bulbous geometry, (i.e., one having a smaller average radius) defines a shorter arc length per degree of sweep as compared to a comparable less-bulbous geometry. That is to say, a lower bulbousness ratio value corresponds to a more bulbous sagittal geometry across a given angular sweep. Given the direct correspondence between bulbousness and radius, a relatively smaller average radius (i.e., radius R as compared to radius $R_A$, as shown in FIG. 1C) yields a correspondingly smaller bulbousness ratio across a comparable angular sweep.

Turning now to FIG. 1D, a comparison of bulbousness ratios defined by profiles 42, 42A are shown across multiple families of femoral components having various prosthesis sizes for lateral condyles 24 and 24A in each family. For purposes of the bulbousness comparisons discussed herein, angular sweeps $\alpha$, $\alpha_A$ (FIG. 1C) are taken from posterior-most points 34, 36, (i.e., at 90-degrees flexion) through the end of the corresponding J-curve (i.e., at the intersection between J-curves 27L, 27M, 27A and posterior bone-contacting surface 58, 58A respectively).

As illustrated in FIG. 1D, a dotted-line data set illustrates that the lateral condyles of the femoral components of the prior art Zimmer NexGen CR Flex prosthesis system define a bulbousness ratio of between 0.190 mm/degree (for the smallest nominal size) and 0.254 mm/degree (for the largest nominal size), while the dashed-line data set illustrates an alternative subset of lateral condyles within the prior art Zimmer NexGen CR Flex prosthesis system defining a bulbousness ratio of between 0.231 mm/degree and 0.246 mm/degree across a range of sizes. As shown in FIG. 1D, the family of femoral components made in accordance with the present disclosure can include at least four nominal component sizes and define a bulbousness ratio of between 0.177 mm/degree (for the smallest nominal size) and 0.219 mm/degree (for the largest nominal size), with each comparable size of the present components having a bulbousness ratio below the comparable size of the prior art devices (as shown).

For purposes of the present disclosure, anteroposterior sizing extent 340 (FIG. 13A) can be considered a proxy for nominal sizes of the present femoral component and prior art devices. Anteroposterior sizing extent 340 may also be referred to the "functional" anterior/posterior extent of femoral component 20, because extent 340 traverses the portion of femoral component 20 which is most relevant to tibiofemoral articulation (and excludes the articular portions of anterior flange 22, which is relevant to patellofemoral articulation). More information regarding specific, enumerated definitions of nominal sizes is provided in FIG. 13B, a detailed discussion of which appears below.

Figure 1E:
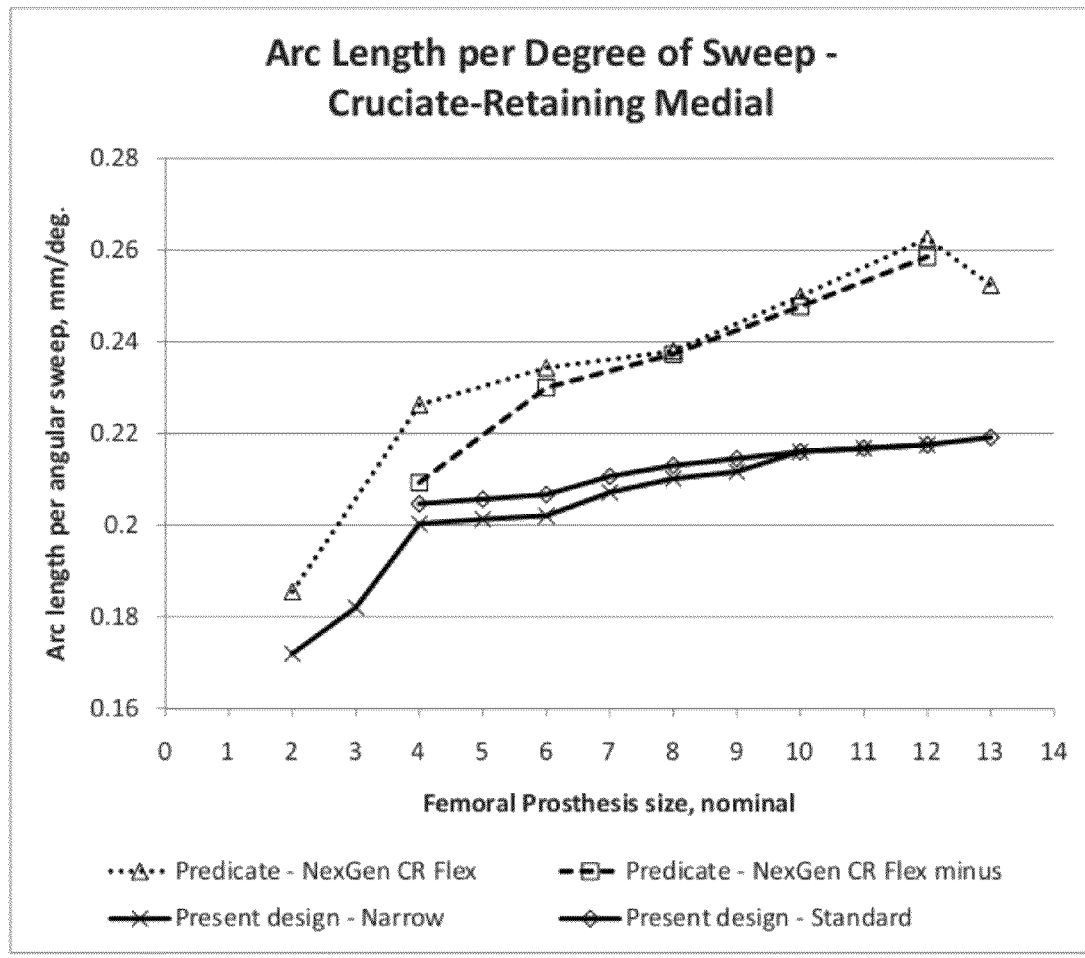
FIG. 1E is a graph plotting the arc length per degree of angular sweep for portions of medial femoral J-curves corresponding to greater than 90-degrees of flexion, with the illustrated data pertaining to cruciate-retaining prior art femoral components (where prior art devices are listed as "predicate") and cruciate-retaining femoral components made in accordance with the present disclosure.

Similar to the lateral condylar bulbousness illustrated in FIG. 1D, FIG. 1E illustrates a comparison of bulbousness ratios defined by the portions of medial J-curves 27M corresponding to greater than 90 degrees of prosthesis flexion, shown across various prosthesis sizes in a family of femoral components as compared to prior art devices. As illustrated, a dotted-line data set illustrates that the medial condyles of the femoral components of the prior art Zimmer NexGen CR Flex prosthesis system define a bulbousness ratio of between 0.185 mm/degree (for the smallest nominal size) and 0.252 mm/degree (for the largest nominal size), while the dashed-line data set illustrates the above-mentioned alternative subset of medial condyles within the prior art Zimmer NexGen CR Flex prosthesis system defining a bulbousness ratio of between 0.209 mm/degree and 0.259 mm/degree across the same range of sizes depicted in FIG. 1D. As shown in FIG. 1E, the family of femoral components made in accordance with the present disclosure can include at least four nominal component sizes and define a bulbousness ratio of between 0.172 mm/degree (for the smallest nominal size) and 0.219 mm/degree (for the largest nominal size), with each comparable size of the present components having a bulbousness ratio below the comparable size of the prior art devices (as shown).

Figure 1F:
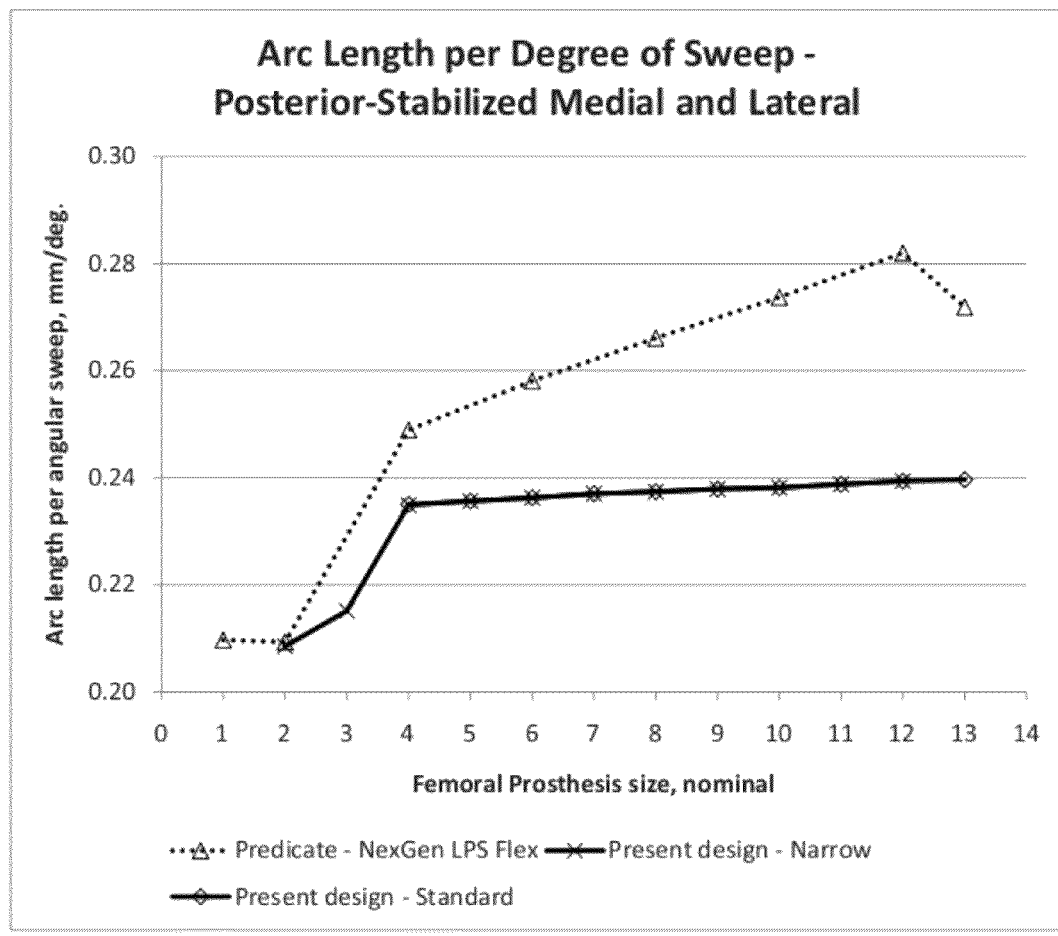
FIG. 1F is a graph plotting the arc length per degree of angular sweep for portions of femoral J-curves corresponding to greater than 90-degrees of flexion, with the illustrated data pertaining to posterior-stabilized prior art femoral components (where prior art devices are listed as "predicate") and cruciate-retaining femoral components made in accordance with the present disclosure.

Thus, FIGS. 1D and 1E quantify the bulbous geometry for profiles 42 of lateral and medial condyles 24, 26 of cruciate-retaining type femoral component 20. Similarly, FIG. 1F quantifies the corresponding bulbous J-curve geometry for lateral and medial condyles 224, 226 of posterior-stabilized type femoral component 220 (shown, for example, in FIG. 2A inclusive of the dashed lines and FIG. 5A) in a family of femoral components as compared to the femoral components of the prior art Zimmer NexGen LPS Flex prosthesis system, described above. As illustrated, a dotted-line data set illustrates that the medial and lateral condyles of the femoral components of the prior art Zimmer NexGen LPS Flex prosthesis system define a bulbousness ratio of between 0.209 mm/degree (for the smallest and second-smallest nominal sizes) and 0.282 mm/degree (for the second-largest nominal size). The family of femoral components made in accordance with the present disclosure can include at least four nominal component sizes and define a bulbousness ratio of between 0.208 mm/degree (for the smallest nominal size) and 0.240 mm/degree (for the largest nominal size), with each comparable size of the present components having a bulbousness ratio below the comparable size of the prior art devices (as shown).

Advantageously, the above-described bulbous geometry of condyles 24, 26, 224, 226 facilitates a reduced anterior/posterior condylar thickness $T_C$ in such condyles as compared to the larger anterior/posterior condylar thickness $T_A$ while also enabling high flexion (i.e., flexion of at least 130 degrees, as noted above). For such high-flexion enablement to exist, angular sweep a must be sufficiently large such that an articular portion of J-curves is available at deep-flexion orientations. Stated another way with reference to lateral condyle 24 shown in FIG. 1C, profile 42 of J-curve 27L must "make the turn" completely from 90-degrees flexion at posterior-most point 34 through a deep flexion orientation at 130 degrees or greater.

The reduction in condylar thickness $T_C$ as compared to prior art condylar thickness $T_A$ is facilitated by the bulbous geometry of the portion of J-curves 27L, 27M occupied by profile 42, which in turn flows from a reduction in average radius R as compared to prior art radius $R_A$ as discussed above. More particularly, these geometrical features of the portions of J-curves 27L, 27M occupied by profile 42 allow J-curves 27L, 27M to "make the turn" required in a smaller allotted anterior/posterior space. In an exemplary embodiment, the relatively greater arc length per degree of angular sweep and smaller radius R defined by bulbous profile 42 allows the approximately 80-degree angular sweep α from posterior-most contact point 34 to terminal profile 44 to be completed in a shorter anterior/posterior span, thereby allowing the overall thickness $T_C$ of condyle 24 to be reduced relative to thickness $T_A$ of predicate condyle 24A.

Advantageously, this reduced condylar thickness $T_C$ shifts posterior bone contacting surface 58 posteriorly with respect to the predicate posterior bone contacting surface 58A, as illustrated in FIG. 1C, while preserving high-flexion enablement. Thus, femoral component 20 satisfies an unmet need by safely allowing very deep flexion (e.g., between 130 and 170 degrees) while also allowing the posterior portions of lateral and medial condyles 24, 26 to be relatively thin, thereby reducing the amount of bone that must be resected as compared to predicate devices. For example, the family of femoral component sizes provided by the prior art Zimmer CR Flex prior art designs define thickness $T_A$ of between 8.5 mm and 8.6 for the two smallest prosthesis sizes and in excess of 11 mm for the remaining larger prosthesis sizes. An alternative prior art Zimmer CR Flex prior art design, referred to in the present application as the "CR Flex Minus" prosthesis system, defines thickness $T_A$ of between 9.1 mm and 9.6 mm across the range of prosthesis sizes.

In an exemplary cruciate-retaining embodiment (FIGS. 1D and 1E), bulbous profile 42 facilitates a condylar thickness $T_C$ of 8 mm for the smallest two prosthesis sizes and 9 mm for the remaining prosthesis sizes, as measured by the maximum material thickness between posterior-most points 34, 36 and posterior bone-contacting surface 58. This thickness $T_C$ is less than thickness $T_A$ for comparable prosthesis sizes in the above-described prior art high-flexion devices.

Thus up to 2.3 mm of bone adjacent posterior bone contacting surface 58 is preserved through the use of femoral component 20 as compared to comparably-sized prior art high-flexion femoral prostheses. In an exemplary embodiment, the overall anterior/posterior space $AP_F$ (FIG. 1B) between anterior and posterior bone-contacting surfaces 50, 58, which corresponds to the anterior/posterior extent of the distal femur after preparation to receive femoral component 20, is between 33 mm and 56 mm. The numerical value of anterior/posterior space $AP_F$ is relatively smaller or larger in direct correspondence to the size of component 20 within a family of component sizes.

In an exemplary posterior-stabilized embodiment (FIGS. 1F and 5A), bulbous profile 42 facilitates a condylar thickness $T_C$ of 9 mm for the smallest two prosthesis sizes and 10 mm for the remaining prosthesis sizes, as measured by the maximum material thickness between posterior-most points 34, 36 and posterior bone-contacting surface 258. This thickness $T_C$ is less than thickness $T_A$ for comparable prosthesis sizes in the prior art high-flexion devices. For example, a family of prior art femoral component sizes in the Zimmer NexGen LPS Flex prosthesis system, which is a posterior-stabilized design which enables high flexion, defines thickness $T_A$ of between 10.4 mm and 10.5 for the two smallest prosthesis sizes and between 12.2 mm and 12.4 for the remaining larger prosthesis sizes.

Thus between 1.4 mm and 2.4 mm of bone adjacent posterior bone contacting surface 258 is preserved through the use of femoral component 220 as compared to comparably-sized prior art high-flexion femoral prostheses. In an exemplary embodiment, the overall anterior/posterior space $AP_F$ between anterior and posterior bone-contacting surfaces 250, 258, which corresponds to the anterior/posterior extent of the distal femur after preparation to receive femoral component 220, is between 33 mm and 56 mm. The numerical value of anterior/posterior space $AP_F$ is relatively smaller or larger in direct correspondence to the size of component 220 within a family of component sizes.

2. Articular Features: "Standard" and "Narrow" Femoral Components for Each Component Size.

Figure 3A:
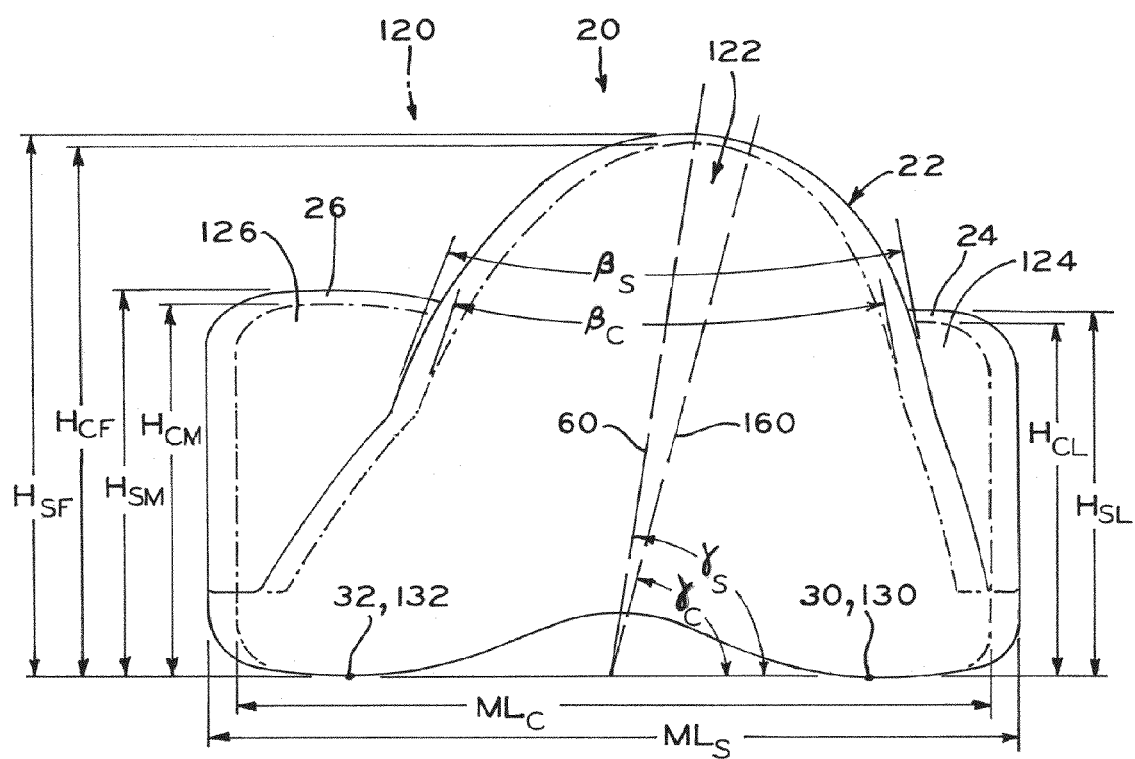
FIG. 3A is an anterior, elevation view illustrating a pair of femoral components made in accordance with the present disclosure.
Figure 3B:
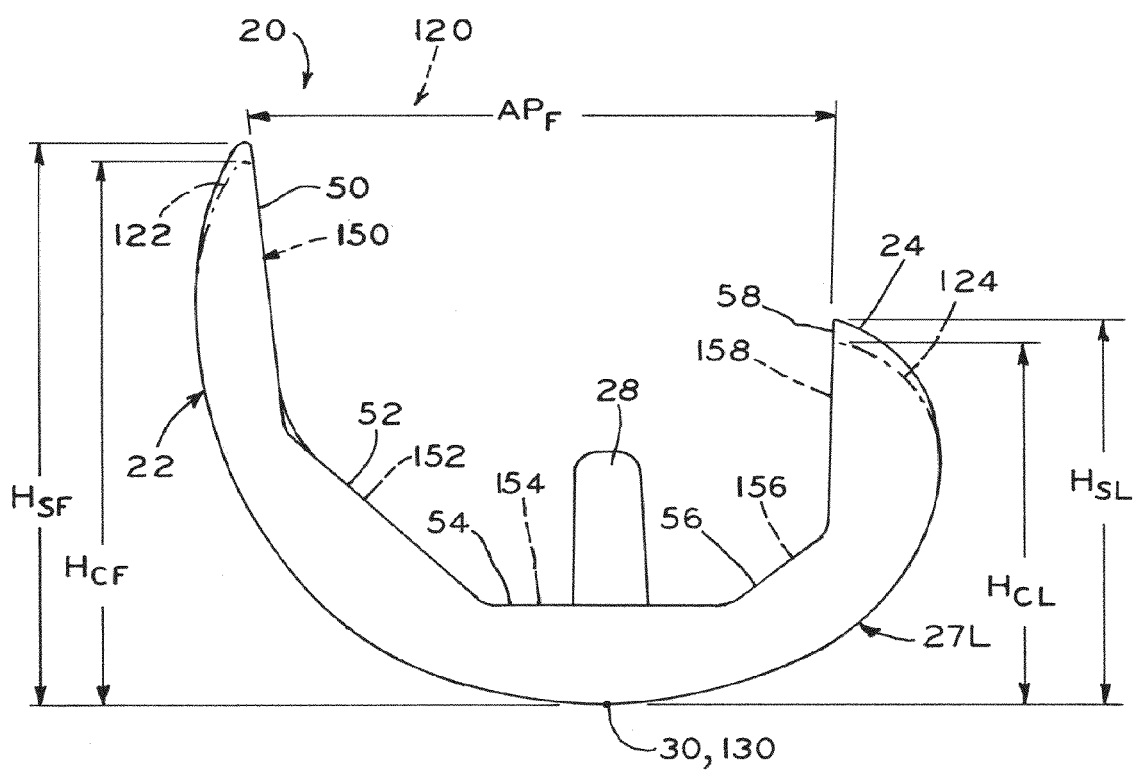
FIG. 3B is a sagittal, elevation view illustrating the pair of femoral components of FIG. 3A.

Turning to FIG. 3A, an anterior elevation view of regular femoral component 20 is shown juxtaposed against a corresponding narrow component 120. Regular component 20 includes articular geometry in accordance with the present disclosure and adapted for a particular subset of potential knee replacement patients, while narrow component 120 has articular geometry different from component 20 and adapted for a different subset of patients. As best seen in FIG. 3B, femoral components 20, 120 share a common sagittal geometry such that component 120 is adapted to selectively mount to a femur which has been prepared to accept femoral component 20. Advantageously, this common sagittal geometry allows a surgeon to choose intraoperatively between components 20, 120.

As shown in FIG. 3B, regular femoral component 20 has five bone contacting surfaces disposed opposite the articular surfaces of anterior flange 22 and lateral and medial condyles 24, 26. These five bone contacting surfaces include anterior bone contacting surface 50, anterior chamfer surface 52, distal bone contacting surface 54, posterior chamfer surface 56, and posterior bone contacting surface 58. Anterior, distal and posterior bone-contacting surfaces 50, 54, 58 are adapted to abut a resected surface of a femur upon implantation of femoral component 20. In an exemplary embodiment, anterior chamfer and posterior chamfer surfaces 52, 56 are sized and positioned to leave a slight gap between surfaces 52, 56 and the respective adjacent chamfer facet of the resected femur upon implantation, such as about 0.38 mm. However, because this gap is small and may be filled in with fixation material adhering the resected chamfer facets to chamfer surfaces 52, 56, anterior chamfer and posterior chamfer surfaces 52, 56 are also referred to as "bone-contacting" surfaces herein.

As detailed in the Zimmer Surgical Techniques, a surgical procedure to implant a femoral component such as component 20 includes resecting the distal end of a femur to create five facets corresponding with bone contacting surfaces 50, 54, 58 and chamfers 52, 56. Relatively tight tolerances between the distal end of the femur and the five bone-contacting surfaces of femoral component 20 ensure a snug fit.

Femoral component 20 is provided in a family or kit of differing component sizes, as graphically portrayed in FIGS. 3C-3F and described in detail below. Consideration in choosing an appropriately sized femoral component 20 from among the set of components include the amount of bone resection necessary to accommodate the component 20, and the ability for resected surfaces to make full-area, flush contact with the adjacent bone-contacting surfaces 50, 52, 54, 56, 58 of femoral component 20 (see, e.g., FIG. 11B showing femoral component 220 implanted upon femur F). To implant femoral component 20, the anterior/posterior distance defined by the anterior and posterior facets of the resected femur must match the corresponding anterior/posterior distance $AP_F$ (FIG. 1B) between anterior bone contacting surface 50 and posterior bone contacting surface 58. An appropriately sized femoral component 20 provides snug abutting contact between all five of the bone-contacting surfaces of femoral component 20 and the distal resected facets, while also resulting in a desired articular profile in the knee prosthesis.

In the interest of preserving as much natural bone stock as practical, it is desirable to maximize the anterior/posterior distance $AP_F$ of femoral component 20 provided the articular profile is acceptable to the surgeon. However, no two patients are exactly alike. In some cases, for example, the overall sagittal geometry of bone contacting surfaces 50, 54, 58 and chamfers 52, 56 may represent an ideal match for the femur of a particular patient, but the peripheral characteristics of femoral component 20 (described in detail below) may not present an adequate match to the other anatomical features of the femur. The present disclosure addresses this eventuality by providing alternative femoral component designs sharing a common sagittal geometry, as illustrated in FIG. 3B.

For example, the height $H_{SF}$ and geometry of anterior flange 22 of regular femoral component 20 (FIGS. 3A, 3B and 3D) may result in "overhang" thereof past the associated anterior facet of the resected femur. Similarly, the overall medial/lateral width $ML_S$ of regular femoral component 20 (FIGS. 3A and 3C) may be too large, as indicated by overhang of one or more bone-contacting surfaces 50, 52, 54, 56, 58 past the medial and/or lateral edge of the patient's femur. Yet another possibility is that the overall proximal/distal heights $H_{SM}$, $H_{SL}$ of medial and lateral condyles 26, 24, respectively (FIGS. 3A, 3B, 3E, and 3F) may be too large, also potentially resulting in overhang of the component beyond the resected posterior facets of the femur. In each of these cases, femoral component 20 would normally be considered too large, possibly resulting in the use of a smaller component size with its associate reduction in anterior/posterior distance $AP_F$ (FIGS. 1B and 3B).

Moreover, Applicants have found that for a substantial subset of knee replacement candidates, "regular" or standard femoral component sizes may have an appropriate anterior/posterior distance $AP_F$ and spatial arrangement of bone contacting surfaces 50, 54, 58 and chamfers 52, 56, but are too large with respect to one or more of the aforementioned characteristics of the component periphery, and usually all three (i.e., height $H_{SF}$ and geometry of anterior flange 22, overall width $ML_S$, and condyle heights $H_{SM}$, $H_{SL}$).

To accommodate a wider variety of femoral geometries while facilitating maximum preservation of healthy bone stock during the surgical procedure, a prosthesis system in accordance with the present disclosure provides a set of "narrow" femoral components 120 which share a common spatial arrangement of bone contacting surface geometry with a corresponding set of femoral components 20 (i.e., a common anterior/posterior distance $AP_F$ and associated sagittal profile of resected facets), but includes anterior flange 122, lateral condyle 124 and medial condyle 126 which are strategically downsized.

Figure 6:
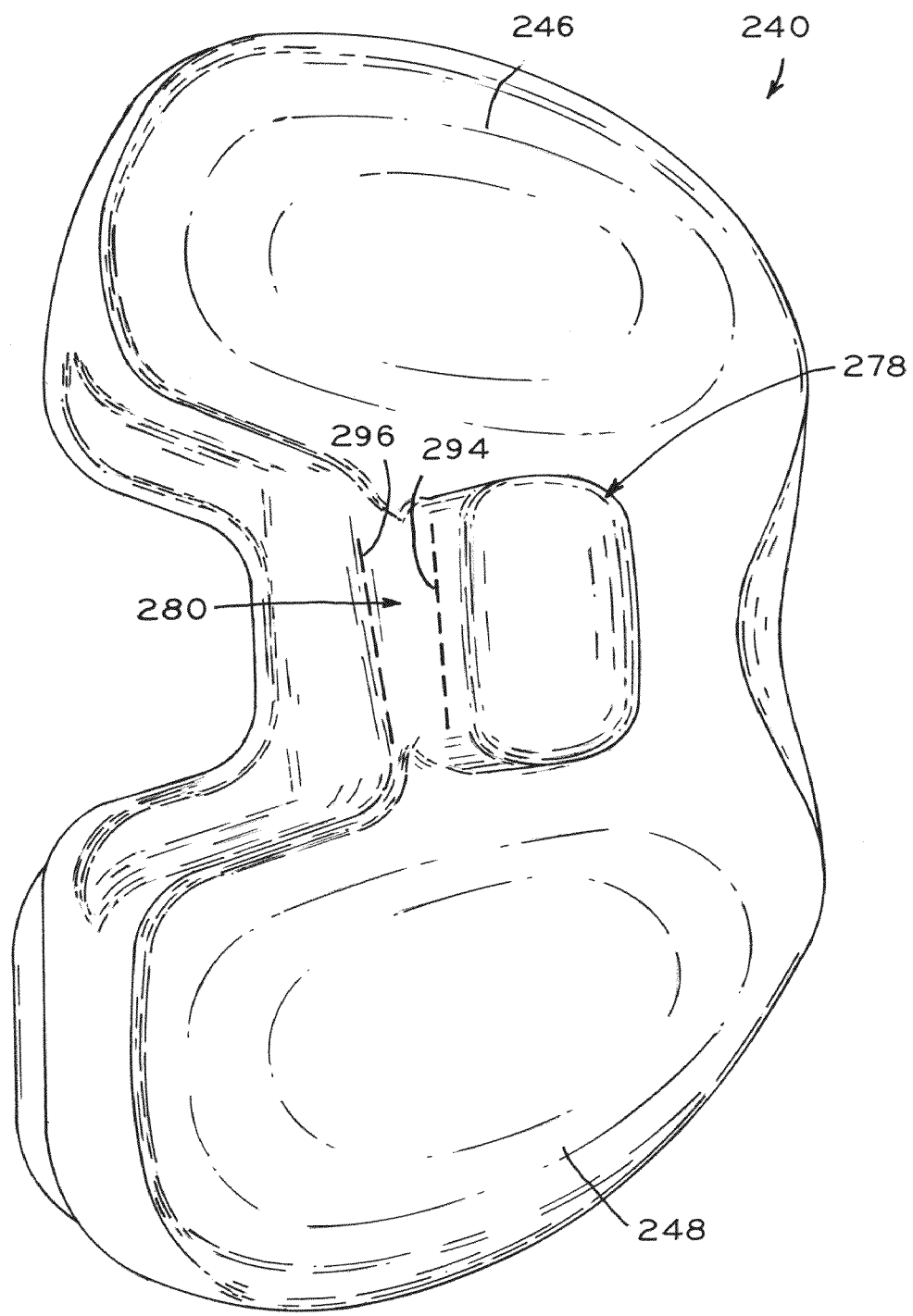
FIG. 6 is a proximal, perspective view of a tibial bearing component made in accordance with the present disclosure.

In the anterior elevation view of FIG. 3A, the periphery of narrow femoral component 120 is aligned with the periphery of regular femoral component 20 such that lateral distal-most contact points 30, 130 and medial distal-most contact points 32, 132 are superimposed over one another. Moreover, the articular profile and geometry of condyles 24, 26 of femoral component 20, including medial and lateral J-curves 27M, 27L described above (FIG. 3B), are substantially identical to the corresponding profile of condyles 124, 126 of narrow femoral component 120, with the exception of the reduction in various peripheral aspects of femoral component 120 as compared to component 20 as described below. Taking account of such reductions, the articular surfaces of femoral component 120 are subsumed by the articular surfaces of femoral component 20 when the articular surfaces of components 20, 120 are superimposed, as illustrated in FIGS. 3A and 3B. Thus, both of femoral components 20 and 120 may be used interchangeably with a selected abutting tibial component, such as tibial bearing component 240 (FIG. 6).

Figure 3C:
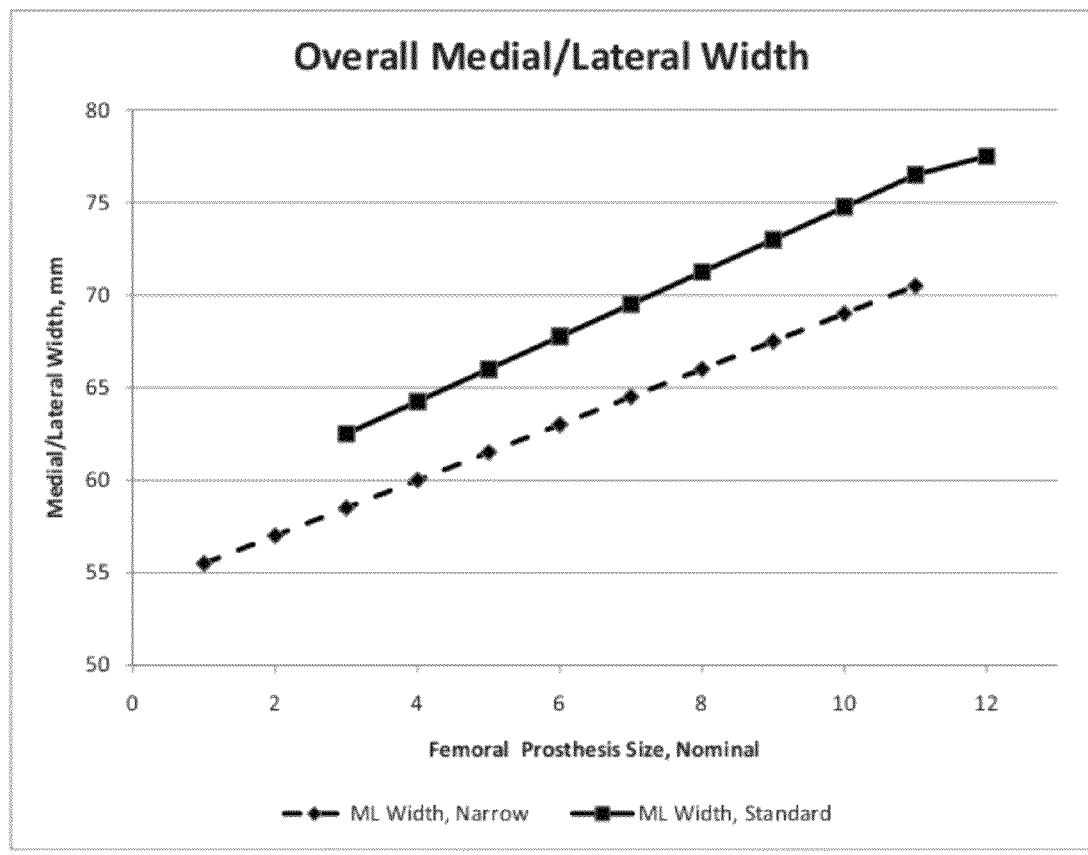
FIG. 3C is a graph plotting the overall medial/lateral width of families of regular and narrow femoral components made in accordance with the present disclosure.
Figure 3D:
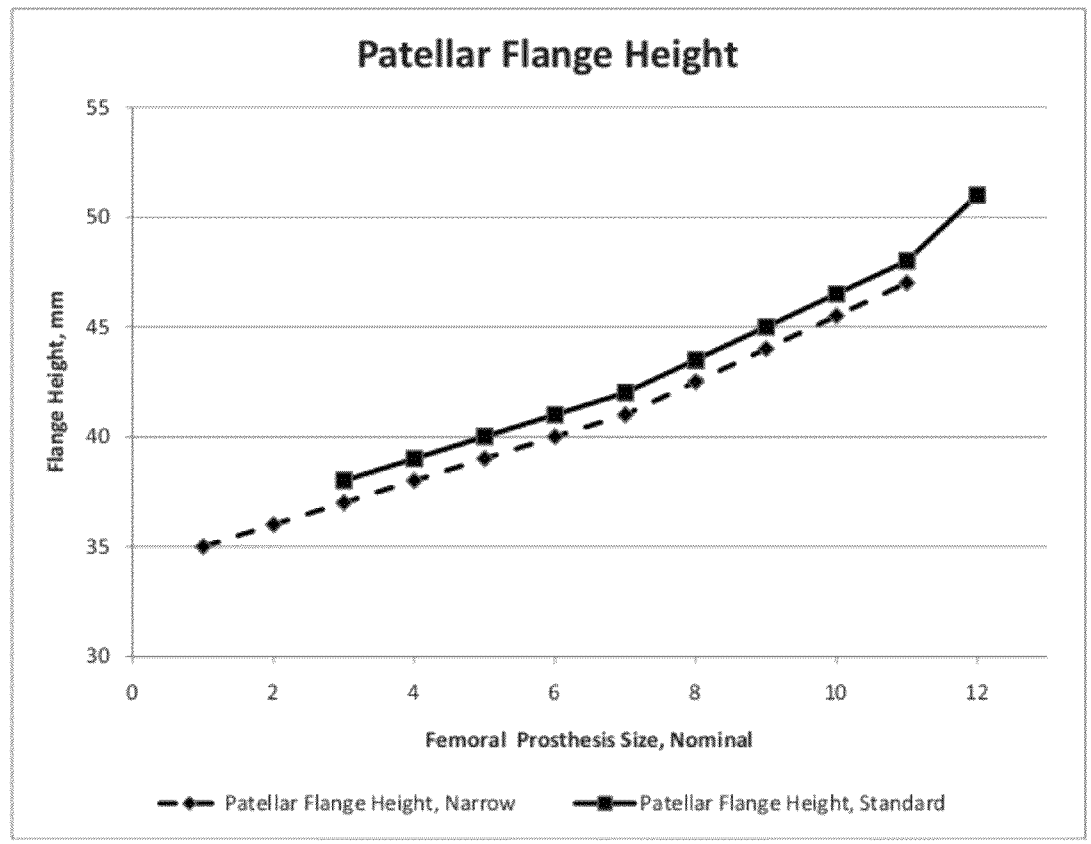
FIG. 3D is a graph plotting the proximal/distal height of the anterior flanges of the families of femoral components shown in FIG. 3C.

However, anterior flange 122 of narrow femoral component 120 defines a shorter overall flange height $H_{CF}$, as illustrated in FIGS. 3A, 3B and 3D. In an exemplary embodiment, height $H_{CF}$ may be reduced by 1 mm from the corresponding height $H_{SF}$ of anterior flange 22 of regular femoral component 20 for any given prosthesis size. As shown in FIG. 3D, height $H_{SF}$ of femoral component 20 ranges from 38 mm to 51 mm, and grows progressively larger across a range of prosthesis sizes (starting from a nominal size 3 and ending at a nominal size 12). By contrast, height $H_{CF}$ of femoral component 120 ranges from 35 mm to 47 across an overlapping range of prosthesis sizes (starting from a nominal size 1 and ending at a nominal size 11). As illustrated in the lines connecting the data points of FIG. 3D, anterior flange heights $H_{CF}$ of each size of femoral component 120 are consistently less than the corresponding flange heights $H_{SF}$ for corresponding sizes of femoral component 20. A common nominal size for femoral components 20, 120 denotes a substantially identical spatial arrangement of bone contacting surface geometry, including a common anterior/posterior distance $AP_F$, such that either of a particular size of component 20, 120 can be implanted onto the same resected femur.

Figure 3E:
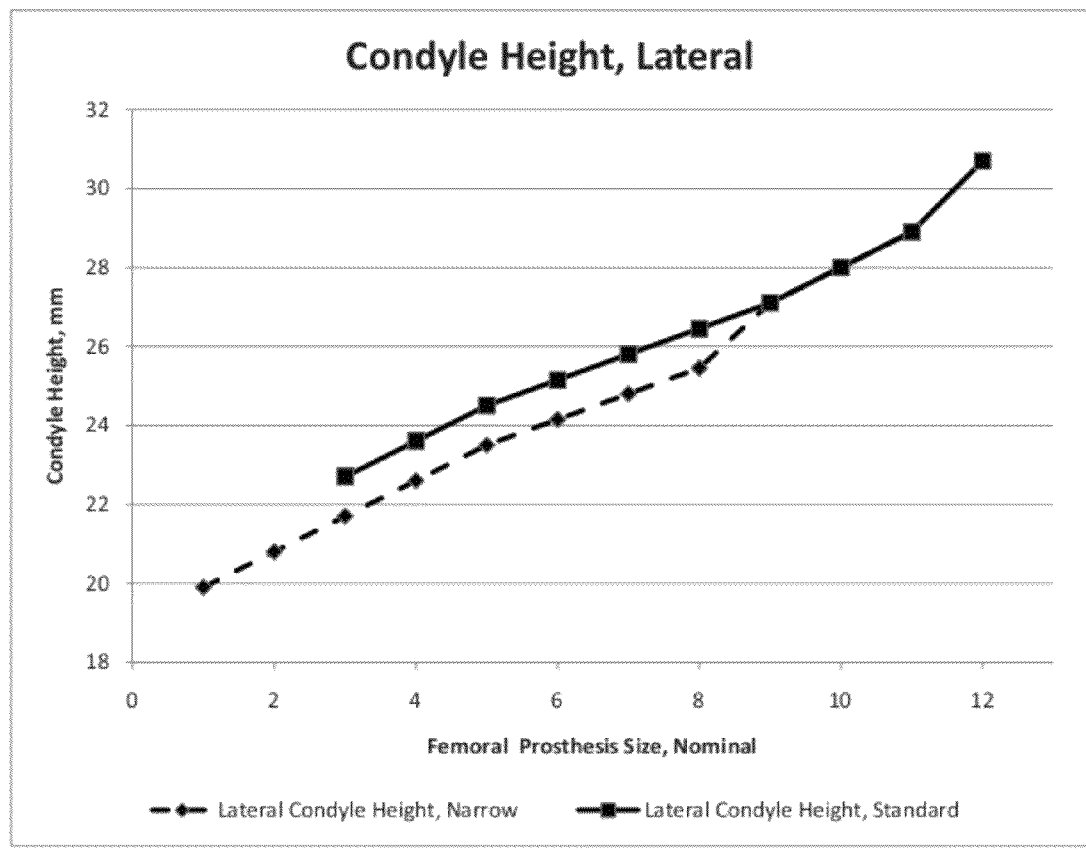
FIG. 3E is a graph plotting the proximal/distal height of the lateral condyles of the families of femoral components shown in FIG. 3C.
Figure 3F:
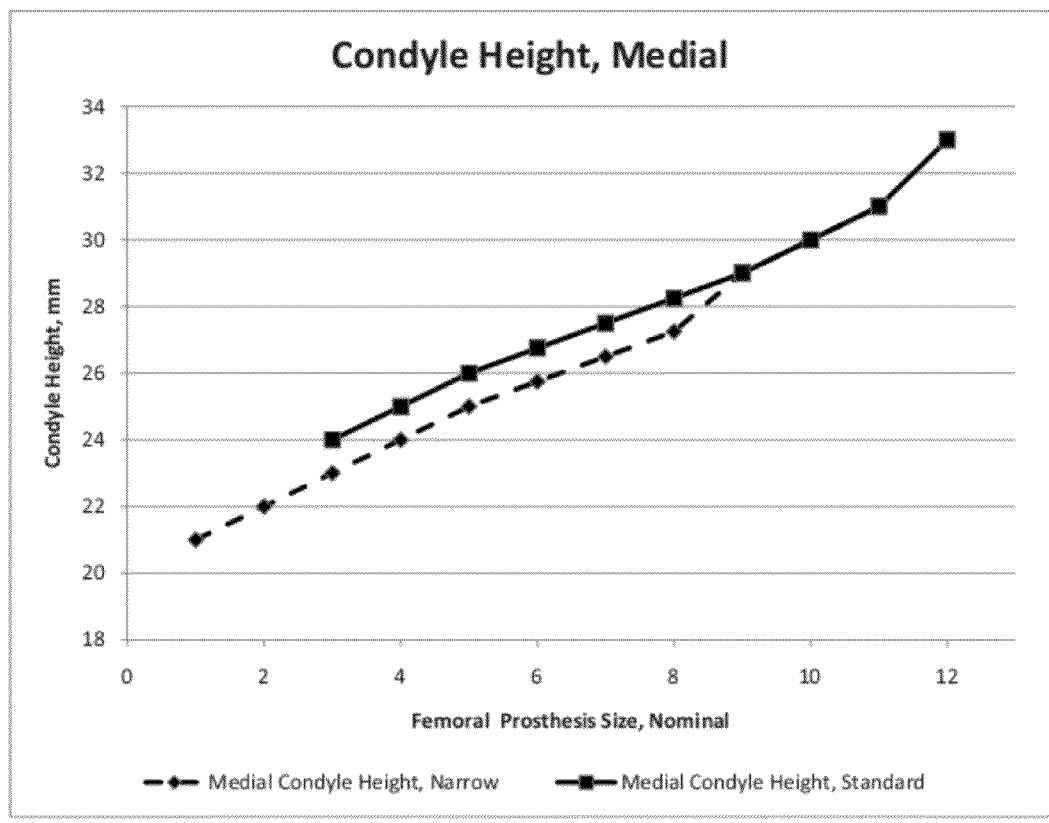
FIG. 3F is a graph plotting the proximal/distal height of the medial condyles of the families of femoral components shown in FIG. 3C.

Medial condyle height $H_{CM}$ of medial condyle 126 is also shorter than the corresponding medial condyle height $H_{SM}$ of standard medial condyle 26. In an exemplary embodiment, height $H_{CM}$ may be reduced by 1 mm from the corresponding height $H_{SM}$ of medial condyle 26 of regular femoral component 20 for any given prosthesis size. As shown in FIG. 3F, height $H_{SM}$ of medial condyle 26 of regular femoral component 20 ranges from 24 mm to 33 mm, and grows progressively larger across a range of prosthesis sizes (starting from a nominal size 3 and ending at a nominal size 12). By contrast, height $H_{CM}$ of femoral component 120 ranges from 21 mm to 31 mm across an overlapping range of prosthesis sizes (starting from a nominal size 1 and ending at a nominal size 11). As illustrated in the lines connecting the data points of FIG. 3F, medial condyle heights $H_{CM}$ of femoral component 120 are consistently less than the corresponding medial condyle heights $H_{SM}$ of femoral component 20 across a range of corresponding sizes.

Similarly, lateral condyle height $H_{IL}$ of lateral condyle 124 is less than lateral condyle height $H_{SL}$ of lateral condyle 24. In an exemplary embodiment, height $H_{CL}$ may be reduced by 1 mm from the corresponding height $H_{SL}$ of lateral condyle 24 of regular femoral component 20 for any given prosthesis size. As shown in FIG. 3E, height $H_{SL}$ of lateral condyle 24 of regular femoral component 20 ranges from 22 mm to 31 mm, and grows progressively larger across a range of prosthesis sizes (starting from a nominal size 3 and ending at a nominal size 12). By contrast, height $H_{CL}$ of lateral condyle 124 of femoral component 120 ranges from 19 mm to 29 mm across an overlapping range of prosthesis sizes (starting from a nominal size 1 and ending at a nominal size 11). As illustrated in the lines connecting the data points of FIG. 3E, lateral condyle heights $H_{CL}$ of femoral component 120 are consistently less than the corresponding lateral condyle heights $H_{SL}$ of femoral component 20 across a range of corresponding sizes.

Referring now to FIG. 3A, the overall width $ML_C$ of narrow femoral component 120 is also consistently less than the overall width $ML_S$ of femoral component 20 across a range of prosthesis sizes. In an exemplary embodiment, width $ML_C$ may be reduced by between 1 mm from the corresponding width $ML_S$ of regular femoral component 20 for any given prosthesis size. As shown in FIG. 3C, width $ML_S$ of regular femoral component 20 ranges from 62 mm to 78 mm, and grows progressively larger across a range of prosthesis sizes (starting from a nominal size 3 and ending at a nominal size 12). By contrast, width $ML_C$ of femoral component 120 ranges from 55 mm to 70 mm across an overlapping range of prosthesis sizes (starting from a nominal size 1 and ending at a nominal size 11). As illustrated in the lines connecting the data points of FIG. 3C, width $ML_C$ of femoral component 120 is consistently less than the corresponding width $ML_S$ of femoral component 20 across each size in a range of corresponding sizes.

The above-described changes in peripheral characteristics to femoral component 120, as compared to femoral component 20, advantageously leave the overall sagittal profile of components 20, 120 similar, and with substantially identical anterior/posterior spaces between anterior bone-contacting surfaces 50, 150 and posterior bone-contacting surfaces 58, 158 (including distance $AP_F$). However, it is appreciated that the shortening of anterior flange 122 and posterior condyles 124, 126 do alter the sagittal profile of component 120 in that such profile is "shortened" overall. However, the sagittal profile of component 120 is subsumed by the corresponding profile of regular component 20 (as illustrated in FIG. 3B), such that narrow component 120 will fit the same resected femur as component 20. Advantageously, this shortening prevents potential overhang of component 120 past the resected portions of some femurs, as discussed above.

In addition to the differences in the peripheral characteristics described above, articular features of anterior flange 122 also vary as compared to anterior flange 22 of regular femoral component 20. Referring to FIG. 3A, standard anterior flange 22 defines flange taper angle $\beta_S$, which is the taper angle defined by the medial and lateral walls adjoining anterior bone-contacting surface 50 to the opposed articular surface of flange 22. In the illustrative embodiment of FIG. 3A, taper angle $\beta_S$ angle is measured between lines tangent to points along the rounded frontal profile defined by the medial and lateral walls of anterior flange 22 at the base of anterior bone-contacting surface 50 (i.e., where anterior bone-contacting surface 50 meets anterior chamfer surface 52). However, it is appreciated that taper angle $\beta_S$ may be defined at any point along such rounded edges, provided the medial and lateral tangent lines are drawn at common proximal/distal heights for purposes of comparison between femoral components 20, 120.

In contrast to standard anterior flange 22, narrow anterior flange 122 defines taper angle $\beta_C$ which is different from taper angle $\beta_S$ for any given nominal prosthesis size. This disparity of taper angles facilitates a relatively smaller disparity in overall heights $H_{SF}$, $H_{CF}$ of anterior flanges 22, 122 as compared to the relatively larger disparity in overall widths $ML_C$, $ML_S$ thereof (as shown by comparison of FIGS. 3C and 3D, and detailed above). Advantageously, this differing taper defined by taper angles $\beta_S$, $\beta_C$ in anterior flanges 22, 122 accommodates a wide range of natural patient anatomies for larger- and smaller-stature patients.

Figure 8:
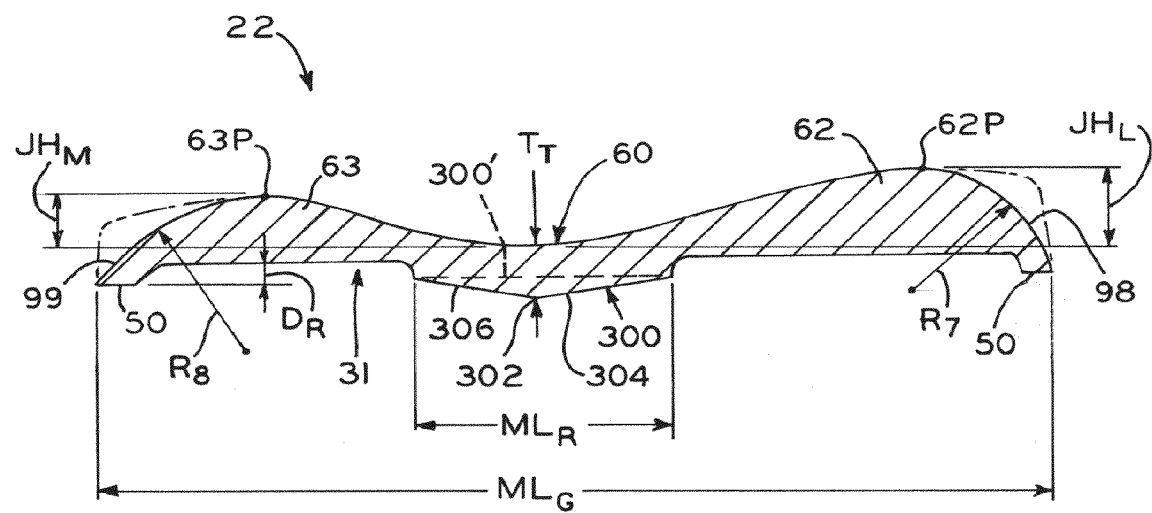
FIG. 8 is a proximal plan, cross-sectional view of the anterior flange of the femoral component shown in FIG. 1B, taken along line 8-8 shown in FIG. 1B.

Yet another difference between regular femoral component 20 and narrow femoral component 120 is the angle defined by patellar grooves 60, 160 (also referred to a patellar sulcus) formed in anterior flanges 22, 122 respectively. As best illustrated in FIG. 8, anterior flange 22 defines patellar groove 60, which is a longitudinal concavity or trough extending along the proximal/distal extent of anterior flange 22, as shown in FIG. 3A. A natural or prosthetic patella articulates with groove 60 during normal flexion and extension of the knee. Turning back to FIG. 3A, the path of the deepest portion of the patellar trough defined by patellar groove 60 is represented by the illustrated sulcus axis, which is extrapolated proximally and distally for clarity. The sulcus axis of patellar groove 60 defines angle $\gamma_S$ with a transverse plane tangent to distal most points 30, 32 of lateral and medial condyles 24, 26. In the illustrated embodiment of FIG. 3A, this transverse plane appears as an imaginary line connecting distal-most points 30, 32 (and also, therefore, connecting distal-most points 130, 132 of the superimposed narrow femoral component 120).

As illustrated, standard patellar groove angle $\gamma_S$ is greater than the corresponding groove angle $\gamma_C$ defined by patellar groove 160 of anterior flange 122. In an exemplary embodiment, standard patellar groove angle $\gamma_S$ is 83 degrees, while the narrow-component patellar groove angle $\gamma_C$ is 80 degrees.

It is contemplated that for each regular femoral component size within the range of available sizes (i.e., for a range of unique, differing anterior distances $AP_F$), one narrow femoral component including the features described above may be provided. In an exemplary embodiment, up to twelve or more unique femoral component sizes may be provided, with each of the 12 sizes including both regular and narrow femoral components 20, 120. Thus, a surgeon may intraoperatively elect to implant narrow femoral component 120 if it becomes apparent that regular femoral component 20 is too large in certain respects (as described above).

An exemplary surgical technique and apparatus for intraoperatively choosing between regular femoral component 20 and narrow femoral component 120 is described in U.S. patent application Ser. No. 13/161,624, filed Jun. 16, 2011 and entitled FEMORAL PROSTHESIS SYSTEM, the entire disclosure of which is hereby expressly incorporated herein by reference.

However, it is also contemplated that multiple narrow components may be provided corresponding to each standard component size. Each of the plurality of narrow components may feature different widths, heights and/or anterior flange arrangements in accordance with the principles described above.

3. Articular Features: Differential Condyle Height.

Referring again to FIG. 1C, medial condyle 26 is taller (i.e., defines a greater proximal/distal extent) as compared to lateral condyle 24 to define height differential $\Delta H$. In an exemplary embodiment, height differential $\Delta H$ may be between 1.1 and 2.3 mm depending on prosthesis size. As described in detail below, an exemplary family or set of femoral components 20 may include twelve prosthesis sizes, with the smallest size defining height differential $\Delta H$ at 1.1 mm and the largest size defining height differential $\Delta H$ at 2.3 mm. Intermediate sizes define intermediate height differentials $\Delta H$ within the aforementioned range.

In an exemplary embodiment, each adjacent pair of prosthesis sizes have respective height differentials $\Delta H$ that vary by 0.1 mm, with larger sizes having proportionally larger variance in height differentials $\Delta H$. Thus, for example, a prosthesis having a nominal size of 1 may have a height differential $\Delta H$ of 1.1 mm, while a prosthesis having nominal size 2 has a height differential $\Delta H$ of 1.2 mm.

By contrast, the femoral components of the prior art Zimmer NexGen CR Flex prosthesis system have medial condyles which are taller than the lateral condyles by between 1.3 mm and 2.1 mm. Further, families of femoral components of the prior art Zimmer NexGen CR Flex prosthesis system have variability in the condyle height differential which do not grow proportionally larger as nominal sizes increase, instead having differentials which grow at varying rates across the range of sizes.

Advantageously, providing a relatively shorter lateral condyle 24 allows such lateral condyle 24 to roll back and externally rotate when the knee prosthesis is in deep flexion (FIG. 2A). This deep-flexion rollback and rotation is permitted by shortened lateral condyle 24, while any potential impingement between condyle 24 and adjacent structures and/or soft tissues is avoided. This facilitation of femoral roll back is particularly effective in combination with the other features of a cruciate-retaining femoral component, such as component 20, which lacks a femoral cam as described herein.

4. Soft Tissue Accommodation: Femoral Cam Geometry.

Figure 5A:
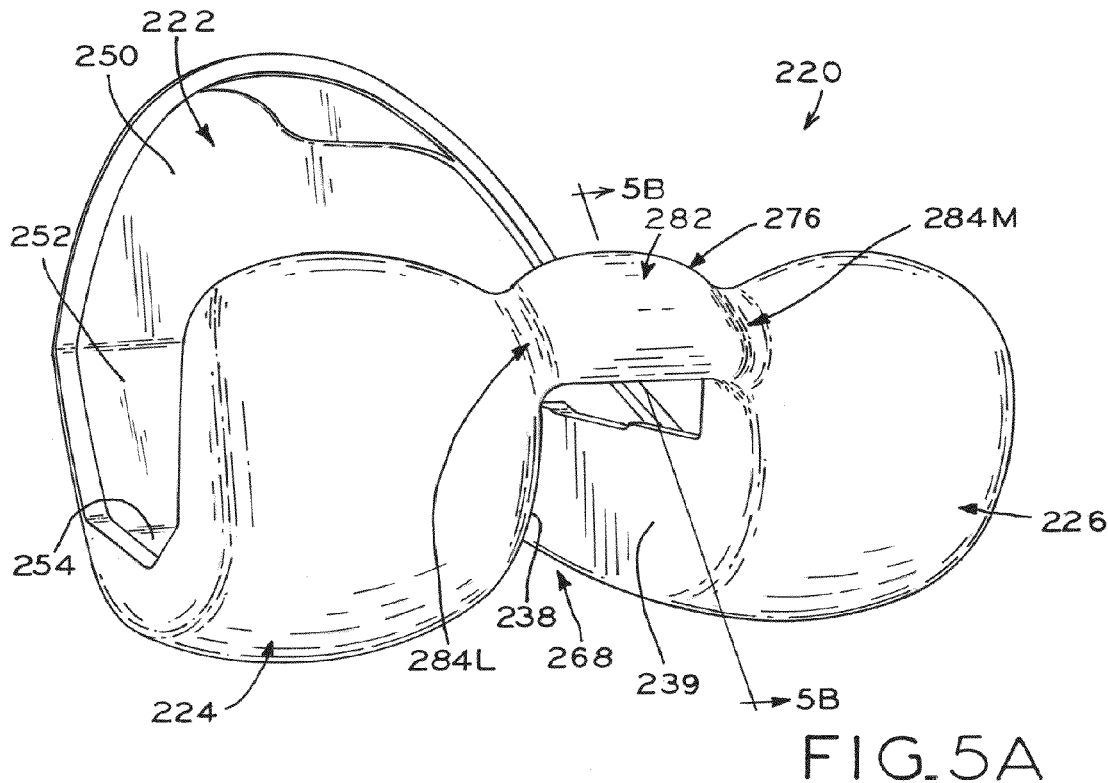
FIG. 5A is a posterior, perspective view of a femoral component made in accordance with the present disclosure.

Turning now to FIG. 5A, posterior stabilized (PS) femoral component 220 having femoral cam 276 is illustrated. Femoral component 220 is substantially similar to femoral component 20 described above, with reference numerals of component 220 corresponding to the reference numerals used in component 20, except with 200 added thereto. Structures of femoral component 220 correspond to similar structures denoted by corresponding reference numerals of femoral component 20, except as otherwise noted.

However, femoral component 220 is specifically adapted for use in a surgical procedure wherein the posterior cruciate ligament (PCL) is resected. More particularly, femoral component 220 includes femoral cam 276 spanning intercondylar notch 268 formed between lateral and medial condyles 224, 226. Intercondylar notch 268 is bounded at its lateral and medial sides by lateral and medial condylar walls 238, 239 (FIG. 5C), which face inwardly toward one another and each extend proximally from distal bone-contacting surface 254. Condylar walls 238, 239 are engageable with spine 278 of tibial bearing component 240 (FIG. 6) to provide medial/lateral stability to femoral component 220 from full extension to at least mid-flexion; therefore, in an exemplary embodiment condylar walls 238, 239 are substantially parallel to one another to define a total medial/lateral width $ML_T$ which remains constant across the anterior/posterior extent of intercondylar notch 268.

Femoral cam 276 is sized, shaped and positioned to articulate with spine 278 of tibial bearing component 240 (FIG. 6) along posterior articular surface 280 thereof (as described in detail below). Spine 278 extends proximally from the articular surface of tibial bearing component 240, and is disposed between lateral and medial articular compartments 246, 248 thereof. Additional details of spine 278 and its interaction with femoral cam 276 are described in: U.S. Provisional Patent Application Ser. No. 61/561,657, filed Nov. 18, 2011 and entitled "TIBIAL BEARING COMPONENT FOR A KNEE PROSTHESIS WITH IMPROVED ARTICULAR CHARACTERISTICS"; U.S. Provisional Patent Application Ser. No. 61/577,293, filed Dec. 19, 2011 and entitled "TIBIAL BEARING COMPONENT FOR A KNEE PROSTHESIS WITH IMPROVED ARTICULAR CHARACTERISTICS"; U.S. Provisional Patent Application Ser. No. 61/592,576, filed Jan. 30, 2012 and entitled "TIBIAL BEARING COMPONENT FOR A KNEE PROSTHESIS WITH IMPROVED ARTICULAR CHARACTERISTICS"; U.S. Provisional Patent Application Ser. No. 61/621,361, filed on Apr. 6, 2012 and entitled "TIBIAL BEARING COMPONENT FOR A KNEE PROSTHESIS WITH IMPROVED ARTICULAR CHARACTERISTICS"; U.S. Provisional Patent Application Ser. No. 61,621,363, filed on Apr. 6, 2012 and entitled "TIBIAL BEARING COMPONENT FOR A KNEE PROSTHESIS WITH IMPROVED ARTICULAR CHARACTERISTICS"; U.S. Provisional patent application Ser. No. 61/621,364, filed on Apr. 6, 2012 and entitled "TIBIAL BEARING COMPONENT FOR A KNEE PROSTHESIS WITH IMPROVED ARTICULAR CHARACTERISTICS"; U.S. Provisional Patent Application Ser. No. 61/621,366, filed on Apr. 6, 2012 and entitled "TIBIAL BEARING COMPONENT FOR A KNEE PROSTHESIS WITH IMPROVED ARTICULAR CHARACTERISTICS"; U.S. patent application Ser. No. 13/459,037, filed on Apr. 27, 2012, now issued as U.S. Pat. No. 8,858,643, and entitled "TIBIAL BEARING COMPONENT FOR A KNEE PROSTHESIS WITH IMPROVED ARTICULAR CHARACTERISTICS" U.S. patent application Ser. No. 13/459,041 filed on Apr. 27, 2012, now issued as U.S. Pat. No. 9,072,607, and entitled "TIBIAL BEARING COMPONENT FOR A KNEE PROSTHESIS WITH IMPROVED ARTICULAR CHARACTERISTICS" U.S. patent application Ser. No. 13/459, 048, filed on Apr. 27, 2012, now issued as U.S. Pat. No. 8,690,954, and entitled "TIBIAL BEARING COMPONENT FOR A KNEE PROSTHESIS WITH IMPROVED ARTICULAR CHARACTERISTICS"; and U.S. patent application Ser. No. 13/459,056, filed on Apr. 27, 2012, now issued as U.S. Pat. No. 8,764,838, and entitled "TIBIAL BEARING COMPONENT FOR A KNEE PROSTHESIS WITH IMPROVED ARTICULAR CHARACTERISTICS". The entire disclosures of each of the above-identified patent applications are hereby expressly incorporated herein by reference.

Femoral cam 276 includes central articular area 282 defined by a plurality of cylindrical surfaces tangent to one another, with the longitudinal axes defined by such cylindrical surfaces all substantially parallel to one another and extending in a medial/lateral direction. Central articular area 282 is flanked by medial and lateral transition areas 284M, 284L which provide a rounded transition from the cylindrical central articular area to lateral and medial condyles 224, 226, as shown in FIG. 5A and described in detail below.

Figure 5B:
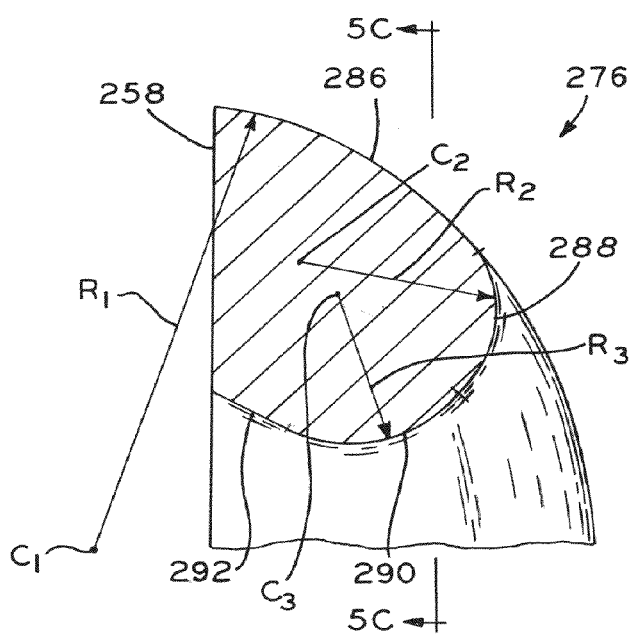
FIG. 5B is a side elevation, cross-sectional view of a portion of the femoral component shown in FIG. 5A.
Figure 5C:
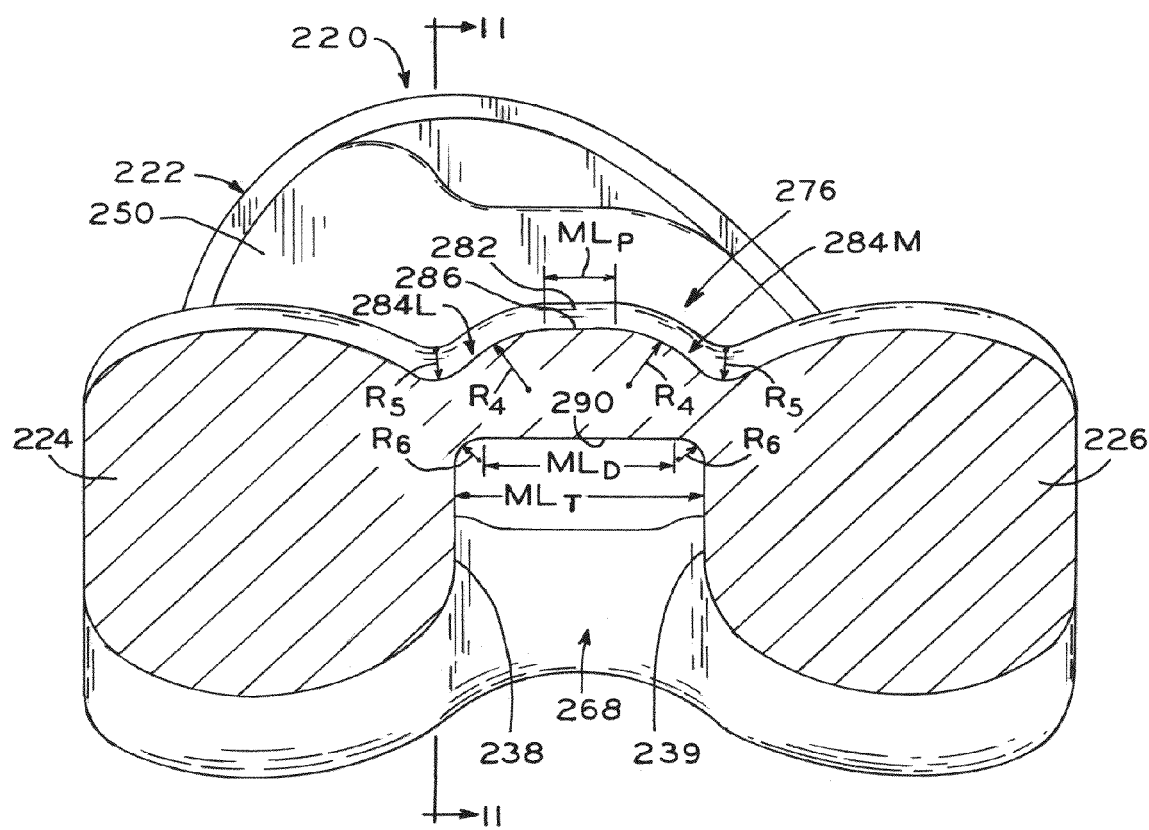
FIG. 5C is a posterior elevation, cross-sectional view of the femoral component shown in FIG. 5A.

More particularly, FIG. 5B illustrates four cylindrical surface curves 286, 288, 290, 292 as viewed in a sagittal cross-section bisecting femoral cam 276. As described in detail below, curves 286, 288, 290, 292 are indicative of surfaces when viewed from a perspective other than the sagittal perspective of FIG. 5B. Proximal curve 286 extends posteriorly from posterior bone contacting surface 258, and defines a relatively large curvature radius $R_1$. In an exemplary embodiment, radius $R_1$ may be as little as 10 mm or as large as 11.5 mm, with larger values for radius $R_1$ corresponding to larger prosthesis sizes within a family of different prosthesis sizes.

Posterior curve 288 tangentially adjoins proximal curve 286, thereby creating a smooth transition between curves 286, 288. As viewed from the sagittal perspective of FIG. 5B, posterior curve 288 extends posteriorly and distally from its junction with proximal curve 286. Posterior curve 288 defines radius $R_2$ which is smaller than radius $R_1$. In an exemplary embodiment, radius $R_2$ may be as little as 2.5 mm, 6.5 mm or 7 mm and large as 8 mm or 12 mm, or may be any size within any range defined by the foregoing values. Similar to radius $R_1$ discussed above, larger values of radius $R_1$ may correspond to larger prosthesis sizes within a family of prostheses.

Distal curve 290 tangentially adjoins posterior curve 288 to create another smooth transition between curves 288, 290. As viewed from the sagittal perspective of FIG. 5B, distal curve 290 extends distally and anteriorly from its junction with posterior curve 288. Distal curve 290 defines radius $R_3$ which is smaller than radius $R_2$ of posterior curve 288. In an exemplary embodiment, radius $R_3$ may be between 2 mm and 3 mm across all sizes in the aforementioned family of prostheses.

Anterior curve 292 tangentially adjoins distal curve 290, and extends anteriorly and proximally therefrom, to rejoin posterior bone contacting surface 258. Anterior curve 292 defines a very large radius, or is substantially flat. As noted above, curves 286, 288, 290 each define a medially/laterally extending cylindrical face, such that centers $C_1$, $C_2$, $C_3$ of radii $R_1$, $R_2$, $R_3$, respectively, lie on respective medially/laterally extending longitudinal cylinder axes. Stated another way, the cylindrical faces and longitudinal axes of curves 286, 288, 290 extend into and out of the page of FIG. 5B.

Although the sagittal curve arrangement described above utilizes three articular curves to define central articular area 282, it is contemplated that any number of mutually tangent curves may be used. For example, in certain exemplary embodiments posterior curve 288 may be broken up into two sections, in which a transitional curve portion between radii $R_1$, $R_2$ has a relatively smaller radius than either of radii $R_1$, $R_2$, thereby providing a decisive transition from the mid-flexion articular characteristics provided by posterior curve 288 (as described below) and the deep-flexion articular characteristics of proximal curve 286 (also described below).

As described above with regard to the exemplary embodiment of femoral component 220, the articular surfaces defined by curves 286, 288, 290 are shown and described as cylindrical and therefore are depicted as straight lines in the coronal cross-section of FIG. 5C. However, it is contemplated that central articular area 282 may have a slight medial/lateral curvature, such as a slight convex curvature resulting in a slightly curved coronal profile. Moreover, for purposes of the present disclosure, a geometric shape defined by a component of a knee prosthesis (such as a cylindrical surface) refers to a shape having the nominal characteristics of that geometric shape, it being appreciated that manufacturing tolerances and circumstances of in vivo use may cause such nominal characteristics to deviate slightly.

Turning now to FIG. 5C, the cylindrical surfaces including curves 286, 288, 290 define varying medial/lateral extents along the respective longitudinal axes defined by the curves. As described in detail below, these varying axial extents cooperate to accommodate the unique demands on central articular area 282 through the range of prosthesis flexion.

Medial/lateral extent $ML_P$ is defined by proximal cylindrical surface 286, which corresponds to a deep-flexion portion of central articular area 282, i.e., that part of femoral cam 276 which contacts spine 278 during deep flexion of femoral component 220. In the context of the varying widths defined by central articular area 282, medial/lateral extent $ML_P$ is relatively small. In an exemplary embodiment, medial/lateral extent $ML_P$ may be as small as 1.5 mm or 3 mm, and may be as large as 3.5 mm or 5 mm, or may be any size within any range defined by the foregoing values. For example, in an exemplary family of femoral components having different component sizes, medial/lateral extent $ML_P$ may grow larger as the component sizes increase. In this exemplary family of components, medial/lateral extent $ML_P$ is between 10% and 25% of total intercondylar width $ML_T$, which in turn ranges from 14 mm to 22 mm.

By contrast, medial/lateral extent $ML_D$ is defined by distal cylindrical surface 290, which corresponds to an initial-flexion portion of central articular area 282. Medial/lateral extent $ML_D$ of distal cylindrical surface 290 is relatively larger than medial/lateral extent $ML_P$, and represents the largest medial/lateral extent of central articular area 282. In an exemplary embodiment, medial/lateral extent $ML_D$ may be as small as 12 mm, 14.8 mm or 15 mm, and may be as large as 16.1 mm, 19.5 mm or 20 mm, or may be any size within any range defined by the foregoing values. As best seen in FIG. 5A, posterior cylindrical surface 288 defines a steadily expanding medial/lateral extent which smoothly transitions from the narrower proximal medial/lateral extent $ML_P$ to the wider distal medial/lateral extent $ML_D$. For example, in the above-mentioned exemplary family of femoral components having different component sizes, medial/lateral extent $ML_D$ may grow larger as the component sizes increase. In this exemplary family of components, medial/lateral extent $ML_D$ is between 85% and 95% of total intercondylar width $ML_T$.

Lateral and medial transition areas 284L, 284M (FIG. 5C) flank central articular area 282 and extend laterally and medially to join articular area 282 to the adjacent lateral and medial condyles 224, 226, respectively. In an exemplary embodiment, medial and lateral transition areas 284M, 284L are mirror images of one another about a sagittal plane, i.e., the section plane of FIG. 5B which is parallel to and equidistant from lateral and medial condylar walls 238, 239. However, it is contemplated that differing transition areas may be employed as required or desired for a particular application.

Transition areas 284M, 284L define transition surfaces corresponding to the respective central articular surfaces to which they are adjoined. For example, FIG. 5C illustrates a representative coronal cross-section of femoral cam 276, in which the curvature of transitions areas 284M, 284L is depicted. Convex lateral and medial transition surfaces defining coronal radius $R_4$ flank the lateral and medial terminus of proximal central articular surface 286, forming a tangent with surface 286 and extending medially and laterally toward lateral and medial condyles 224, 226 respectively. In an exemplary embodiment, radius $R_4$ may be as small as 6 mm, 6.5 mm or 7 mm, and may be as large as 8 mm or 12 mm, or may be any size within any range defined by the foregoing values. In an exemplary family of prosthesis sizes, larger values for radius $R_4$ correspond to larger prosthesis sizes. Across all sizes, however, radius $R_4$ represents a significant portion of the total medial/lateral width $ML_T$. For example, radius $R_4$ may be equal to as little as 40%, 41% or 44% of total medial/lateral width $ML_T$, or may be as large as 46% or 56% thereof, or may be any percentage within any range defined by the foregoing values.

Referring still to FIG. 5C, the widely radiused and convex coronal curvature defined by radius $R_4$ gives way to a tighter concave curvature having radius $R_5$ as lateral and medial transitional areas 284L, 284M approach intersection with lateral and medial condyles 224, 226 respectively. This concave curvature is tangent to radius $R_4$ and to the adjacent surfaces of condyles 224, 226, thereby forming a smooth transition therebetween. Similarly, the portion of transition areas 284L, 284M which join distal and anterior surfaces 290, 292 (FIG. 5B) of femoral cam 276 to condyles 224, 226 are composed only of concave curvature having radius $R_6$, owing to the substantial width of surfaces 290, 292 (as discussed above). In an exemplary embodiment, both radius $R_5$ and radius $R_6$ are at least 1 mm. As noted above, all other radii defined by the surfaces of femoral cam 276 are substantially larger than 1 mm. Thus, femoral cam 276 defines a minimum radius of at least 1 mm at all parts subject to articulation with any adjacent soft tissues or prosthesis structures (i.e., excluding the portion of posterior bone-contacting surface 258, which only abuts the corresponding facet of the bone after implantation).

Moreover, the concave transitional radii $R_5$, $R_6$ are not generally considered a portion of the "articular" surfaces of femoral cam 276, because these concave surfaces will not come into contact with spine 278 of tibial bearing component 240 (FIG. 6). Rather, central articular area 282 and lateral and medial transitional areas 284L, 284M form the potential articular surfaces with regard to spine 278, and these areas combine to occupy a large proportion of total medial/lateral width $ML_T$. In an exemplary embodiment, the overall portion of total medial/lateral width $ML_T$ occupied by the combination of central articular area 282 and the convex portions of transition areas 284L, 284M is as little as 80%, 85% or 88%, and as much as 89% or 91%, or may be any percentage within any range defined by the foregoing values. Thus, only surfaces which are broadly convex and/or cylindrical are presented to surrounding tissues and anatomical structures, thereby maximizing surface area contact (and reducing contact pressure) between femoral cam 276 and spine 278 during articulation.

As illustrated in FIGS. 5A and 5B, femoral cam 276 is disposed between lateral and medial condyles 224, 226 near the proximal-most portion thereof. In use, the relative positioning of femoral cam 276 and tibial spine 278 results in initial contact therebetween in mid-flexion. As femoral component 220 as articulates with tibial bearing component 240 through the range of flexion, a portion of distal curve 290 initially contacts spine 278 along proximal contact line 294 (FIG. 6). In an exemplary embodiment, this initial contact occurs at a prosthesis flexion angle θ (FIG. 2A) of between 75 degrees and 93 degrees. In this mid-flexion configuration, external rotation of femoral component 220 has not yet begun, and the wide medial/lateral extent $ML_D$ of the cylindrical distal surface 290 is in articular contact with a comparably wide medial/lateral extent of proximal contact line 294 to provide a large contact area and associated low contact pressure.

As femoral component 220 transitions into deeper flexion orientations (i.e., larger flexion angles θ as shown in FIG. 2A), contact between femoral cam 276 and posterior articular surface 280 of spine 278 moves distally toward distal contact line 296 (FIG. 6). Simultaneously, the contact area on cam 276 transitions from distal surface 290, through posterior surface 288, and ultimately to proximal surface 286 once in deep flexion (e.g., when angle θ approaches and surpasses 155 degrees, as shown in FIG. 2A). In deep flexion, femoral component 220 also externally rotates, thereby altering the orientation of cylindrical surfaces 286, 288, 290 of femoral cam 276 with respect to posterior articular surface 280 of spine 278. To accommodate this altered orientation, posterior articular surface 280 angles or "turns" as cam 276 moves from proximal contact line 294 toward distal contact line 296. Thus, the anterior/posterior thickness defined by spine 278 along distal contact line 296 is greater near lateral articular compartment 246 as compared to the corresponding thickness near medial articular compartment 248.

This configuration of posterior articular surface 280 and attendant change in thickness is described in detail in: U.S. Provisional Patent Application Ser. No. 61/561,657, filed Nov. 18, 2011 and entitled "TIBIAL BEARING COMPONENT FOR A KNEE PROSTHESIS WITH IMPROVED ARTICULAR CHARACTERISTICS"; U.S. Provisional Patent Application Ser. No. 61/577,293, filed Dec. 19, 2011 and entitled "TIBIAL BEARING COMPONENT FOR A KNEE PROSTHESIS WITH IMPROVED ARTICULAR CHARACTERISTICS"; U.S. Provisional Patent Application Ser. No. 61/592,576, filed Jan. 30, 2012 and entitled "TIBIAL BEARING COMPONENT FOR A KNEE PROSTHESIS WITH IMPROVED ARTICULAR CHARACTERISTICS"; U.S. Provisional Patent Application Ser. No. 61/621,361, filed on Apr. 6, 2012 and entitled "TIBIAL BEARING COMPONENT FOR A KNEE PROSTHESIS WITH IMPROVED ARTICULAR CHARACTERISTICS"; U.S. Provisional Patent Application Ser. No. 61/621,363, filed on Apr. 6, 2012 and entitled "TIBIAL BEARING COMPONENT FOR A KNEE PROSTHESIS WITH IMPROVED ARTICULAR CHARACTERISTICS"; U.S. Provisional Patent Application Ser. No. 61/621,364, filed on Apr. 6, 2012 and entitled "TIBIAL BEARING COMPONENT FOR A KNEE PROSTHESIS WITH IMPROVED ARTICULAR CHARACTERISTICS"; U.S. Provisional Patent Application Ser. No.

61/621,366, filed on Apr. 6, 2012 and entitled "TIBIAL BEARING COMPONENT FOR A KNEE PROSTHESIS WITH IMPROVED ARTICULAR CHARACTERISTICS"; U.S. patent application Ser. No. 13/459,037, filed on Apr. 27, 2012, now issued as U.S. Pat. No. 8,858,643, and entitled "TIBIAL BEARING COMPONENT FOR A KNEE PROSTHESIS WITH IMPROVED ARTICULAR CHARACTERISTICS"; U.S. patent application Ser. No. 13,459,041, filed on Apr. 27, 2012, now issued as U.S. Pat. No. 9,072,607, and entitled "TIBIAL BEARING COMPONENT FOR A KNEE PROSTHESIS WITH IMPROVED ARTICULAR CHARACTERISTICS"; U.S. patent application Ser. No. 13/459, 048 filed on Apr. 27, 2012, now issued as U.S. Pat. No. 8,690,954, and entitled "TIBIAL BEARING COMPONENT FOR A KNEE PROSTHESIS WITH IMPROVED ARTICULAR CHARACTERISTICS"and U.S. patent application Ser. No. 13/459,056, filed Apr. 27, 2012, now issued as U.S. Pat. No. 8,764,838, and entitled "TIBIAL BEARING COMPONENT FOR A KNEE PROSTHESIS WITH IMPROVED ARTICULAR CHARACTERISTICS". The entire disclosures of each of the above-identified patent applications are hereby expressly incorporated herein by reference.

As external rotation of femoral component 220 initiates in deep flexion, engagement of posterior articular surface 280 of spine 278 shifts from distal surface 290 to posterior surface 288 of cam 276. As this shift takes place, the convex portions of transition areas 284M, 284L (described in detail above) move into position near the medial and lateral edges of posterior articular surface 280. As flexion (and external rotation) of femoral component 220 progresses, contact between femoral cam 276 and posterior articular surface 280 transitions from posterior surface 288 and to proximal surface 286. Proximal surface 286 defines a smaller medial/lateral width $ML_P$ compared to width $ML_D$ of distal surface 290 creating the medial/lateral space for the large-radius, broadly convex portions of transition areas 284M, 284L flanking proximal surface 286 (FIG. 5A). These large portions of transition areas 284M, 284L facilitate solid contact between the relatively narrower proximal surface 286 when femoral component 220 internally or externally rotates in deep flexion, thereby ensuring that a large area of contact and concomitantly low contact pressure between femoral cam 276 and tibial spine 278 is maintained.

Stated another way, the potential for internal/external rotation of femoral component 220 increases with increasingly deep flexion. Such internal/external rotation also causes the longitudinal axis of femoral cam 276 to rotate with respect to posterior surface 280 of tibial spine 278, thereby potentially misaligning one of cylindrical surfaces 286, 288 with posterior surface 280 (depending on the level of flexion). This misalignment is accommodated by the progressive narrowing of cylindrical surface 288 (and resulting narrow width $ML_P$ of proximal surface 286), which concomitantly increases the medial/lateral extent of transition areas 284M, 284L. The narrower cylindrical surfaces 286, 288 present a smaller area of contact with posterior surface 280 of spine 278, which in turn allows femoral cam 276 the requisite rotational freedom to accommodate internal/external rotation while maintaining area contact between the cylindrical surface of proximal surface 286 of femoral cam and the angled distal contact line 296 along posterior surface 280 of spine 278.

Advantageously, medial and lateral transition areas 284M, 284L provide a space or "trough" that is strategically located to accommodate the edges of spine 278 adjacent posterior articular surface 280, as femoral component 220 rotates externally and/or internally. This accommodation prevents any potential for impingement of cam 276 upon spine 278 in deep flexion. At the same time, radii $R_4$ are relatively large, thereby providing a widely rounded, convex and "soft tissue friendly" surface to reduce contact pressure in the event of soft tissue impingement upon transition areas 284L, 284M. Convex radii $R_5$ similarly eliminate any sharp edges in the vicinity of femoral cam 276, further minimizing potential contact pressures caused by impingements thereupon.

By contrast, predicate femoral components utilize an articular surface that is concave along its medial/lateral extent, and includes transition area radii that are substantially less than 1 mm. One such prior art femoral component forms a part of the NexGen LPS Flex prosthesis system (described above).

5. Soft Tissue Accommodation: Asymmetric Intercondylar Notch.

Figure 7:
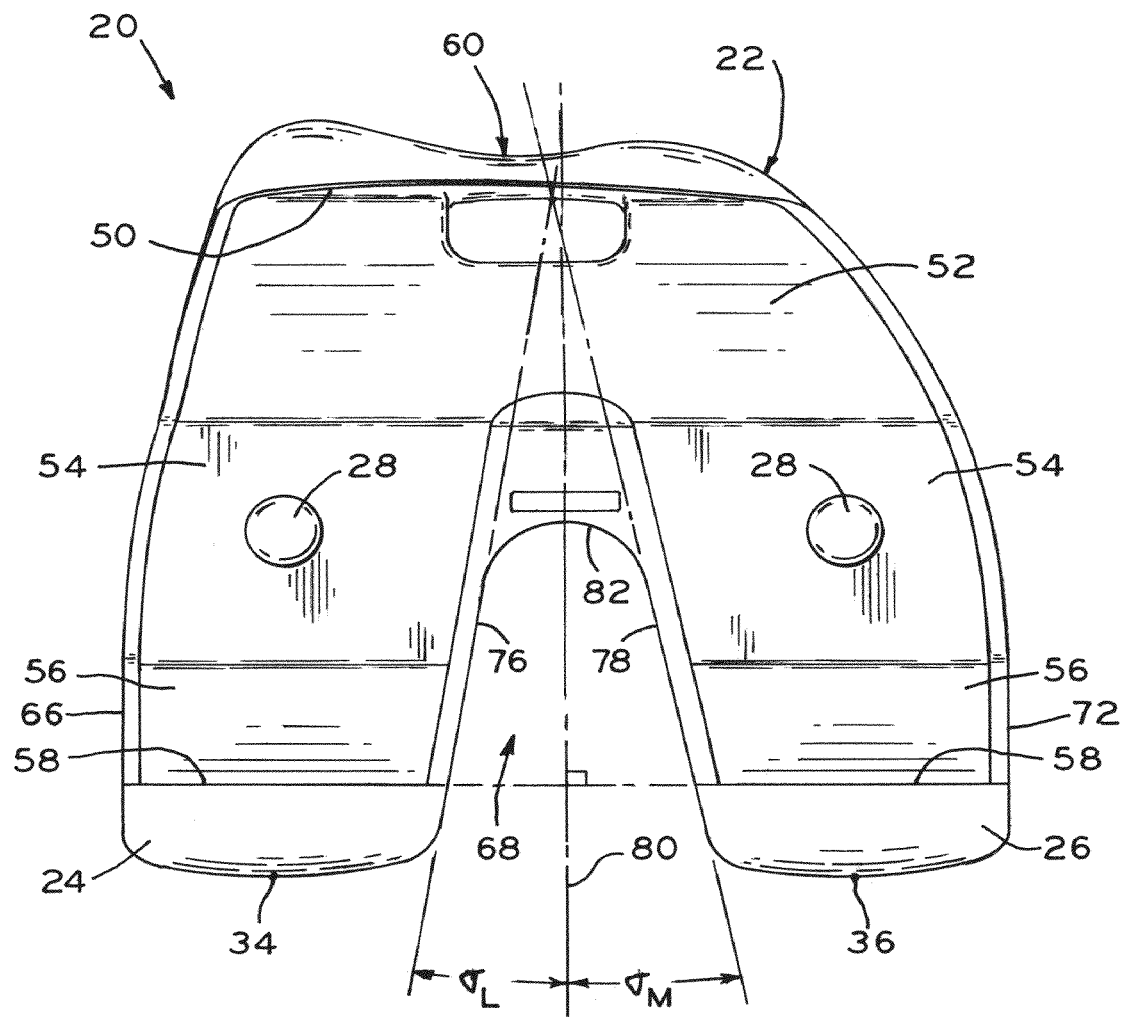
FIG. 7 is a proximal plan view of a femoral component made in accordance with the present disclosure.

Referring to FIG. 7, for cruciate retaining (CR) femoral component designs, such as femoral component 20, intercondylar notch 68 is laterally and medially bounded by lateral inner sidewall 76 and medial inner sidewall 77, respectively. As described in detail below, inner sidewalls 76, 77 define angular orientations with respect to femoral component 20 which operate to protect the posterior cruciate ligament (PCL) during prosthesis articulation. As noted above, the PCL is retained in the surgical procedure implanting cruciate retaining femoral component 20 and associated prosthesis components.

Referring to FIG. 7, femoral component 20 defines bisecting axis 80, which divides femoral component 20 into medial and lateral halves. In the context of component 20, bisecting axis 80 bisects the arcuate anterior terminus 82 of intercondylar notch 68, and is perpendicular to a posterior coronal plane defined by posterior bone contacting surface 58. However, it is contemplated that bisecting axis 80 may be defined in a number of other ways, provided that axis 80 generally divides a femoral component made in accordance with the present disclosure into medial and lateral halves. In the context of patient anatomy, bisecting axis 80 corresponds to Whiteside's line when implanted onto a femur. Whiteside's line is defined as the line joining the deepest part of the anatomic patellar groove, anteriorly, and the center of the anatomic intercondylar notch, posteriorly.

Lateral inner sidewall 76 defines angle $\sigma_L$ with respect to bisecting axis 80, while medial sidewall 77 defines angle $\sigma_M$ with respect to bisecting axis 80. Intercondylar notch 68 may be said to be "asymmetric" because medial sidewall angle $\sigma_M$ is greater than lateral sidewall angle $\sigma_L$. Advantageously, this asymmetric angular arrangement of sidewalls 76, 77 of intercondylar notch 68 facilitates external rotation of femoral component 20 in deep flexion (described in detail above) by providing additional space for the posterior cruciate ligament on the medial side. This additional medial space avoids potential contact between the PCL and medial inner sidewall 77 which might otherwise occur when femoral component 20 externally rotates.

6. Soft Tissue Accommodation: Rounded Anterior Flange.

FIG. 8 illustrates a cross-section of anterior flange 22 of femoral component 20. As illustrated in FIG. 1B, the cross-sectional profile of FIG. 8 is taken at the junction of anterior bone-contacting surface 50 and anterior chamfer surface 52 (and through the middle of thickness ridge 300, as described below). The plane of the FIG. 8 cross section is taken generally perpendicular to the adjacent surfaces, i.e., such that the minimum material thicknesses are shown. For simplicity, the geometric features of anterior flange 22 are described with reference to the cross section of FIG. 8, it being understood that such geometric features also propagate through the remainder of anterior flange 22.

As shown in FIG. 8, anterior flange 22 includes lateral condylar portion 62 and medial condylar portion 63, with a concave patellar groove 60 disposed therebetween. As noted above, a natural or prosthetic patella articulates with the concave patellar groove 60 during prosthesis articulation. During such articulation, lateral and medial condylar portions 62, 63 provide constraint to medial and lateral movement of the patella. The level of medial/lateral constraint depends in part on "jump heights" $JH_L$, $JH_M$, defined by condylar portions 62, 63. Jump heights $JH_L$, $JH_M$, illustrated in FIG. 8, represent the amount of anterior travel, i.e., travel outwardly away from patellar groove 60, that a patella would have to traverse in order for subluxation of the patella component from the lateral and medial sides of anterior flange 22, respectively to occur. In anterior flange 22, jump heights $JH_L$, $JH_M$ are arranged to prevent such subluxation under normal operating conditions of the prosthesis. In an exemplary embodiment, medial jump height $JH_M$ is between 3.0 mm and 4.6 mm and lateral jump height $JH_L$ is between 3.5 mm and 5.7 mm. These jump height value ranges are comparable to the prior art femoral components of the Zimmer NexGen prosthesis series, e.g., the NexGen CR Flex prosthesis system and the NexGen LPS Flex prosthesis system.

Anterior flange 22 defines large-radius, convex lateral and medial condylar portions 62, 63 respectively. Lateral edge 98 extends from peak 62P of the convex lateral condylar portion 62, to the lateral edge of anterior bone contacting surface 50. Similarly, medial edge 99 extends from peak 63P of the convex medial condylar portion 63 to the medial edge of anterior bone contacting surface 50. Peaks 62P, 63P cooperate with patellar groove 60 to define lateral jump height $JH_L$, $JH_M$ respectively, as illustrated in FIG. 8. As compared with alternative anterior flange profiles (schematically illustrated in FIG. 8 using dashed lines), anterior flange 22 includes lateral and medial edges 98, 99 which define larger radii of curvature $R_7$, $R_8$, respectively. These large radii of curvature $R_7$, $R_8$ advantageously present a large, convex surface which minimizes pressure applied to adjacent soft tissues such as the retinaculum and extensor mechanism. In an exemplary embodiment, radius $R_7$ is equal to radius $R_8$, with each of radii $R_7$, $R_8$ sized as small as 5.0 mm, 5.3 mm or 5.5 mm and as large as 6.5 mm, 6.8 mm or 7.0 mm, or are any size within any range defined by any of the foregoing values.

In some instances, the radii defined by the cross-sectional profile of patellar groove 60 are larger than radii $R_7$, $R_8$, such that the smallest radii presented across the entire medial/lateral extent $ML_G$ of the articular surface of anterior flange 22 are radii $R_7$, $R_8$. In these instances, no small radii are potentially presented to any adjacent soft tissues.

Moreover, these radii represent a large proportion of the overall medial/lateral width $ML_G$ (FIG. 8) of anterior flange 22 at any given medial/lateral cross-section. For example, at the cross-section of FIG. 8, medial/lateral flange width $ML_G$ ranges from 37 to 53 mm across a family of prosthesis sizes, such that radii $R_7$, $R_8$ each define between 10% and 16% of overall medial/lateral width $ML_G$ of anterior flange 22.

By contrast, the corresponding radii defined by the prior art femoral components of the Zimmer NexGen CR Flex prosthesis system define medial and lateral flange radii (analogous to radii $R_7$, $R_8$ of the present prosthesis) of between 2.0 mm and 2.6 mm across a range of seven nominal prosthesis sizes. Each of these prior art radii define between 3.5% and 5.9% of the overall medial/lateral width (analogous to width $ML_G$ of the present prosthesis) of the respective anterior flanges of the prior art femoral components.

7. Bone Conservation: Uniform Thickness of Anterior Flange.

FIG. 9A illustrates femoral component 20 having thickness ridge 300, which is disposed on the bone-contacting side of anterior flange 22 and spans across portions of anterior bone contacting surface 50 and anterior chamfer surface 52. As described in detail below, thickness ridge 300 defines a sagittally-oriented peak 302, which advantageously allows minimum thicknesses $T_T$ (FIG. 8), $T_S$ (FIG. 10A) in anterior flange 22 to be maintained while preserving a surgeon's ability to implant femoral component 20 on a distal femur with planar anterior and anterior chamfer facet cuts.

Figure 9B:
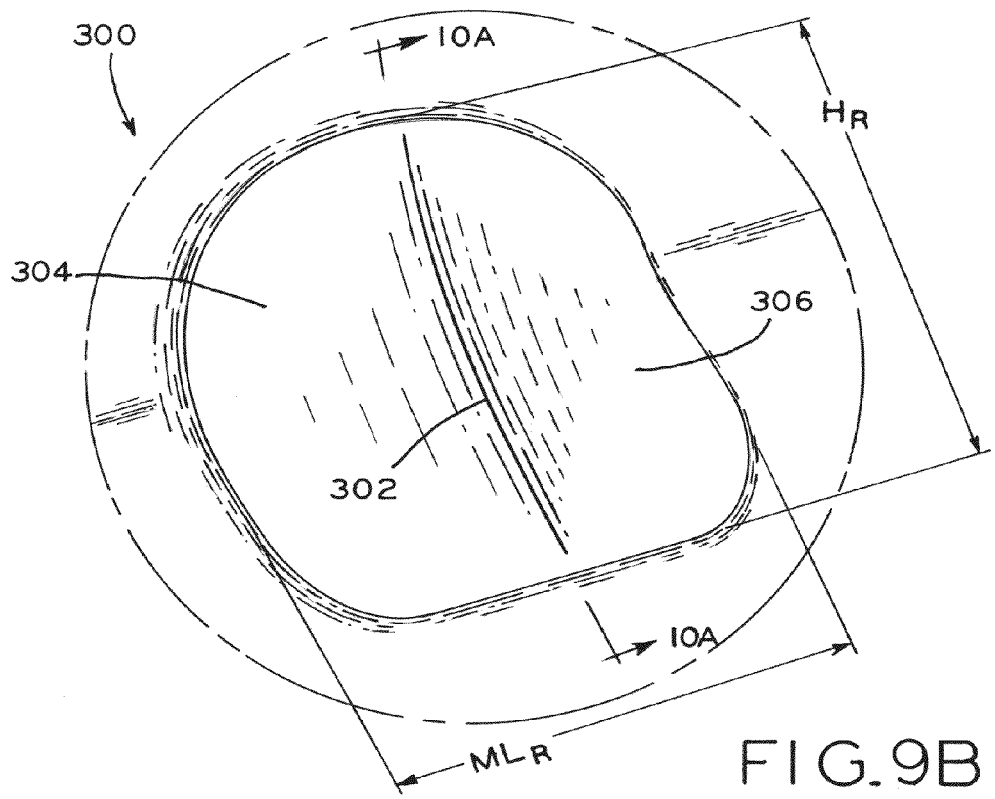
FIG. 9B is a partial, enlarged view of a portion of the femoral component shown in FIG. 9A.
Figure 10A:
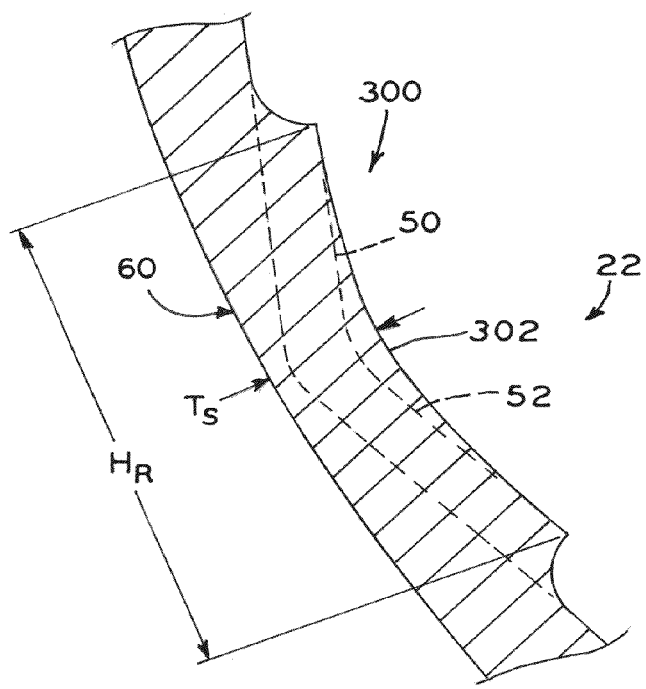
FIG. 10A is a sagittal elevation, cross-sectional view of a portion of the femoral component shown in FIG. 9A, taken along line 10A-10A of FIG. 9B.

Turning to FIG. 9B, thickness ridge 300 includes ramped lateral facet 304 and ramped medial facet 306, which gradually ascend toward one another to meet at peak 302. By contrast, a non-peaked thickness ridge may include a single flat surface (illustrated schematically as surface 300' in FIG. 8), which extends medially/laterally without any peaked structure. Viewed from a sagittal perspective, such as shown in FIG. 10A, such non-peaked thickness ridge would follow the inner sagittal profile of anterior bone contacting surface 50 and anterior chamfer surface 52 (shown in dashed lines). In contrast, as best seen in FIGS. 10A and 10B, peak 302 of thickness ridge 300 protrudes inwardly from bone contacting surface 50 and anterior chamfer surface 52. In an exemplary embodiment, the amount of such inward protrusion may be up to 1.5 mm to allow for implantation of femoral component 20 upon a bone with planar resected surfaces, as discussed below.

Bone-contacting surfaces 50, 52, 54, 56, 58 (FIG. 9A) each extend from a lateral edge to a medial edge of femoral component 20. Posterior surface 58 and posterior chamfer surface 56 are each interrupted by intercondylar notch 68, such that surfaces 56, 58 each extend from the medial edge of condyle 26 to medial condylar wall 39, and from the lateral edge of lateral condyle 24 to lateral condylar wall 38. Together, bone-contacting surfaces 50, 52, 54, 56, 58 define the inner sagittal profile of femoral component 20, which is the profile as it appears when the medial and lateral edges are superimposed over one another (i.e., aligned as illustrated in FIG. 1B).

Referring still to FIG. 9A, femoral component 20 includes lateral and medial rails 59L, 59M which bound recessed pocket 31 adapted to receive bone cement, porous material, or other fixation material (e.g., fixation material 33 as shown in FIG. 10B) for adhering femoral component 20 to the distal femur upon implantation. Where rails 59L, 59M are provided, rails 59L, 59M are considered to define the inner sagittal periphery of femoral component 20 rather than the recessed profile of pocket 31.

Advantageously, peaked thickness ridge 300 allows for transverse thickness $T_T$ (FIG. 8) and sagittal thickness $T_S$ (FIG. 10A) to be maintained above a desired minimum thickness by providing extra material following the path of patellar groove 60 (FIG. 8). Thicknesses $T_T$, $T_S$ are measured as the shortest distance between the trough of patellar groove 60 (described above) and peak 302, and are equal when measured between common points. The extra material provided by peak 302, corresponds with the profile of the deepest portion of the trough defined by groove 60. In the exemplary embodiment illustrated in the drawings, this deepest portion of groove 60 is also the portion that defines a series of points closest to the adjacent anterior and anterior-chamfer bone-contacting surfaces 50, 52 (e.g., FIGS. 7 and 8). Thus, what would normally be the thinnest portion of anterior flange 22 is made thicker by peak 302. The overall minimum thickness of anterior flange 22 may be as little as 1 mm, 1.1 mm or 1.3 mm and may be as large as 1.8 mm, 1.9 mm or 2 mm, or may be any thickness within any range defined by any of the foregoing values. Generally speaking, larger prosthesis sizes have larger minimum thicknesses. Thicknesses $T_T$, $T_S$, are at least as large as, or greater than, the minimum.

Moreover, as illustrated in FIGS. 8 and 10A, the overall thickness of anterior flange 22 is also more consistent across the medial/lateral and proximal/distal extent of anterior flange 22, as compared with a thickness ridge having surface 300' with a flat medial/lateral profile. This consistent thickness allows for the overall average thickness of anterior flange 22 to be reduced to a value closer to the desired minimum thickness, rather than providing the minimum thickness only near patellar groove 60 and excess thickness in the remainder of flange 22. This reduction in average flange thickness allows for reduced bone resection in the anterior facet and anterior chamfer, thereby facilitating preservation of healthy bone stock. Further maintaining uniformity of thickness across medial/lateral extent $ML_G$ facilitates manufacture of femoral component 20 by allowing for more even, consistent dissipation of heat, such as after forming, forging and machining operations.

The uniformity of thickness across the medial/lateral cross-section of anterior flange 22 may be expressed as the maximum deviation of any given thickness dimension as a percentage of the average thickness. In an exemplary embodiment, this deviation may be as little as 38%, 39% or 44% and as large as 55%, 58% or 65% of the average thickness, or may be any percentage of the average thickness within any range defined by any of the foregoing values. The nominal range of average thicknesses across the range of prosthesis sizes is between 2.2 mm and 3.7 mm. The above-mentioned thicknesses take into account the presence of recessed pocket 31, which defines recess depth $D_R$ of between 1.1 and 1.2 mm.

By contrast, the prior art Zimmer NexGen CR Flex prosthesis system includes femoral components exhibit a corresponding maximum thickness deviation of between 35% and 46%, with the nominal range of average thicknesses across a range of prosthesis sizes being between 3.4 mm and 4.4 mm.

Peak 302 defines a relatively sharp edge along its longitudinal extent (FIG. 9B). In an exemplary embodiment, this sharp edge is manufactured as an edged surface, such that the edge defines no appreciable radius as viewed in the medial/lateral cross section of FIG. 8. Because peak 302 protrudes inwardly from bone contacting surface 50 and anterior chamfer surface 52 (as viewed from the sagittal perspective of FIG. 10A), this sharp edge operates to compact adjacent bone of the anterior facet and anterior chamfer facet when femoral component 20 is implanted on a distal femur. Such compaction is shown in FIG. 10B, where peak 302 is shown extending into the anterior and anterior chamfer facets of resected femur F. More particularly, referring to FIG. 10C, femur F may be prepared with planar anterior facet AF and planar anterior chamfer facet ACF. Once femoral component 20 is implanted upon femur F as shown in FIG. 10B, indentation I mimicking thickness ridge is formed by local compaction of bone on facet AF and planar anterior chamfer facet ACF, thereby disrupting the planarity of facets AF, ACF in the region of indentation I.

As compared with flat a prior art surface (shown schematically as surface 300', shown in FIG. 8 and described above), the additional volume of bone displaced by the edge defined by peak 302 and the associated elevation of lateral and medial facets 304, 306 is minimal. In an exemplary embodiment, the displaced volume may be as little as 0.8 mm³, 1.2 mm³ or 1.5 mm³ and as large as 13.5 mm³, 13.7 mm³ or 13.8 mm³, or may be any volume within any range defined by any of the foregoing values. Moreover, the maximum inward protrusion of the edged peak 302 is 1.5 mm past the sagittal geometry of anterior bone-contacting surface 50 and anterior chamfer surface 52, as noted above.

Figure 10D:
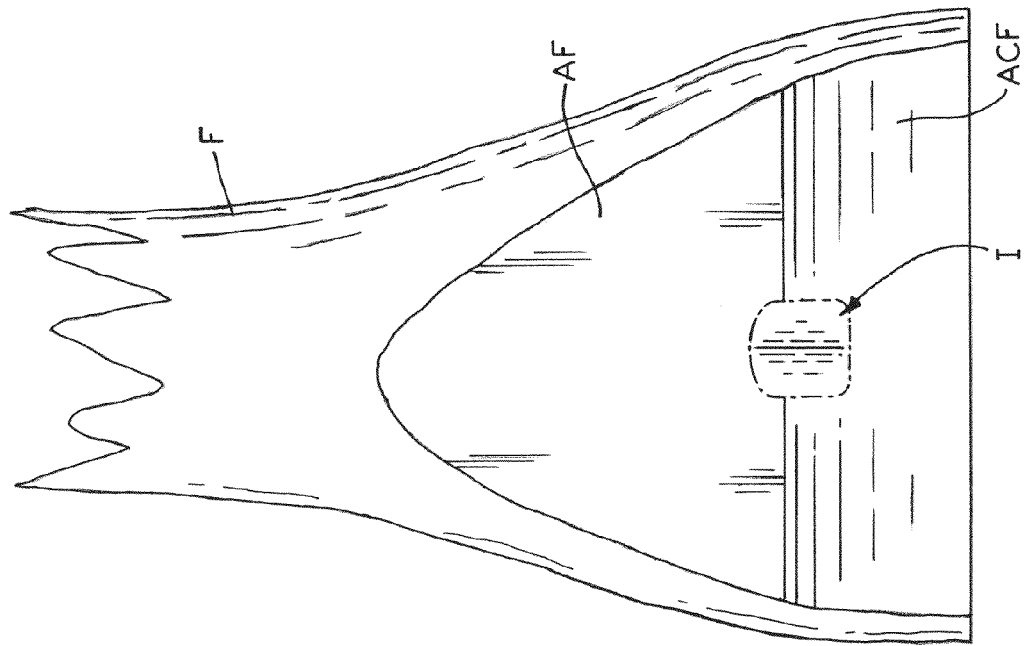
FIG. 10D is an anterior elevation view of the femur shown in FIG. 10B, after implantation of the femoral component.
Figure 10C:
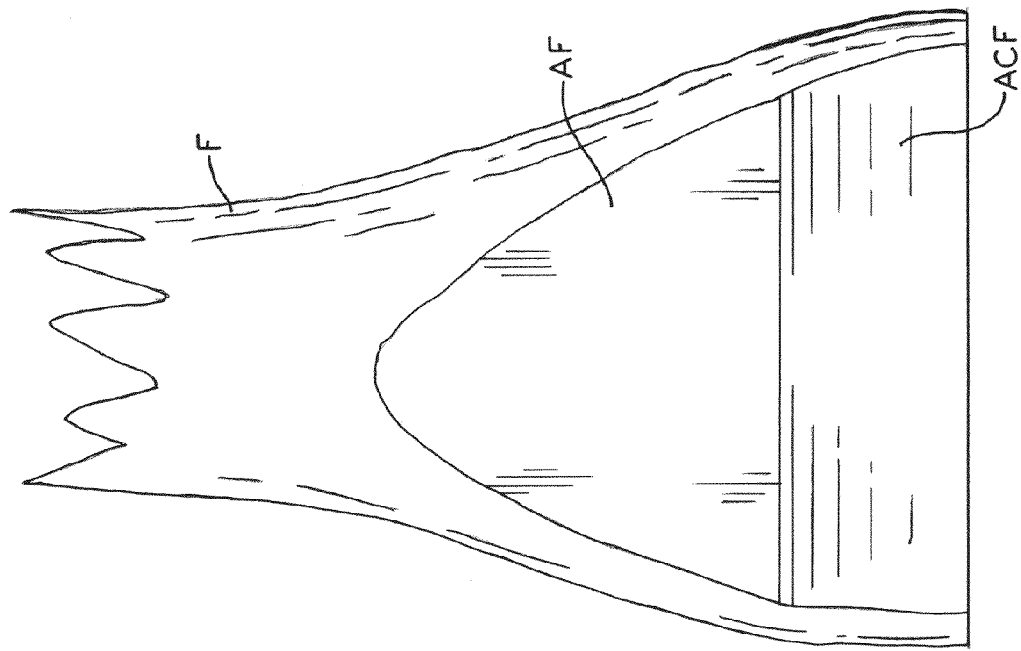
FIG. 10C is an anterior elevation view of the femur shown in FIG. 10B, prior to implantation of the femoral component.

Thus, the cancellous or cortical bone of the planar resected anterior and anterior chamfer facets is easily compacted upon implantation of femoral component 20 to accommodate such additional volume. A surgeon may make facet cuts in the femur which are substantially planar (as shown in FIG. 10C), thereby simplifying the surgical procedure. These facet cuts may, for example, include five cuts to create five facets sized to receive anterior, anterior chamfer, distal, posterior chamfer and posterior bone-contacting surfaces 50, 52, 54, 56, 58. Femoral component 20 is provided by the surgeon, who then implants femoral component 20 on the resected femur along a distal-to-proximal direction, until peaked portion 302 of thickness ridge 300 compresses the adjacent bone fully (as shown in FIG. 10B). When such full compression has occurred, indentation I is formed (FIG. 10D) such that the entire periphery of thickness ridge 300 will be in contact with the adjacent facets of the bone.

Optionally, to further ease bone compaction to accommodate peak 302, additional resection of the bone at the intersection of the anterior facet and anterior chamfer facet may be performed. For example, a small osteotomy in the vicinity of peak 302 may be made prior to implantation, such as with a small saw blade, so that peak 302 sits within the osteotomy upon implantation. Similarly, a small hole may be made in this area, such as with a drill. However, testing performed by Applicants has revealed that no such osteotomy is necessary, and peak 302, lateral facet 304 and medial facet 306 all seat firmly and completely on cortical and cancellous bone upon implantation.

An additional advantage conferred by peak thickness ridge 300 is additional medial/lateral fixation of femoral component 20 upon implantation. Once peak 302 has impacted the abutting bone, such facets are no longer planar but instead include a ridge-shaped depression occupied by peak 302. Thus, lateral and medial facets 304, 306 act as barriers to medial and lateral translation of femoral component 20, and thereby confer additional medial/lateral stability. This additional stability aids in secure component fixation, particularly initially after implantation.

It is contemplated that the overall size and geometry of thickness ridge 300 may be constant across multiple femoral sizes, or may grow and shrink as femoral sizes grow larger or smaller. In an exemplary embodiment, twelve femoral sizes are provided (as described in detail below), with the ten largest sizes including thickness ridge 300 having a common size, shape and volume across all ten sizes. For the smallest sizes, a reduced-size thickness ridge 300A (FIG. 12A) may be used.

Overall medial/lateral extent $ML_R$ (FIGS. 8 and 9B) and proximal/distal height $H_R$ (FIGS. 9B and 10A) are calculated to be as small as possible while maintaining a minimum desired thickness across the entirety of anterior flange 22 (as discussed above). In an exemplary embodiment, proximal/distal height $H_R$ may be as little as 7.4 mm and as large as 14.5 mm, 14.6 or 15.0 mm, or may be any height within any range defined by any of the foregoing values. Medial/lateral extent $ML_R$ may be as little as 12.5 mm and as large as 15.0 mm, 15.1 or 15.5 mm, or may be any volume within any range defined by any of the foregoing values. Within these dimensional bounds, the overall peripheral shape of thickness ridge 300 is designed to follow the contours of anterior flange 22, advantageously providing visual acuity therebetween.

For example, the changes in geometry for narrow anterior flange 122 of narrow femoral component 120 result in corresponding changes to the overall shape of the corresponding thickness ridge (not shown), thereby providing visual acuity with the narrow shape of component 120. However, the overall coverage area and design principles of thickness ridge 300 apply to any femoral component made in accordance with the present disclosure.

Advantageously, maintaining medial lateral width $ML_R$ and proximal/distal height $H_R$ at minimum values serves to maximize the area on anterior bone contacting surface 50 and anterior chamfer surface 52 for fixation material, as described in detail below.

8. Bone Conservation: Intercondylar Notch with Sloped Sidewalls.

Figure 11A:
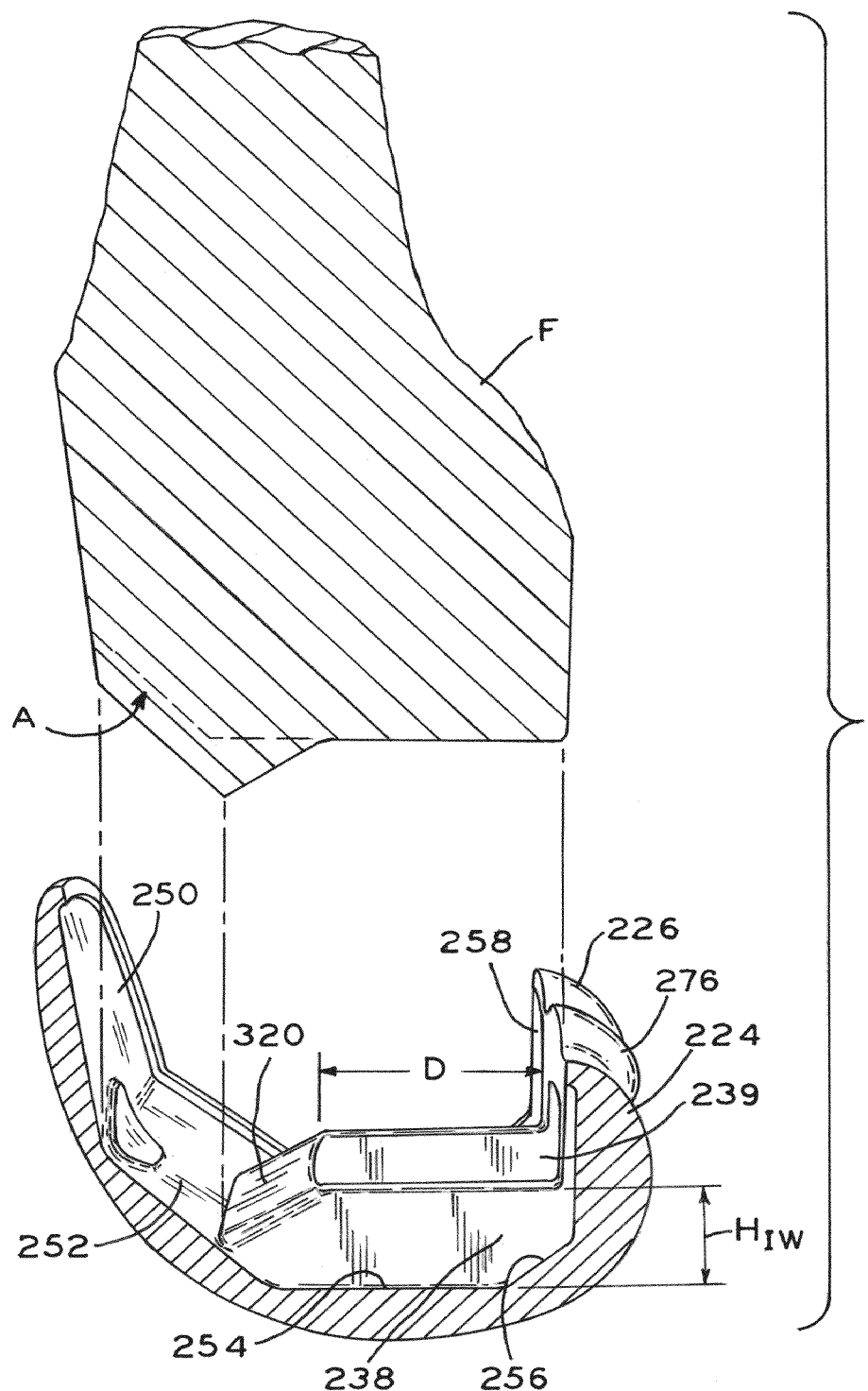
FIG. 11A is a sagittal elevation, cross-sectional view of a femoral component made in accordance with the present disclosure, shown with a femur resected to receive the femoral component.

FIGS. 11A and 11B illustrate a sagittal cross-sectional view of posterior stabilized femoral component 220, both before and after implantation upon resected femur F. The cross section of FIGS. 11A and 11B are taken along the outer (i.e., lateral-facing) surface of lateral wall 238 of intercondylar notch 268. A similar cross-sectional view, taken at the medially-facing side of medial wall 239 of intercondylar notch 268, would be a mirror image of FIGS. 11A and 11B. As illustrated, lateral wall 238 extends proximally from distal bone-contacting surface 254 to define a height $H_{IW}$ along the proximal/distal direction (e.g., the direction perpendicular to distal bone contacting surface 254).

A posterior portion of wall 238 defines proximal edges (extending along distance D of FIGS. 11A and 11B) which are substantially parallel with distal bone-contacting surface from the sagittal perspective of FIG. 11A, while lateral wall 238 includes a downwardly sloping (i.e., in a distal direction) anterior portion 320. In an exemplary embodiment, the posterior and anterior portions define an overall anterior/posterior extent of between 35 mm and 54 mm. The downward sloping anterior portion 320 initiates at a distance D spaced anteroposteriorly from posterior bone contacting surface 258, which is between 27 mm and 48 mm in the exemplary embodiment. Both distance D and the overall anterior/posterior extent grow as sizes grow within a family of prosthesis sizes; across such a family of prosthesis sizes, distance D represents between 77% and 89% of the overall anterior/posterior extent of wall 238.

Distance D is calculated to provide sufficient proximal/distal wall height across the posterior portion of intercondylar notch 268, such that impingement of femur F upon spine 278 of tibial bearing component 240 (FIG. 6) is avoided throughout the prosthesis range of motion.

Similarly, the angle 322 of sloped portion 320, taken with respect to a transverse plane (which, in the illustrated embodiment, is parallel to distal bone contacting surface 254), is also calculated to prevent spine 278 from extending proximally beyond walls 238, 239 throughout the range of prosthesis motion. In extension, spine 278 sits between the non-sloped portions of walls 238, 239 occupied by distance D (FIG. 11A). As flexion progresses, the proximal tip of spine 278 advances toward sloped portion 320 as femoral component 220 rotates with respect to tibial bearing component 240. Angle 322 is calculated to provide space above the proximal tip of spine 278 in deep flexion, while avoiding unnecessary resection of bone. Depending on the geometry of spine 278 and the particular articular characteristics of the prosthesis, angle 322 may be any acute angle greater than zero but less than 90 degrees. In an illustrative embodiment of FIGS. 11A and 11B angle 322 is 60 degrees. The anterior location and gentle slope of anterior portion 320 cooperate to position the anterior terminus of sloped potion 320 at anterior chamfer 252. As shown in FIGS. 11A and 11B, sloped portion 320 terminates into anterior chamfer 252.

Advantageously, positioning the terminus of sloped portion 320 in a relatively anterior location, i.e., at anterior chamfer 252, prevents the junction between walls 238, 239 and the adjacent bone-contacting surfaces (252, 254, 256, 258) from interfering with any portion of intercondylar notch 268. By contrast, for example, a very steep or vertical angle 322 for sloped portion 320 would cause sloped portion 320 to terminate into an area occupied by intercondylar notch 268, potentially necessitating a change in the geometry and/or location of intercondylar notch 268.

Advantageously, sloped portion 320 preserves bone stock of femur F within area A in the anatomic intercondylar notch, thereby reducing the amount of bone which must be removed upon implantation of femoral component 220. By contrast, anterior sagittal profile 320', which excludes anterior sloped portion 320 and extends anteriorly along the same profile as the top of lateral wall 238, would necessitate the removal of the bone within area A. Although femur F is shown in FIGS. 11A and 11B as having resection profiles that follow the sagittal profile of intercondylar walls 238, 239, it is contemplate that in certain exemplary procedures the portion of the bone resection corresponding to sloped portion 320 may be extrapolated to the posterior facet (thereby yielding a substantially planar distal facet).

9. Bone Conservation: Intercondylar Fixation Lug.

For posterior stabilized femoral prosthesis designs, e.g., those including a femoral cam which articulates with a tibial bearing component spine during articulation, fixation pegs 28 (FIG. 1B) may be omitted in favor of utilizing lateral and medial walls 238, 239 of intercondylar notch 268 for fixation of femoral component 220 to the femur.

Figure 12A:
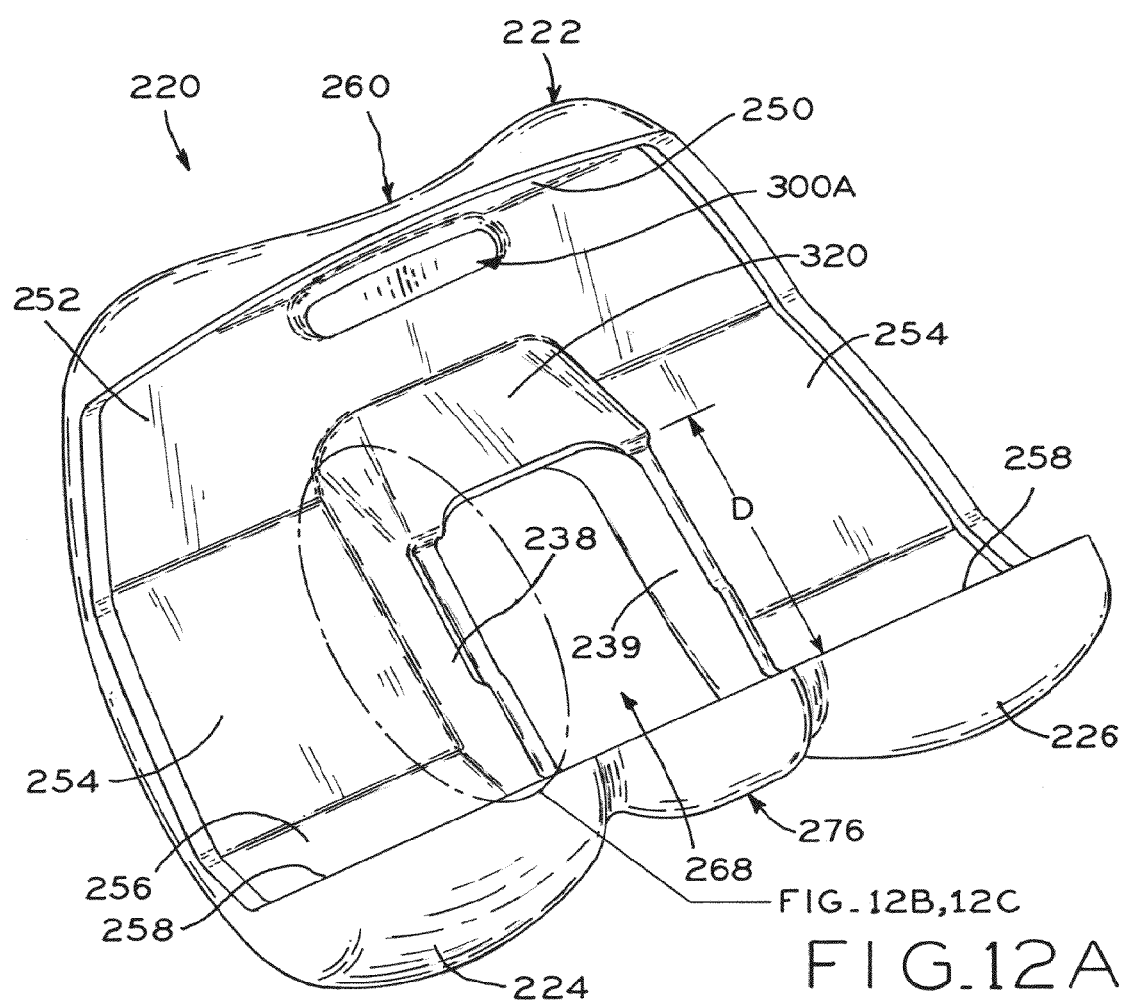
FIG. 12A is a proximal perspective view of a femoral component made in accordance with the present disclosure.

For example, FIG. 12A shows femoral component 220 in a relatively smaller component size which omits fixation pegs, instead offering uninterrupted distal bone contacting surfaces 254. In order to fix component 220 to femur F (FIGS. 11A and 11B), a function normally provided in part by pegs 28, walls 238, 239 of intercondylar notch 268 may double as a fixation device. For example, a close tolerance between the central lug defined by walls 238, 239 and the adjacent resected bone within the anatomic intercondylar notch may result in a friction-fit therebetween, thereby providing axial fixation of component 220 to femur F. In an exemplary embodiment, femoral component 220 including such a central lug is implanted onto a femur with a nominal clearance of 0.76 mm, and a range of clearances between 0.43 mm and 1.49 mm. These clearances may be provided through use of an appropriately sized cut guide designed for resection of the anatomic interconylar fossa.

Advantageously, these exemplary clearances allow walls 238, 239 to be used as an axial fixation structure as described above, while maintaining acceptable stresses on the surrounding bone upon implantation of femoral component 220. Further, because the natural intercondylar notch naturally defines an anatomic void, use of walls 238, 239 for fixation allows for only minimal resection of bone around the periphery of the existing void, rather than creation of an entirely new void within the bone stock of the distal femur.

Referring now to FIG. 12B, for example, lateral wall 238 may include recessed cement pocket 330 formed therein. Medial wall 239 may include a similar, laterally facing recessed cement pocket (not shown). When femoral component 220 is implanted upon femur F, bone cement or porous fixation material may be disposed in the lateral and medial cement pockets 330 for fixation to the adjacent, resected bone within the intercondylar notch of the femur to augment the fixation of femoral component 220 at bone contacting surfaces 250, 254, 258 and chamfers 252, 256.

For example, pockets 330, bone contacting surfaces 250, 254, 258 and/or chamfers 252, 256 may be at least partially coated with a highly porous biomaterial to facilitate firm fixation thereof to the abutting resected surfaces of the distal femur. A highly porous biomaterial is useful as a bone substitute and as cell and tissue receptive material. A highly porous biomaterial may have a porosity as low as 55%, 65%, or 75% or as high as 80%, 85%, or 90%, or may have any porosity within any range defined by any of the foregoing values. An example of such a material is produced using Trabecular Metal™ Technology generally available from Zimmer, Inc., of Warsaw, Ind. Trabecular Metal™ is a trademark of Zimmer, Inc. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861 to Kaplan, the entire disclosure of which is hereby expressly incorporated herein by reference. In addition to tantalum, other metals such as niobium, or alloys of tantalum and niobium with one another or with other metals may also be used.

Generally, the porous tantalum structure includes a large plurality of struts (sometimes referred to as ligaments) defining open spaces therebetween, with each strut generally including a carbon core covered by a thin film of metal such as tantalum, for example. The open spaces between the struts form a matrix of continuous channels having no dead ends, such that growth of cancellous bone through the porous tantalum structure is uninhibited. The porous tantalum may include up to 75%, 85%, or more void space therein. Thus, porous tantalum is a lightweight, strong porous structure which is substantially uniform and consistent in composition, and closely resembles the structure of natural cancellous bone, thereby providing a matrix into which cancellous bone may grow to provide fixation of implant 10 to the patient's bone.

The porous tantalum structure may be made in a variety of densities in order to selectively tailor the structure for particular applications. In particular, as discussed in the above-incorporated U.S. Pat. No. 5,282,861, the porous tantalum may be fabricated to virtually any desired porosity and pore size, and can thus be matched with the surrounding natural bone in order to provide an improved matrix for bone ingrowth and mineralization.

Alternatively, as shown in FIG. 12C, the laterally facing surface of lateral wall 238 may include surface texture 332 to aid in initial and long term fixation of femoral component 220 to bone. Surface texture 332 may include knurling, striations or scales, or any other suitable texture. Similar to cement pocket 330, surface texture 332 may also be provided on the medially facing surface of medial wall 239, such that surface texture 332 abuts resected bone in the intercondylar notch of femur F when femoral component 220 is implanted.

Omitting fixation pegs 28 and utilizing walls 238, 239 of intercondylar notch 268 is particularly advantageous in the context of small component sized for use with small stature patients. In these instances, a limited amount of distal bone area is available for fixation of femoral component 220, which may leave insufficient fixation space between fixation pegs 28 and walls 238, 239 of intercondylar notch 268. By omitting femoral fixation pegs 28 and instead using walls 238, 239 for fixation as described above, additional natural bone may be preserved to provide enhanced structural integrity and robustness of the distal femur.

For small stature patients, the medial/lateral width or gap between lateral and medial walls 238, 239 of intercondylar notch 268 may be reduced. This may allow for walls 238, 239 to have increased contact with cortical bone in a relatively narrower anatomic intercondylar notch typical of small stature distal femurs.

Figure 12D:
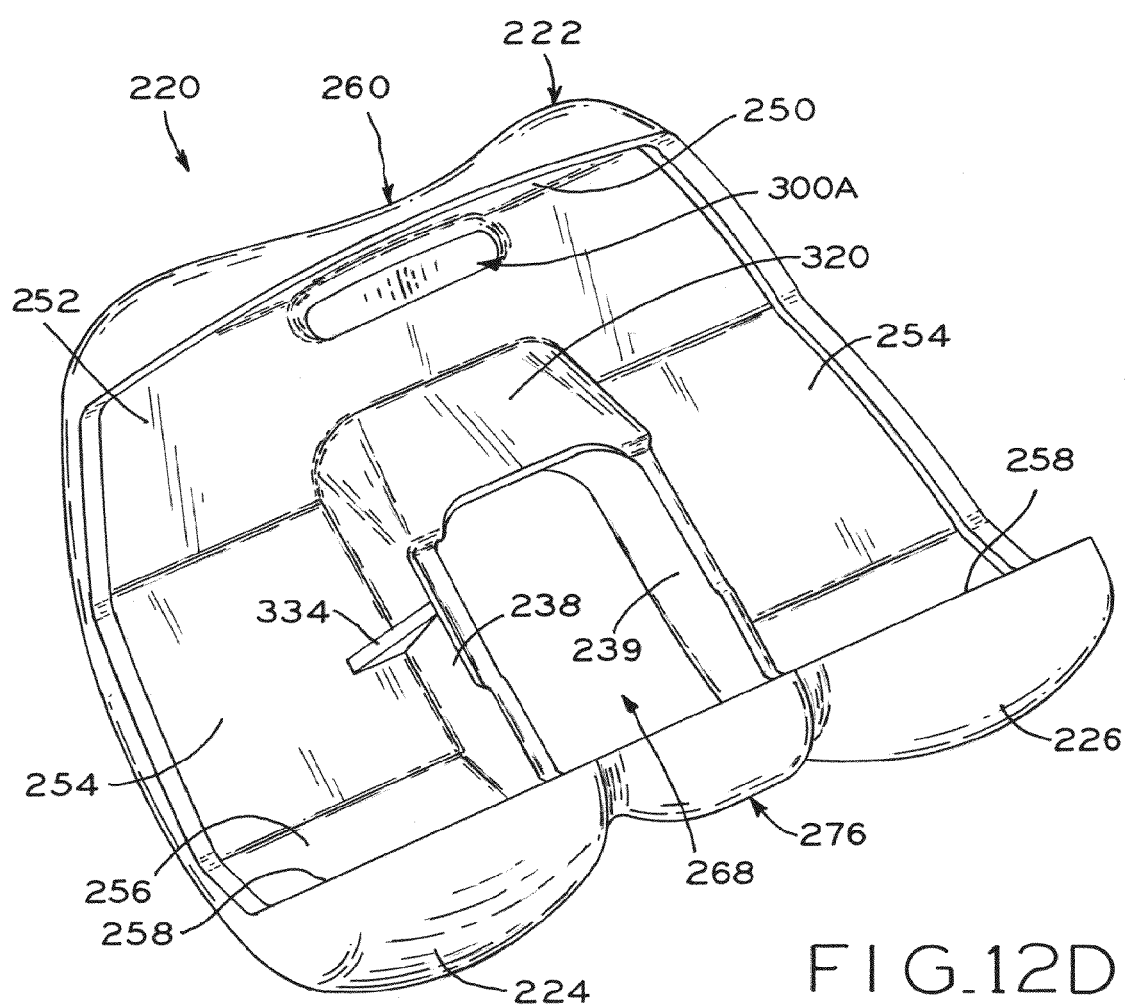
FIG. 12D is a proximal perspective view of another femoral component made in accordance with the present disclosure.

Referring now to FIG. 12D, an optional auxiliary fixation lug 334 may be provided to further enhance fixation of femoral component 220 to the femur. Auxiliary lug 334 extends laterally from the lateral face of lateral wall 238, and spans the angular corner formed by lateral wall 238 and the adjacent portion of distal bone contacting surface 254, thereby forming a fin-like structure protruding outwardly from wall 238. A similar auxiliary fin (not shown) may also extend medially from the medial face of medial wall 239.

Auxiliary lug 334 increases the bone-contacting surface area provided by femoral component 220, thereby enhancing the strength of fixation of component 220 to the distal resected femur. The surfaces of auxiliary lug 334 may be affixed to the bone by porous material, bone cement or surface texture, for example, in a similar fashion to the lateral and medial faces of walls 238, 239 as discussed above.

In use, a slot is resected in the distal resected surface of the femur, with the slot sized and positioned to accommodate auxiliary lug 334. Advantageously, the resected slots in the femur are clearly visible to the surgeon as femoral component 220 is advanced toward the femur upon final implantation. If the anterior and distal facets of the femur (i.e., the resected surfaces created to abut anterior and posterior bone-contacting surfaces 250, 258 respectively) are obscured during implantation, such as by the adjacent tissues of the knee, the surgeon will nevertheless be able to visualize the proper implanted orientation of femoral component 220 by aligning auxiliary lug 324 to the visible resected slot in the distal femur, and then verify such alignment by tactile feedback as femoral component 220 is seated upon the resected bone surface.

In the illustrated embodiment, auxiliary lug 334 has a generally triangular shape and is substantially perpendicular to lateral wall 238. However, it is contemplated that auxiliary lug 334 may have other shapes and/or spatial arrangements. For example, lug 334 may have rounded corners, squared corners, and/or leading edges that are pointed, rounded or squared.

10. Bone Conservation: Reduced Incremental Growth Between Sizes.

Referring now to FIG. 13A, anteroposterior sizing extent 340 of femoral component 20 is illustrated. Extent 340 is measured beginning from intersection point 342 between anterior bone contacting surface 50 and distal bone contacting surface 54, with surfaces 50, 54, extrapolated distally and anteriorly to form intersection point 342. The other end of extent 340 is posterior-most contact points 34 and/or 36 (discussed in detail above).

Figure 13B:
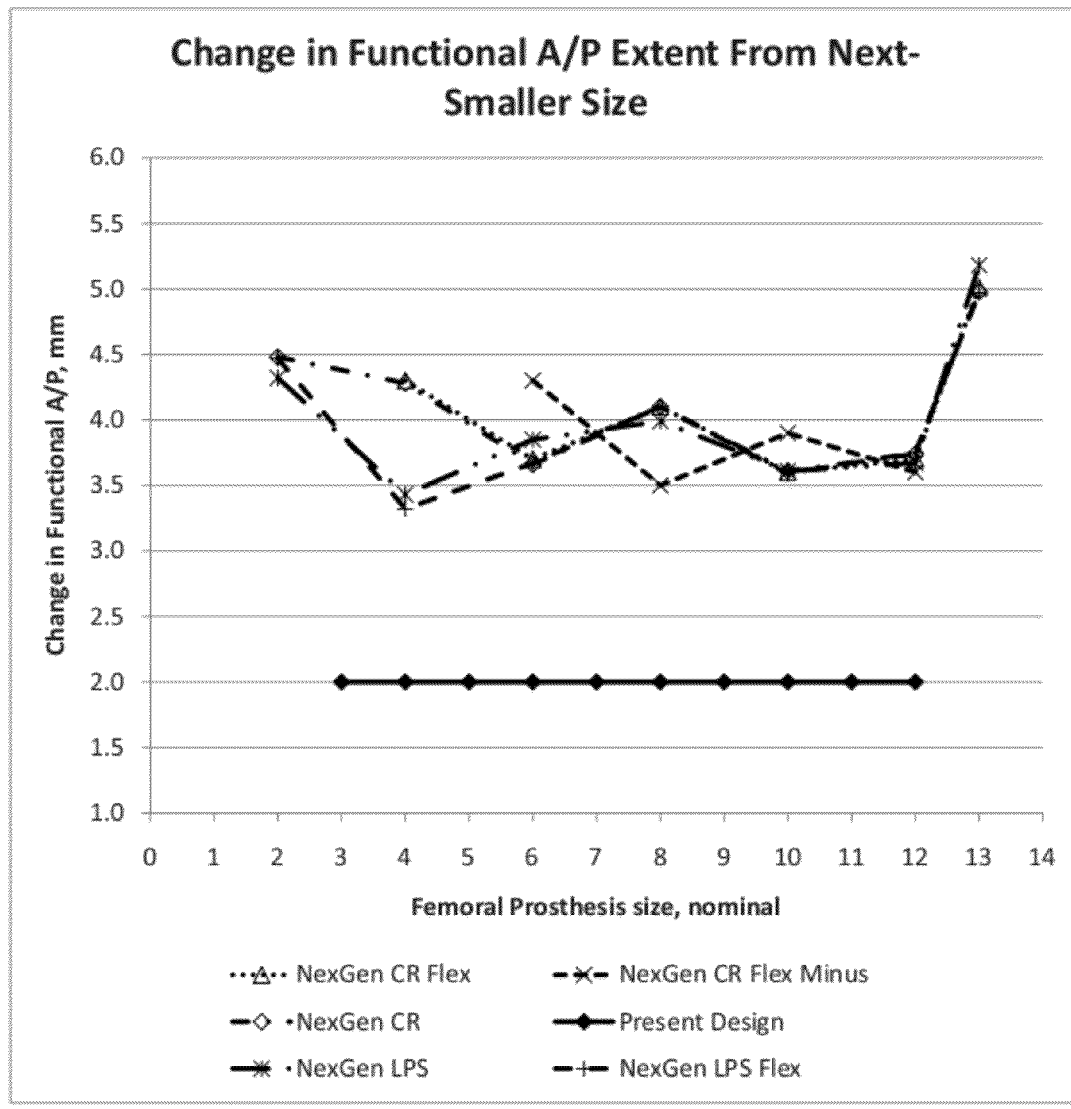
FIG. 13B is a graph plotting the functional anterior/posterior extents of the differently sized femoral components of FIG. 13A, as compared to prior art devices.

As noted herein, an exemplary knee prosthesis system in accordance with the present disclosure includes twelve separate component sizes, each of which defines a different and unique anteroposterior sizing extent 340. As between any adjacent pair of sizes (e.g. sizes 1 and 2, sizes 6 and 7 or sizes 11 and 12), a common difference 344 is defined between the respective anteroposterior extents 340 of the pair of sizes, as shown in FIG. 13B. FIG. 13B illustrates that difference 344 is 2 mm across a range of prosthesis sizes, while corresponding prior art size ranges have corresponding differences that are larger than 2 mm and not consistent across the range of sizes. In an exemplary embodiment, the associated family of femoral prostheses may be as little as 3 sizes and as large as 12 sizes. The prior art devices shown in FIG. 13B include cruciate-retaining designs, in particular the femoral components of the prior art Zimmer NexGen CR Flex prosthesis system, discussed above, and femoral components of the prior art Zimmer NexGen CR prosthesis system, shown in the "NexGen Complete Knee Solution, Implant Options, Surgeon-Specific," submitted on even date herewith in an Information Disclosure Statement, the entire disclosure of which is hereby expressly incorporated herein by reference. FIG. 13B also includes posterior-stabilized prior art designs, in particular the femoral components of the prior art Zimmer NexGen LPS Flex prosthesis system, and the femoral components of the prior art Zimmer NexGen LPS prosthesis system, shown in the "Zimmer® NexGen® LPS-Flex Mobile and LPS-Mobile Bearing Knees" product brochure and "Zimmer® NexGen® LPS Fixed Knee, Surgical Technique", both submitted on even date herewith in an Information Disclosure Statement, the entire disclosures of which are hereby expressly incorporated herein by reference.

Advantageously, measuring anteroposterior extent 340 from the virtual intersection point 342 to posterior most contact point 34 establishes size increments irrespective of changes to anterior flange 22 across sizes. For example, as shown in FIG. 13A, anterior flange 50A of the next incrementally larger-size femoral component 20A is longer and wider. Therefore, difference 344, designed to be constant among respective adjacent pairs of sizes, would be effected by this changing geometry of flange 22A.

However, it is desirable to include only incremental anteroposterior growth/shrinkage of posterior most contact point 34A in selecting size increments, so that a change in size has a predictable effect on mid-flexion soft tissue balancing of the knee. Thus, incremental size growth having a common anteroposterior difference 344 defined between any respective pair of sizes provides a uniform and consistent effect on soft tissue balancing as between any pair of sizes across the size range. This, in turn, promotes shorter operative times and allows for implant designers to optimize anterior flange 22 without impacting the consistency of growth between sizes. Further, by providing twelve standard sizes with unique anteroposterior extents 340, greater patient specificity may be achieved as compared with alternative systems having fewer size options.

In an exemplary embodiment, a surgeon may resect a patient's femur to accept the largest of a range of candidate prosthesis sizes identified by the surgeon (such as, for example, by pre-operative imaging). If the surgeon subsequently decides to "downsize" to the next-smallest size of femoral component 20, the posterior and posterior-chamfer facets of the resected bone surface (i.e., the facets corresponding to posterior chamfer surface 56 and posterior surface 58) may be further resected, with 2 mm of bone removed from posterior surface 58 to correspond to anteroposterior difference 344. To effect such further resection, an appropriately configured cutting guide may be used. Alternatively, the surgeon may employ a provisional femoral component utilizing appropriately sized resection slots, such as by using the system and method disclosed in U.S. Patent Application Publication Serial No. 2012/0078263, filed Sep. 9, 2011 and entitled BONE PRESERVING INTRAOPERATIVE DOWNSIZING SYSTEM FOR ORTHOPAEDIC IMPLANTS, the entire disclosure of which is hereby expressly incorporated herein by reference.

11. Bone Conservation: Revisable Bone Contacting Fixation Area.

As shown in FIG. 14A, femoral component 20 includes recessed pocket 336 formed as part of bone contacting surfaces 50, 54 and 58 and chamfers 52, 56. Recessed pocket 336 is surrounded by peripheral rail 337, similar to medial and lateral rails 59M, 59L shown in FIG. 9A and discussed in detail above. Recessed pocket 336 is interrupted by fixation pegs 28 and thickness ridge 300. Aside from the small areas occupied by rail 337, pegs 28 and ridge 300, the entirety of bone contacting surfaces 50, 54 and 58 and chamfers 52 and 56 are available to receive cement or porous ingrowth material for fixation of femoral component 20 to the adjacent resected facets on the distal femur. In an exemplary embodiment, rails 59M, 59L are elevated above the surfaces of recessed pocket 336 by between 1.1 and 1.2 mm.

Advantageously, recessed pocket 336 is larger than alternative devices by up to 40%, thereby providing a larger fixation area for more robust fixation to the distal femur. More particularly, in an exemplary embodiment femoral component 20 may have a total fixation area within recessed pocket 336 of as little as 2272 mm$^3$ for a small-size prosthesis and as much as 5343 mm$^3$ for a large-size prosthesis, representing between 79% and 88% of the total aggregated surface area of bone-contacting surfaces 50, 52, 54, 56, 58 across all prosthesis sizes. Advantageously, this range of surface area coverage represents an increase in surface area coverage of at least 14%, as compared to comparable prosthesis sizes in the above-mentioned prior art cruciate-retaining prostheses.

In some instances, it may be necessary to perform a revision surgery in which femoral component 20 is removed from the distal femur and replaced with a new femoral component. In order to facilitate this process, osteotome 350 having blade 352 may access the entirety of recessed pocket 336 either from the outer periphery along rail 337, or via intercondylar notch 68 and the intercondylar portion of rail 337. When blade 352 is worked around the entirety of rail 337 in this way, all of the bone cement or porous fixation material may be dislodged from the distal femur by osteotome 350. Full dislodging femoral component 20 from the distal femur prior to removal in a revision surgery protects the integrity of the remaining bone.

Turning now to FIG. 14B, posterior stabilized femoral component 220 includes recessed pocket 338 surrounded by rail 237, which are generally similar to recessed pocket 336 and rail 337 described above. In an exemplary embodiment, rail 237 is elevated above the surfaces of recessed pocket 338 by between 1.1 and 1.2 mm. However, the proximally extending lateral and medial intercondylar walls 238, 239 of intercondylar notch 268 (described in detail above) preclude blade 352 of osteotome 350 from accessing the bone-contacting space between walls 238, 239 and adjacent fixation pegs 28.

To facilitate potential revision surgery, femoral component 220 includes recessed pocket interruptions in the form of lateral and medial ridges 346, 348. Lateral ridge 346 directly abuts the distal resected facet on femur F (FIG. 11) when femoral component 220 is implanted thereon, thereby preventing bone cement or porous ingrowth material from inhabiting the space between lateral wall 238 and peg 28. Similarly, medial ridge 348 occupies the space between medial wall 239 and peg 28, also preventing bone cement or porous ingrowth material from inhabiting this space upon implantation. In an exemplary embodiment, ridges 346, 348 are elevated above the surrounding surfaces of recessed pocket 338 by the same amount as rail 337, i.e., between 1.1 and 1.2 mm.

Referring still to FIG. 14B, lateral and medial ridges 346, 348 define ridge sidewalls disposed entirely anterior or posterior of the periphery of pegs 28, (i.e., as viewed "from the side" in a sagittal plane or "from the top" in a transverse plane). Thus, no portion of the sidewalls of ridges 346, 348 is inaccessible to blade 352 of osteotome 350 as blade 352 enters from rail 237 and sweeps along a medial-to-lateral or lateral-to-medial direction. Accordingly, blade 352 can reach every other portion of recessed pocket 338 via rail 237 surrounding outer periphery of femoral component 220 in similar fashion as described above. Accordingly, femoral component 220 may be fully dislodged from femur F prior to removal therefrom during revision surgery.

Similar to recessed pocket 336 discussed above, recessed pocket 338 is also larger than alternative devices by up to 40%, thereby providing a larger fixation area for more robust fixation to the distal femur. More particularly, in an exemplary embodiment femoral component 220 may have a total fixation area within recessed pocket 338 of as little as 2128 mm$^3$ for a small-size prosthesis and as much as 4780 mm$^3$ for a large-size prosthesis, representing between 77% and 85% of the total aggregated surface area of bone-contacting surfaces 50, 52, 54, 56, 58 across all prosthesis sizes. Advantageously, this range of surface area coverage represents an increase in surface area coverage of at least 15%, as compared to comparable prosthesis sizes in the above-mentioned prior art posterior-stabilized prostheses.

While the disclosure has been described as having exemplary designs, the present disclosure can be further modified within the spirit and scope of this invention. This application is therefore intended to cover any variations, uses or adaptations of the disclosure using its general principles. Further, this application is intended to cover such departures from the present disclosure as come within known or customary practice in the art to which this disclosure pertains.

What is claimed is:

1. A family of femoral components comprising a plurality of nominal femoral component sizes including a smallest nominal femoral component size, each of said family of femoral components adapted to articulate with a tibial articular surface to form a knee prosthesis, each of said family of femoral components comprising:
   medial and lateral condyles shaped to articulate with the tibial articular surface through a range of motion, in which full extension corresponds to zero degrees flexion of the knee prosthesis and positive flexion corresponds to greater than zero degrees flexion of the knee prosthesis, said medial and lateral condyles defining medial and lateral J-curves,
   said medial J-curve comprising:
      a medial initial-flexion articular segment positioned to engage a medial compartment of the tibial articular surface from said full extension to an intermediate degree of flexion; and
      a medial deep-flexion articular segment positioned to engage the me compartment from said intermediate degree of flexion to a high degree of flexion, at least part of said medial deep-flexion articular segment defining a medial deep-flexion radius swept through a medial deep-flexion angular extent to define a medial deep-flexion arc length, such that a medial bulbousness ratio is defined as said medial deep-flexion arc length divided by said medial deep-flexion angular extent,
   said lateral J-curve comprising:
      a lateral deep-flexion articular segment positioned to engage a lateral compartment of the tibial articular surface from said full extension to said intermediate degree of flexion; and
      a lateral deep-flexion articular segment positioned to engage the lateral compartment from said intermediate degree of flexion to said high degree of flexion, at least part of said lateral deep-flexion articular segment defining a lateral deep-flexion radius swept through a lateral deep-flexion angular extent to define a lateral deep-flexion arc length, such that a lateral bulbousness ratio is defined as said lateral deep-flexion arc length divided by said lateral deep-flexion angular extent,
   wherein said medial and lateral bulbousness ratios are between 0.172 mm/degree for the smallest nominal femoral component size and 0.219 mm/degree for a largest nominal femoral component size among said plurality of nominal femoral component sizes, whereby the deep-flexion articular segment of at least one of the medial and lateral J-curves defines a bulbousness sagittal posterior geometry for each of the family of femoral components.

2. The family of femoral components of claim 1, wherein said family of femoral components comprises at least 4 nominal component sizes.

3. The family of femoral components of claim 1, wherein each of said family of femoral components comprises a cruciate-retaining type femoral component lacking a femoral cam spanning an intercondylar notch formed between said medial and lateral condyles.

4. The family of femoral components of claim 1, wherein said medial J-curve comprises:
   a medial distal-most point corresponding with said full extension;
   a medial posterior-most point corresponding with 90-degrees flexion, said medial initial-flexion articular segment of said medial J-curve disposed between said medial distal-most point and said medial posterior-most point; and
   a medial proximal-most point corresponding with a deep-flexion orientation greater than 90-degrees, said medial deep-flexion articular segment of said medial J-curve disposed between said medial posterior-most point and said medial proximal-most point.

5. The family of femoral components of claim 4, wherein said medial proximal-most point corresponds with flexion of at least 130-degrees, such that each of said family of femoral components comprises a high-flexion femoral component in which said medial and lateral condyles are shaped to enable the range of motion equal to at least 130 degrees.

6. The family of femoral components of claim 1, wherein said lateral J-curve comprises:
   a lateral distal-most point corresponding with said full extension;
   a lateral posterior-most point corresponding with 90-degrees flexion, said medial initial-flexion articular segment of said lateral J-curve disposed between said lateral distal-most point and said lateral posterior-most point; and
   a lateral proximal-most point corresponding with a deep-flexion orientation greater than 90-degrees, said lateral deep-flexion articular segment of said lateral J-curve is disposed between said lateral posterior-most point and said lateral proximal-most point.

7. The family of femoral components of claim 6, wherein said lateral proximal-most point corresponds with flexion of at least 130-degrees, such that each of said family of femoral components comprises a high-flexion femoral component in which said medial and lateral condyles are shaped to enable the range of motion equal to at least 130 degrees.

8. The family of femoral components of claim 1, wherein 90-degrees flexion of the medial and lateral condyles corresponds to medial and lateral posterior-most points on said medial and lateral condyles, respectively, and at least one of said medial and lateral condyles defines a maximum mid-flexion thickness, located in the region of said posterior-most point, up to 8 mm for the smallest nominal femoral component size in the family of femoral components and up to 9 mm for a largest nominal femoral component size in the family of femoral components.

9. The family of femoral components of claim 1, wherein 90-degrees flexion of the medial and lateral condyles corresponds to medial and lateral posterior-most points on said medial and lateral condyles, respectively, and at least one of said medial and lateral condyles defines a maximum mid-flexion thickness, located in the region of said posterior-most point, up to 9 mm for each of at least three nominal sizes in the family of femoral components.

10. A family of posterior-stabilized femoral components comprising a plurality of nominal femoral component sizes, each of said family of femoral components adapted to articulate with a tibial bearing component to form a knee prosthesis, each of said family of femoral components comprising:
    medial and lateral condyles shaped to articulate with the tibial bearing component through a range of motion, in which full extension corresponds to zero degrees flexion of the knee prosthesis and positive flexion corresponds to greater than zero degrees flexion of the knee prosthesis, said medial and lateral condyles defining medial and lateral J-curves,
    said medial and lateral condyles comprising inwardly facing condylar walls forming an intercondylar space therebetween, said intercondylar space having a medial/lateral width; and
    a femoral cam spanning said intercondylar space to join said medial and lateral condyles to one another, said femoral cam sized and positioned to engage a spine of the tibial bearing component in positive flexion through at least a portion of the range of motion,
    said medial J-curve comprising:
        a medial initial-flexion articular segment positioned to engage a medial articular compartment of the tibial bearing component from said full extension to an intermediate degree of flexion; and
        a medial deep-flexion articular segment positioned to engage the medial articular compartment from said intermediate degree of flexion to a high degree of flexion, at least part of said medial deep-flexion articular segment defining a medial deep-flexion radius swept through a medial deep-flexion angular extent to define a medial deep-flexion arc length, such that a medial bulbousness ratio is defined as said medial deep-flexion arc length divided by said medial deep-flexion angular extent,
    said lateral J-curve comprising:
        a lateral initial-flexion articular segment positioned to engage a lateral articular compartment of the tibial bearing component from said frill extension to said intermediate degree of flexion; and
        a lateral deep-flexion articular segment positioned to engage the lateral articular compartment from said intermediate degree of flexion to said high degree of flexion, at least part of said lateral deep-flexion articular segment defining a lateral deep-flexion radius swept through a lateral deep-flexion angular extent to define a lateral deep-flexion arc length, such that a lateral bulbousness ratio is defined as said lateral deep-flexion arc length divided by said lateral deep-flexion angular extent,
    wherein at least one of said medial and lateral bulbousness ratios is equal to up to 0.24 mm/degree across a range of at least three nominal component sizes within the family of femoral components, whereby the deep-flexion articular segment of at least one of the medial and lateral J-curves defines a bulbousness sagittal posterior geometry for each of the family of femoral components.

11. The family of femoral components of claim 10, wherein said at least one of said medial and lateral bulbousness ratios is equal to 0.24 mm/degree for a largest nominal femoral component size among said plurality of nominal femoral component sizes.

12. The family of femoral components of claim 10, wherein said at least one of said medial and lateral bulbousness ratios is equal to as little as 0.21 mm/degree for a smallest nominal femoral component size among said plurality of nominal femoral component sizes.

13. The family of femoral components of claim 10, wherein said family of femoral components comprises at least 4 nominal component sizes.

14. The family of femoral components of claim 13, wherein said at least one of said medial and lateral bulbousness ratios is equal to as little as 0.21 mm/degree for a smallest nominal femoral component size among said plurality of nominal femoral component sizes, and is equal to as much as 0.24 mm/degree for a largest nominal femoral component size among said plurality of nominal femoral component sizes.

15. The family of femoral components of claim 10, wherein said medial J-curve comprises:
    a medial distal-most point corresponding with said full extension;
    a medial posterior-most point corresponding with 90-degrees flexion, said medial initial-flexion articular segment of said medial J-curve disposed between said medial distal-most point and said medial posterior-most point; and
    a medial proximal-most point corresponding with a deep-flexion orientation greater than 90-degrees, said medial deep-flexion articular segment of said medial J-curve is disposed between said medial posterior-most point and said medial proximal-most point.

16. The family of femoral components of claim 15, wherein said medial proximal-most point corresponds with flexion of at least 130-degrees, such that each of said family of femoral components comprises a high-flexion femoral component in which said medial and lateral condyles are shaped to enable the range of motion equal to at least 130 degrees.

17. The family of femoral components of claim 10, wherein said lateral J-curve comprises:
    a lateral distal-most point corresponding with said full extension;
    a lateral posterior-most point corresponding with 90-degrees flexion, said medial initial-flexion articular segment of said lateral J-curve disposed between said lateral distal-most point and said lateral posterior-most point; and
    a lateral proximal-most point corresponding with a deep-flexion orientation greater than 90-degrees, said lateral deep-flexion articular segment of said lateral J-curve is disposed between said lateral posterior-most point and said lateral proximal-most point.

18. The family of femoral components of claim 17, wherein said lateral proximal-most point corresponds with flexion of at least 130-degrees, such that each of said family of femoral components comprises a high-flexion femoral component in which said medial and lateral condyles are shaped to enable the range of motion equal to at least 130 degrees.

19. The family of femoral components of claim 10, wherein said maximum mid-flexion thickness of at least one of said medial and lateral condyles is up to 9 mm for a smallest nominal size of the family of femoral components and up to 10 mm for a largest nominal size of the family of femoral components.

20. The family of femoral components of claim 10, wherein 90-degrees flexion of the medial and lateral condyles corresponds to medial and lateral posterior-most points on said medial and lateral condyles, respectively, and at least one of said medial and lateral condyles defines a maximum mid-flexion thickness, located in the region of said posterior-most points, up to 10 mm across the range of the at least three nominal component sizes within the family of femoral components.

* * * * *